United States Patent [19]

Miller et al.

[11] Patent Number: 5,753,671
[45] Date of Patent: May 19, 1998

[54] IMIDAZOPYRIDINE DERIVATIVES AS DUAL HISTAMINE ($H_1$) AND PLATELET ACTIVATING FACTOR (PAF) ANTAGONISTS

[75] Inventors: Andrew Miller; Stephen Arthur Bowles; Andrew Paul Ayscough; Mark Whittaker, all of Oxford, United Kingdom

[73] Assignee: British Biotech Pharmaceuticals Limited, England

[21] Appl. No.: 776,783

[22] PCT Filed: Aug. 9, 1995

[86] PCT No.: PCT/GB95/01878

§ 371 Date: Feb. 10, 1997

§ 102(e) Date: Feb. 10, 1997

[87] PCT Pub. No.: WO96/05201

PCT Pub. Date: Feb. 22, 1996

[30] Foreign Application Priority Data

Aug. 10, 1994 [GB] United Kingdom ............ 9416143
Mar. 22, 1995 [GB] United Kingdom ............ 9505808

[51] Int. Cl.⁶ .................. A61K 31/435; A61K 31/415; C07D 471/04
[52] U.S. Cl. .................. 514/303; 546/118; 548/306.4; 548/307.1; 548/307.4; 548/309.7; 514/394; 514/395

[58] Field of Search ................ 546/118; 514/303

[56] References Cited

FOREIGN PATENT DOCUMENTS

92/14734   9/1992   WIPO.

*Primary Examiner*—Johann Richter
*Assistant Examiner*—Laura L. Stockton
*Attorney, Agent, or Firm*—Banner & Witcoff, Ltd.

[57] ABSTRACT

Described herein are compounds of formula (II)

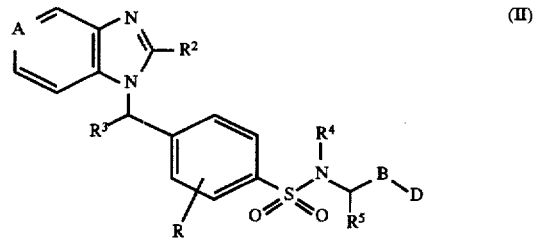

pharmaceutical or veterinary compositions thereof, and methods of treating diseases or conditions mediated by histamine and/or PAF in mammals.

19 Claims, No Drawings

IMIDAZOPYRIDINE DERIVATIVES AS DUAL HISTAMINE (H₁) AND PLATELET ACTIVATING FACTOR (PAF) ANTAGONISTS

This application is a 371 of PCT/GB95/01878 filed Aug. 9, 1995. This invention relates to compounds which are dual histamine ($H_1$) and platelet activating factor (PAF) antagonists, to therapeutic compositions containing such compounds, and to methods for their preparation.

BACKGROUND TO THE INVENTION

Potent $H_1$ antagonists of various structural types are known, and are useful in treating the symptoms of inflammatory conditions such as allergic rhinitis, and allergic conditions of the skin, which are mediated at least in part by the release of histamine. However, in such conditions, in which histamine release plays a causative role, there may be other mechanisms at work which are not inhibited by treatment with an $H_1$ antagonist alone. For example PAF is released directly from cell membranes and mediates a range of potent and specific effects on target cells resulting in a wide variety of physiological responses, including hypotension, thrombocytopenia, bronchoconstriction, circulatory shock, increased vascular permeability (oedema/erythema), and accumulation of inflammatory cells in the lower airways.

There is therefore a need for agents which have dual $H_1$ and PAF antagonistic activity for the improved treatment of conditions mediated by histamine and PAF release. Such conditions include allergic rhinitis, sinusitis, asthma, dermatitis, psoriasis, urticaria, anaphylactic shock, conjunctivitis, pruritis, inflammatory bowel disease and colitis.

International patent application WO-A-92/03423 (British Bio-technology) discloses a series of compounds which are potent antagonists of PAF. The compounds there disclosed are of the general formula (I)

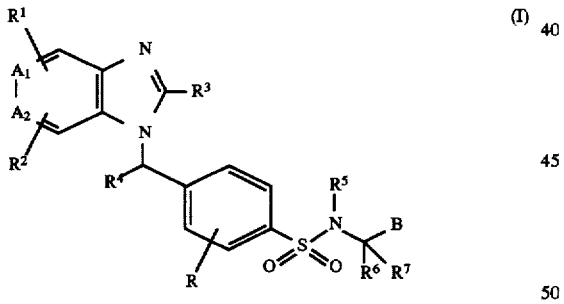

with the various substituents $A_1$, $A_2$, B and $R$–$R^7$ being as defined in the publication itself. Other patent publications which disclose compounds with PAF antagonist activity are EP-B-0404797 (Searle), EP-A-0260613 (Searle), WO 89/08653 (Searle), WO 91/17162 (Pfizer), and WO 92/03422, WO 92/18503, WO 93/02080, WO 93/16075, WO 93/14072 and WO 93/1406 9 (all British Biotech).

U.S. Pat. No. 2,712020, European patent applications EP-A-085959 and EP-A-133534 (Welcome Foundation Ltd); EP-A-270818 (Schering Corporation); and United States patent application Ser. No. 4,254,129 (Richardson Merrell Inc.) all disclose compounds which are potent $H_1$ an tagonists.

Patent applications WO-A-92/14734 (Pfizer); WO-A-92/00293, WO-A-89/10363, WO-A-93/20080, WO-93/20063, WO-A-93/23400, WO-A-93/02081 (all Schering); WO-A-94/08581 (Toray); EP-A-515158 (Schering); EP-A-463873 and EP-A-549364 (Sankyo); EP-A-577957 (Uriach); EP-A-339978, and Japanese patent application published under no 4-226993 (Yoshitomi) all disclose compounds which possess both histamine ($H_1$) and PAF antagonist activity.

BRIEF DESCRIPTION OF THE INVENTION

The invention makes available a class of compounds with some of the structural features of the potent PAF antagonists of WO-A-92/03423, and some of the structural features of certain known $H_1$ antagonists, united in a single molecule in such a way as to provide a desirable balance of $H_1$ and PAF antagonist activity. The class includes compounds which are active when administered by the oral route.

DETAILED DESCRIPTION OF THE INVENTION

According to the present invention there is provided a compound of formula (II)

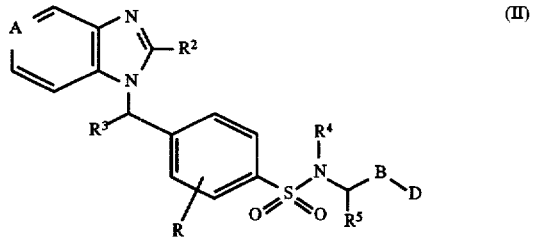

wherein

A represents =N—, =CH— or =$CR^1$—, wherein $R^1$ represents hydrogen, $C_1$–$C_6$ alkyl, $C_2$–$C_6$ alkenyl, halogen, —CN, —$CO_2H$, —$CO_2(C_1$–$C_6$ alkyl), —$CONH_2$, —CHO, —$CH_2OH$, —$CF_3$, $C_1$–$C_6$ alkoxy, $C_1$–$C_6$ alkylsulphanyl, $C_1$–C6 alkylsulphinyl, $C_1$–C6 alkylsulphonyl, —$NH_2$, —$NHCOCH_3$, or —$NO_2$; provided that when A represents =N— the resulting imidazo[4,5-c]pyridinyl bicyclic ring system may be optionally substituted in the 4- and/or 6-positions by methyl;

R represents hydrogen, $C_1$–$C_6$ alkyl, $C_2$–$C_6$ alkenyl, halogen or $C_1$–$C_6$ alkoxy;

$R^2$ represents hydrogen, $C_1$–$C_6$ alkyl, $C_2$–$C_6$ alkenyl, $C_1$–$C_6$ alkoxy, $C_1$–$C_6$ alkylsulphanyl, cyclopropyl, $C_1$–$C_6$ hydroxyalkyl, $(C_1$–$C_6$ alkyl$)_2$N—, $(C_1$–$C_6$ alkyl$)_2$ $N(C_1$–$C_6$ alkyl)- or —$CF_3$;

$R^3$ represents hydrogen, $C_1$–$C_6$ alkyl, $C_2$–$C_6$ alkenyl, $C_2$–$C_6$ alkynyl, —$CO_2(C_1$–$C_6$ alkyl), $C_1$–$C_6$ alkoxy, $C_1$–$C_6$ alkylsulphanyl, $(C_1$–$C_6$ alkoxy)($C_1$–$C_6$ alkyl)-, $(C_1$–$C_6$ alkylsulphanyl)($C_1$–$C_6$ alkyl)-, (phenyl)($C_1$–$C_6$ alkyl)-, or phenylsulphanyl;

$R^4$ represents hydrogen, $C_1$–$C_6$ alkyl, $C_2$–$C_6$ alkenyl, $C_2$–$C_6$ alkynyl, $C_1$–$C_6$ alkylcarbonyl, —$CO_2(C_1$–$C_6$ alkyl), (phenyl)$C_1$–$C_6$ alkylcarbonyl-, —C(=O)O—($C_1$–$C_6$ alkyl)-(phenyl), $(C_1$–$C_6$ alkoxy)($C_1$–$C_6$ alkyl)-, $(C_1$–$C_6$ alkylsulphanyl)($C_1$–$C_6$ alkyl)-,-($C_1$–$C_6$ alkyl) —C(=O)O—($C_1$–$C_6$ alkyl), $(C_3$–$C_8)$cycloalkyl, $(C_4$–$C_8)$cycloalkenyl, or a group of formula (III)

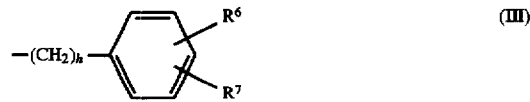

wherein h is 0 or an integer from 1 to 3, and each of $R^6$ and $R^7$ is independently hydrogen, $C_1$–$C_6$ alkyl, $C_2$–$C_6$ alkenyl, $C_2$–$C_6$ alkynyl, halogen, —CN, —CO$_2$H,—CO$_2$(C$_1$–C$_6$ alkyl), —CONH$_2$, —CONH (C$_1$–C$_6$ alkyl), —CON(C$_1$–C$_6$ alkyl)$_2$, —CHO,— CH$_2$OH, —CF$_3$, C$_1$–C$_6$ alkoxy, C$_1$–C$_6$ alkylsulphanyl, C$_1$–C$_6$ alkylsulphinyl, C$_1$–C$_6$ alkylsulphonyl, —NH$_2$, or —NHCOCH$_3$;

R$^5$ represents hydrogen, halogen, C$_1$–C$_6$ alkyl optionally substituted with one or more halogen atoms, C$_2$–C$_6$ alkenyl, C$_2$–C$_6$ alkynyl, (C$_1$–C$_6$ alkyl)—C(=O)O—(C$_1$–C$_6$ alkyl), (C$_1$–C$_6$ alkoxy)C$_1$–C$_6$ alkyl, (C$_1$–C$_6$ alkylsulphanyl)C$_1$–C$_6$ alkyl, -(C$_1$–C$_6$ alkyl)N(C$_1$–C$_6$ alkyl)$_2$, (C$_3$–C$_8$)cycloalkyl, (C$_4$–C$_8$)cycloalkenyl, ((C$_3$–C$_8$) cycloalkyl)C$_1$–C$_6$ alkyl, ((C$_4$–C$_8$) cycloalkenyl)C$_1$–$_{C6}$ alkyl, ((C$_3$–C$_8$)cycloalkyl)—O—(C$_1$–C$_6$ alkyl), ((C$_4$–C$_8$)cycloalkenyl)—O—(C$_1$–C$_6$ alkyl), ((C$_3$–C$_8$)cycloalkyl)—S—(C$_1$–C$_6$ alkyl), ((C$_4$–C$_8$)cycloalkenyl)—S—(C$_1$–C$_6$ alkyl), a side chain of a naturally occurring amino acid, or a group of formula (III) as defined above;

B represents a bond, or a straight saturated or unsaturated hydrocarbon chain of from 1 to 6 carbon atoms which may additionally include from 1 to 3 non-adjacent hetero atoms or groups selected from —O—, —S—, —N(R$^4$)— wherein R$^4$ is as defined above, —S(O)—, —S(O$_2$)—, and —S(O$_2$)N(R$^4$)— wherein R$^4$ is as defined above, and in which one or more carbon atoms of the chain may be substituted by oxo, hydroxy, C$_1$–C$_4$ alkyl, phenyl, or -phenyl(C$_1$–C$_4$ alkyl);

D represents a group of formula (IV), (V), (VI), (VII) or (VIIA)

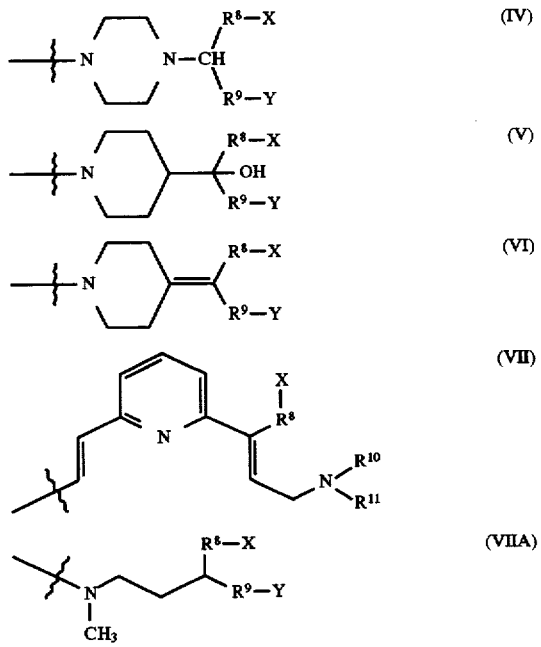

wherein R$^8$ and R$^9$ are the same or different and each represents an optionally substituted divalent phenylene group or an optionally substituted 5–6 membered monocyclic divalent heteroarylene group containing at least one nitrogen, oxygen or sulphur atom, wherein any optional substituents are selected from C$_1$–C$_6$ alkyl, C$_2$–C$_6$ alkenyl, HOOC—(C$_2$–C$_6$ alkenyl), halogen or C$_1$–C$_6$ alkoxy groups, and X and Y are independently hydrogen or when taken together in groups (IV), (V), (VI) or (VIIA) represent a divalent group selected from —CH$_2$CH$_2$—, —CH=CH—, —CH$_2$O— and —COCH$_2$—; and R$^{10}$ and R$^{11}$ are independently C$_1$–C$_6$ alkyl or together with the nitrogen atom to which they are attached form a non-aromatic 5–7 membered heterocyclic ring;

provided that when D is a group IV, V, VI or VIIA in which R$^8$ and R$^9$ are both phenylene groups and substituents X and Y are both hydrogen, then the group B does not include a carbonyl group bonded directly to D;

or a pharmaceutically or veterinarily acceptable acid addition salt or hydrate thereof.

Hereafter in this specification the term "compound" includes "salt" or "hydrate" unless the context requires otherwise.

As used herein the term "halogen" or its abbreviation "halo" means fluoro, chloro, bromo or iodo.

As used herein the term "C$_1$–C$_6$ alkyl" refers to straight chain or branched chain hydrocarbon groups having from one to six carbon atoms. Illustrative of such alkyl groups are methyl, ethyl, propyl, isopropyl, butyl, isobutyl, sec-butyl, tert-butyl, pentyl, neopentyl and hexyl.

As used herein the term "C$_2$–C$_6$ alkenyl" refers to straight chain or branched chain hydrocarbon groups having from two to six carbon atoms and having in addition one double bond, of either E or Z stereochemistry where applicable. This term would include for example, vinyl, 1-propenyl, 1- and 2-butenyl and 2-methyl-2-propenyl.

As used herein the term "C$_2$–C$_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3- hexynyl, 4-hexynyl and 5-hexynyl.

As used herein the term "C$_1$–C$_6$ alkoxy" refers to straight chain or branched chain alkoxy groups having from one to six carbon atoms. Illustrative of such alkoxy groups are methoxy, ethoxy, propoxy, isopropoxy, butoxy, isobutoxy, sec-butoxy, tert-butoxy, pentoxy, neopentoxy and hexoxy.

As used herein the term "C$_1$–C$_6$ alkylsulphanyl" refers to straight chain or branched chain alkylsulphanyl groups having from one to six carbon atoms. Illustrative of such alkyl groups are methylthio, ethylthio, propylthio, isopropylthio, butylthio, isobutylthio, sec-butylthio, tert-butylthio, pentylthio, neopentylthio and hexylthio. The terms "C$_1$–C$_6$ alkylsulphinyl" and "C$_1$–C$_6$ alkylsulphonyl" refer to the corresponding sulphinyl and sulphonyl groups respectively.

As used herein, the term "C$_3$–C$_8$ cycloalkyl" refers to an alicyclic group having from 3 to 8 carbon atoms. Illustrative of such cycloalkyl groups are cyclopropyl, cyclobutyl, cyclopentyl and cyclohexyl.

As used herein, the term "C$_4$–C$_8$ cycloalkenyl" refers to an alicyclic group having from 4 to 8 carbon atoms and having in addition one or more double bonds. Illustrative of such cycloalkenyl groups are cyclopentenyl, cyclohexenyl, cycloheptenyl and cyclooctenyl.

As used herein, the term "side chain of a naturally occurring amino acid" includes the side chains of alanine, arginine, asparagine, aspartic acid, cysteine, cystine, glutamic acid, glycine, histidine, 5-hydroxylysine, 4-hydroxyproline, isoleucine, leucine, lysine, methionine, phenylalanine, proline, serine, threonine, tryptophan, tyrosine, valine, a-aminoadipic acid, a-amino-n-butyric acid, 3,4-dihydroxyphenylalanine, homoserine, α-methylserine, ornithine, pipecolic acid, and thyroxine. The amino acid side chains may be protected; for example the carboxyl groups of aspartic acid, glutamic acid and α-aminoadipic acid may be esterified (for example as a C$_1$–C$_6$ alkyl ester), the amino groups of lysine, ornithine, 5-hydroxylysine, 4-hydroxyproline may be converted to amides (for example as a $COC_1$–$C_6$ alkyl amide) or carbamates (for example as a $C(=O)OC_1$–$C_6$ alkyl or $C(=O)OCH_2Ph$ carbamate), the hydroxyl groups of 5-hydroxylysine, 4-hydroxyproline, serine, threonine, tyrosine, $3,4$-dihydroxyphenylalanine, homoserine, α-methylserine and thyroxine may be converted to ethers (for example a $C_1$–$C_6$ alkyl or a ($C_1$–$C_6$ alkyl)phenyl ether) or esters (for example a $C(=O)C_1$–$C_6$ alkyl ester) and the thiol group of cysteine may be converted to thioethers (for example a $C_1$–$C_6$ alkyl thioether) or thioesters (for example a $C(=O)C_1$–$C_6$ alkyl thioester). The stereochemistry at the carbon atom to which the amino acid side chain is attached may be either D or L.

As used herein, the term "non-aromatic 5 to 7 membered heterocyclyl" refers to a non-aromatic monocyclic heterocyclic group having from 5 to 7 ring atoms wherein the heteroatom(s) are selected from O, S and N. Illustrative of such are pyrolyl, furanyl, oxazolyl, oxadiazolyl, thiazolyl, thiadiazolyl, pyrazolyl, pyrrolidinyl, pyrimidinyl, morpholinyl, and piperizinyl.

As used herein, the term "divalent phenylene" group means a benzene ring in which two of the ring carbon atoms, for example two adjacent ring carbon atoms, have unsatisfied valencies.

As used herein, the term "divalent heteroarylene" group means an aromatic heterocyclic ring in which two of the ring atoms, for example two adjacent ring atoms, have unsatisfied valencies.

In compounds of this invention, the presence of several asymmetric carbon atoms gives rise to diastereoisomers, each of which consists of two enantiomers, with the appropriate R or S stereochemistry at each chiral centre. The invention is understood to include all such diastereoisomers, their optically active enantiomers and mixtures thereof.

The term "pharmaceutically or veterinarily acceptable acid addition salt" refers to a salt prepared by contacting a compound of formula (I) with an acid whose anion is generally considered suitable for human or animal consumption.

Examples of pharmaceutically and/or veterinarily acceptable acid addition salts include the hydrochloride, sulphate, phosphate, acetate, propionate, lactate, maleate, succinate and tartrate salts.

In the compounds of the invention, the group B is believed to function as a flexible linker between the two halves of the molecule. As depicted in formula (II), the grouping to the left of linker group B is primarily responsible for the PAF antagonist activity of the compounds, and the group D to the right is primarily responsible for its $H_1$ activity. The invention is based at least in part on the finding of the present inventors that linking the two halves by a flexible linker of the kind defined above enables the molecule to orient itself for interaction with the PAF receptor without the $H_1$ antagonist moiety D interfering unduly with that interaction, and vice versa with respect to the $H_1$ receptor.

The linker group B may, for example, have the formula —$(CH_2)_i$—, —CO—, —$COX^1(CH_2)_i$—, —$COX^1(CH_2)_i$ $Y^1CO$—, —$COX^1(CH_2)_iY^1(CH_2)_j$—, —$(CH_2)_iX^1CO$—, —$COX^1(CH_2)_iY^1(CH_2)_jZCO$—, —$CO(CH_2)_i$—, —$(CH_2)X^1(CH_2)_i$—, —$(CH_2)_iX^1(CH_2)_iY^1(CH_2)_j$—, —$(CH_2)X^1(CH_2)_iY^1CO$—, —$(CH_2)_iX^1CO(CH_2)_j$—, —$X^1(CH_2)_i$—, —$S(CH_2)_i$—, —$SO(CH_2)_i$—, —$SO_2(CH_2)_i$—, or —$SO_2X^1(CH_2)_i$—, wherein $X_1$, $Y^1$ and Z independently represent —O— or —$NR^4$— where $R^4$ is as defined above in formula (II), and i anc j are incepenaentiy 0 or an integer from a 1 to 6, provided that no more than 6 carbon atoms are present in the linear chain represented by the foregoing formulae, and provided that where both $X^1$ and $Y^1$ are present in the linker group B then i is an integer from 1 to 6. In the foregoing formulae one or more carbon atoms of the linear chain may be substituted by hydroxy, $C_1$–$C_4$ alkyl, phenyl, or -phenyl($C_1$–$C_4$ alkyl).

Preferred compounds of formula (II) include those in which, independently or in any compatible combination:

A is =N—;

R represents hydrogen;

$R^2$ represents methyl;

$R^3$ represents hydrogen;

$R^4$ represents hydrogen, a —$C_1$–$C_6$ alkyl (for example methyl, ethyl or iso-propyl) group, a —$C_2$–$C_6$ alkenyl (for example allyl) group, a $C_1$–$C_8$ cycloalkyl (for example cyclohexyl, cyclopentyl, cyclopropyl) group, a ($C_1$–$C_6$ alkoxy)($C_1$–$C_6$ alkyl)— group (for example 1-ethoxymethyl-3-methylbut-1-yl), a —($C_1$–$C_6$ alkyl) —$C(=O)O$—($C_1$–$C_6$ alkyl) group (for example 1-ethoxycarbonyl-3-methylbut-1-yl), or a group of formula (III) above;

$R^5$ represents hydrogen, a $C_1$–$C_6$ alkyl (for example methyl, ethyl, n-butyl, i-butyl, sec-butyl or t-butyl) group, a $C_2$–$C_6$ alkenyl (for example allyl) group, a ($C_1$–$C_6$ alkyl)$C_3$–$C_8$ cycloalkyl (for example cyclopropylmethyl, cyclopentylmethyl or cyclohexylmethyl) group, a side chain of a naturally occurring amino acid (for example the side chain of leucine, isoleucine, phenylalanine, valine, tryptophan, methionine or tyrosine) or a group of formula (III) above;

in those cases where a group of formula (III) is present, $R^6$ represents a hydrogen atom, a $C_1$–$C_6$ alkyl (for example methyl) group, a halogen (for example fluorine, chlorine or bromine) atom, a $CF_3$ group or a $C_1$–$C_6$ alkoxy (for example methoxy) group; and $R^7$ represents a hydrogen atom or a $C_1$–$C_6$ alkoxy (for example methoxy) group;

the group B may be a bond, or —CO—, —$CH_2$—, —$CH_2CH_2$—, —$CH_2OCO$—, —$CH_2OCOCH_2$—, —$COO(CH_2)_2OCH_2CH_2$—, —$CONH(CH_2)_2$—, —$COOCH_2$—, —$COO(CH_2)_2$—, —$COO(CH_2)_3$—, —$CH_2OCH_2CO$—, —$CH_2$—$OCH_2CH_2$—, —$COOCH(4-tert-butylphenyl)(CH_2)_3$, —$COOCH(CH_3)(CH_2)_3$, —$CH_2NHCOCH_2$—, —$CH_2NHCO$—;

in the group D, the groupings —$R^8$—X and —$R^9$—Y may be independently a phenyl, 4-chlorophenyl, 4-fluorophenyl, 4-bromophenyl, 2-pyridyl, or 6-[2-carboxyethenyl]pyrid-2-yl group; or the group D may be of formula (VIII), (IX) or (X):

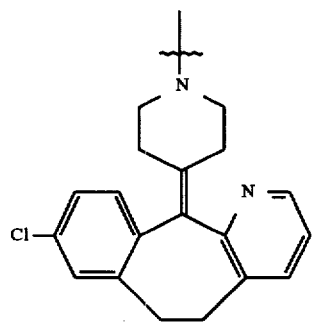

(VIII)

-continued

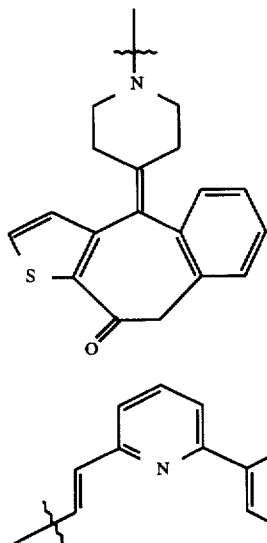

(IX)

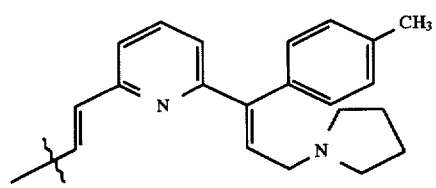

(X)

the latter group (X) being presently preferred.

Specific presently preferred compounds of the invention are:

N-Methyl-N-4-(1H-2-methylimidazo[4,5-c]pyridinylmethyl)-phenylsulphonyl-L-leucine-2-(4-benzhydryl-piperazin-1-yl)-ethyl ester, N-Methyl-N-4-(1H-2-methylimidazo[4,5-c]pyridinylmethyl)-phenylsulphonyl-L-leucine-3-(4-benzhydryl-piperazin-1-yl)-propyl ester, 4-(8-Chloro-5,6-dihydro-11H-benzo[5,6]cyclohepta[1,2-b]-pyridin-11-ylidene)-1-(N-methyl-N-4-{(1H-2-methylimidazo[4,5-c]pyridinylmethyl}-phenylsulphonyl-L-leucyl)-piperidine amide, (E)-3-[6-[Pyrrolidino-1-{4-tolyl}prop-1E-enyl]-2-pyridyl) acrylic acid, N-methyl-N-4-(1H-2-methylimidazo[4,5-c] pyridinylmethyl)-phenylsulphonyl-L-leucyl ester, N-(S)-(1-Ethoxymethyl-3-methylbutyl)-N-{(E)-3-(6-[3-pyrrolidino-1-{4-tolyl}-prop-1E-enyl]-pyridin-2-yl)-prop-2-en-1-yl}-4-(1H-2-methylimidazo[4,5-c]pyridin-1-ylmethyl)-phenylsulphonamide, and (S)-4-Methyl-2-([4-(1H-2-methylimidazo[4,5-c]pyridin-1-ylmethyl)-phenylsulphonyl]-(E)-{3-[6-(3-pyrrolidin-1-yl-{4-tolyl}-prop-1E-enyl]-prop-2-en-1-yl}-amino)-pentanoic acid ethyl ester, and pharmaceutically or veterinarily acceptable acid addition salts or hydrates thereof Additional specific compounds of the invention include:

N-Methyl-N-4-(1H-2-methylimidazo[4,5-c]pyridinylmethyl)phenylsulphonyl-L-leucine-2-(2-{4-[4-(chlorophenyl)-phenyl-methyl]-piperazin-1-yl}-ethoxy)-ethyl ester, N-Methyl-N-4-(1H-2-methylimidazo[4,5-c]pyridinylmethyl)phenylsulphonyl-L-leucine-2-(4-[1,1-dimethylethyl]phenyl)-4-(hydroxydiphenylmethyl)-1-piperidinebutyl ester, N-Methyl-N-4-(1H-2-methylimidazo[4,5-c]pyridinylmethyl)phenylsulphonyl-L-leucine-2-(4-benzhydryl-piperazin-1-yl)-ethylamide, 4-(8-Chloro-5,6-dihydro-11H-benzo[5,6]cyclohepta[1,2-b]-pyridin-11-ylidene)-1-(N-methyl-N-4-{1H-2-methylimidazo[4,5-c]pyridinylmethyl}-phenylsulphonyl-L-leucinol)-piperidine carbamate, (4-Benzhydrylpiperazin-1-yl)-acetic acid, N-methyl-N-4-(1H-2-methylimidazo[4,5-c]-pyridinylmethyl)-phenylsulphonyl-L-leucyl ester, N-Methyl-N-(S)-(1-[4-benzhydrylpiperazin-1-yl]-methyl-3-methyl-butyl)-N-4-(1H-2-methylimidazo[4,5c]pyridinylmethyl)-phenylsulphonamide, N-Methyl-N-(S)-(1-aminomethyl-[{4-benzhydrylpiperazin-1-yl}-acetamide)-3-methyl-butyl)-N-4-(1H-2-methylimidazo[4,5-c]-pyridinylmethyl)-phenylsulphonamide, N-(S)-(4-Methyl-2-{methyl-[4-(1H-2-methyl-imidazo[4,5-c]pyridin-1-ylmethyl)-phenylsulphonyl]-amino}-pentyl)-3-[6-(3-pyrrolidin-1-yl-p-tolyl-prop-1E-enyl)-pyridin-2-yl] acrylamide, 2-[4-(8-Chloro-5,6-dihydro-11H-benzo[5,6]cyclohepta[1,2-b]pyridin-11-ylidene)-piperidin-1-yl]-N-(4-methyl-2-{methyl-[4-(1H-2-methylimidazo[4,5-c]pyridin-1-ylmethyl)-phenylsulphonyl]-amino}-pentyl)-acetamide, N-[1-{(4-Chlorobenzhydryl)-piperazin-1-ylmethyl}-3-methyl-butyl]-N-methyl-4-(1H-2-methylimidazo[4,5-c]pyridin-1-ylmethyl)-phenylsulphonamide, N-Methyl-N-4-(1H-2-methylimidazo[4,5-c]pyridinylmethyl)-phenylsulphonyl-L-leucine-2-(4-{8-chloro-5,6-dihydro-11H-benzo[5,6]cyclohepta[1,2-b)pyridin-11-ylidene}piperidin-1-yl)-ethyl ester, N-Methyl-N-4-(1H-2-methylimidazo[4,5-c]pyridinylmethyl)-phenylsulphonyl-L-leucine-(R,S)-5-(4-benzhydrylpiperazin-1yl)-2-pentyl ester, 4-Methyl-2-{methyl-[4-(2-methyl-imidazo[4,5-c]pyridin-1-ylmethyl)-phenylsulphonyl]-amino}-pentanoic acid-(E)-3-(6-[3-pyrrolidino-1-{4-tolyl}-prop-1E-enyl]-pyridin-2-yl)-prop-2-en-1-yl ester, N-(1-{2-[4-(8-Chloro-5,6-dihydro-benzo[5,6]cyclohepta[1,2-b]pyridin-11-ylidene)-piperidin-1-yl]-2-oxo-ethoxymethyl}-3-methyl-butyl)-N-methyl-4-(1H-2-methylimidazo[4,5-c]pyridin-1-ylmethyl)-phenylsulphonamide, N-{2-[4-(8-Chloro-5,6-dihydro-11H-benzo[5,6]cyclohepta[1,2-b]pyridin-11-ylidene)-piperidin-1-yl]-2-oxo-ethyl}-N-(S)-(1-ethoxymethyl-3-methylbutyl)-4-(1H-2-methylimidazo[4,5-c]pyridin-1-ylmethyl)-phenylsulphonamide, N-(2-{[4-(R,S)-(4-Chlorophenyl)-phenyl-methyl]piperazin-1-yl}ethyl)-N-(S)-(1-ethoxymethyl-3-methylbutyl)-4-(1H-2-methylimidazo[4,5-c]pyridin-1ylmethyl)-phenylsulphonamide, N-(2-{[3-(R,S)-(4-Chlorophenyl)-3-pyridin-2-yl-propyl]-methylamino}ethyl)-N-(S)-(1-ethoxymethyl-3-methylbutyl)-4-(1H-2-methylimidazo[4,5-c]pyridin-1-ylmethyl)-phenylsulphonamide, N-(3-{[3-(R,S)-(4-Chlorophenyl)-3-pyridin-2-yl-propyl]-methylamino}propyl)-N-(S)-(1-ethoxymethyl-3-methylbutyl)-4-(1H-2-methylimidazo[4,5-c]pyridin-1-ylmethyl)-phenylsulphonamide, N-(3-{[4-(R,S)-(4-Chlorophenyl)-phenyl-methyl]piperazin-1-ylpropyl)-N-(S)-(1-ethoxymethyl-3-methylbutyl)-4-(1H-2-methylimidazo[4,5-c]pyridin-1ylmethyl)-phenylsulphonamide, N-Cyclohexyl-N-{(E)-3-(6-[3-pyrrolidino-1-{4-tolyl}-prop-1E-enyl]-pyridin-2-yl)-prop- 2-en-1-yl}-4-(1H-2-methylimidazo[4,5-c]pyridin-1-ylmethyl)-phenylsulphonamide, N-Methyl-N-{(E)-3-(6-[3-pyrrolidino-1-{4-tolyl}-prop-1E-enyl]-pyridin-2-yl)-prop-2-en-1-yl}-4-(1H-2-methylimidazo[4,5-c]pyridin-1-ylmethyl)-phenylsulphonamide, and pharmaceutically or veterinarily acceptable acid addition salts or hydrates thereof.

Compounds of the invention of general formula (II) may be prepared by standard techniques of organic synthesis. In considering specific synthetic routes which may be employed, it is convenient to simplify the depiction of general formula (II) as formula (IIA):

$$Q-B-D \quad \text{(IIA)}$$

wherein B and D are as defined in formula (II) and Q represents the grouping wherein A, and R–R$^5$ are as defined in formula (II).

It is also convenient to categorise compounds of the invention of formula (II) according to the identity of the first few atoms of the linker group B, counting the atom to which grouping Q is joined as position 1, the adjacent atom of the linker chain as position 2, and so on.

Route 1

Compounds of the invention in which linker B commences —C(O)O— may be prepared by esterification of an acid of formula (XI)

$$QCO_2H \quad \text{(XI)}$$

with an alcohol of formula (XII)

$$HO-B^1-D \quad \text{(XII)}$$

wherein D is as defined in formula (II) and B$^1$ is the residue of linker B (as defined in formula (II)) commencing at position 3. The esterification may be facilitated by using a carbodiimide condensing agent, such as 3-dimethylaminopropyl-1-ethyl-carbodiimide. Alternatively an activated derivative of the acid (XI) may be employed for the esterification, such as the acid chloride or pentafluorophenyl ester. Dimethylaminopyridine added to the reaction mixture may facilitate the esterification reaction and increase yield.

Route 2

Compounds of the invention in which linker B commences —C(O)N(R$^4$)— wherein R$^4$ is as defined in formula (II) may be prepared by amidation of an acid of formula (XI)

$$QCO_2H \quad \text{(XI)}$$

with an amine of formula (XIII)

$$HN(R^4)-B^1-D \quad \text{(XIII)}$$

wherein D is as defined in formula (II) and B$^1$ is the residue of linker B (as defined in formula (II)) commencing at position 3. The amidation, like the esterification reaction of Route 1, may be facilitated by using a carbodiimide condensing agent or by the use of an activated derivative of the acid (XI).

Route 3

Compounds of the invention in which linker B commences —CH$_2$OC(O)— may be prepared by esterification with an alcohol of formula (XIV)

$$QCH_2OH \quad \text{(XIV)}$$

of an acid of formula (XV)

$$HOOC-B^1-D \quad \text{(XV)}$$

wherein D is as defined in formula (II) and B$^1$ is the residue of linker B (as defined in formula (II)) commencing at position 4. The comments made in relation to the esterification conditions in Route 1 apply here also.

Route 4

Compounds of the invention in which linker B is —CH$_2$— and group D is of formula (IV), (V), (VI) or (VIIA) may be prepared by condensation of an alcohol of formula (XIV)

$$QCH_2OH \quad \text{(XIV)}$$

with an amine of formula (XVI)

$$H-D \quad \text{(XVI)}$$

The alcohol (XIV) preferably participates in the condensation reaction as the mesylate, formed from the reaction of the alcohol (XIV) with methyl sulphonyl chloride in the presence of a tertiary amine.

Route 5

Compounds of the invention in which linker B commences —CH$_2$NHC(O)— may be prepared by amidation with an amine of formula (XVII)

$$QCH_2NH_2 \quad \text{(XVII)}$$

of an acid of formula (XV)

$$HOOC-B^1-D \quad \text{(XV)}$$

wherein D is as defined in formula (II) and B$^1$ is the residue of linker B (as defined in formula (II)) commencing at position 4. The comments made in relation to the amidation conditions in Route 2 apply here also. The carbonyl group in position 3 of the linker B of the product of the foregoing reaction may be reduced to form the corresponding compounds of the invention in which linker B commences— CH$_2$NHCH$_2$—.

Route 6

Compounds of the invention in which linker B commences —CH$_2$NH— may be prepared by reaction of an amine of formula (XVII)

$$QCH_2NH_2 \quad \text{(XVII)}$$

with an aldehyde of formula (XVIII)

$$HCO-B^1-D \quad \text{(XVIII)}$$

wherein D is as defined in formula (II) and B$^1$ is the residue of linker B (as defined in formula (II)) commencing at position 4. The reaction preferably takes place in the presence of a suitable reducing agent such as sodium cyanoborohydride.

Route 7

Compounds of the invention of formula (II) may also be prepared by a process comprising reaction of a diamino compound of formula (XIX)

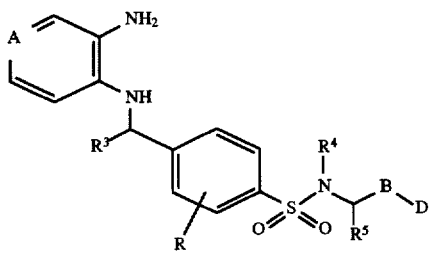 (XIX)

wherein A, R, R³-R⁵, B and D are as defined in formula (II), with a acid of formula (XX)

 (XX)

or an activated derivative thereof. This reaction is analagous to that described previously in WO 92/03423, and further details of suitable activated derivatives of acid (XX) and process conditions may be found therein.

Route 8

Compounds of the invention in which D is a group of formula (VII) as defined above and B is a bond may be prepared by reaction of a sulphonamide of formula (XXI)

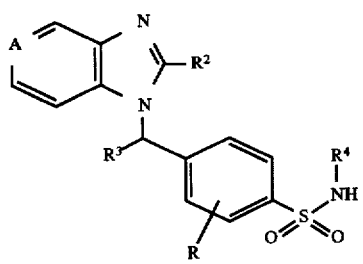 (XXI)

with an acetate of formula (XXII) in the presence of a palladium(0) catalyst, such as tetrakis(triphenylphosphine)palladium(0)

 (XXII)

Sulphonamides of formula (XXI) may be prepared using procedures analogous to those reported in WO 92/03423 or WO 92/03422.

The starting acid (XI) for routes 1 and 2 above may be prepared by hydrolysis under acidic conditions of a corresponding ester (prepared as previously described in WO 92/03423). The starting alcohol (XIV) for routes 3 and 4 above may be prepared by reduction, for example using lithium aluminium hydride, of a corresponding ester (prepared as previously described in WO 92/03423). The starting amine (XVII) for routes 5 and 6 above may be prepared by reaction of a mesylate of the alcohol (XIV) with sodium azide followed by hydrogenation over a palladium catalyst.

In addition to the above routes, compounds of the invention may be prepared by other methods and techniques analogous to those known in the art for compounds having similar structural features, and by analogy with the methods and techniques used in the specific preparative examples below.

As mentioned above, the invention makes available a class of compounds having a desirable balance of $H_1$ and PAF antagonist activity.

Accordingly in another aspect, this invention concerns:
(i) a method of management (by which is meant treatment or prophylaxis) of diseases or conditions mediated by histamine and/or PAF in mammals, in particular in humans, which method comprises administering to the mammal an effective amount of a compound as defined with respect to formula (II) above, or a pharmaceutically acceptable salt thereof; and (ii) a compound as defined with respect to formula (11) for use in human or veterinary medicine, particularly in the management (by which is meant treatment or prophylaxis) of diseases or conditions mediated by histamine and/or PAF; and (iii) the use of a compound as defined with respect to formula (II) in the preparation of an agent for the management (by which is meant treatment or prophylaxis) of diseases or conditions mediated by histamine and/or PAF.

Diseases or conditions mediated by histamine and/or PAF, but which probably include contributions from both agents, include hypotension, thrombocytopenia, bronchoconstriction, circulatory shock, increased vascular permeability (oedema/erythema), allergic rhinitis, sinusitis, asthma, dermatitis, psoriasis, urticaria, anaphylactic shock, conjunctivitis, pruritis, inflammatory bowel disease and colitis.

According to a further aspect of the invention there is provided a pharmaceutical or veterinary formulation comprising a compound of general formula (II) and a pharmaceutically and/or veterinarily acceptable carrier. One or more compounds of general formula (II) may be present in association with one or more non-toxic pharmaceutically and/or veterinarily acceptable carriers and/or diluents and/or adjuvants and if desired other active ingredients. The pharmaceutical compositions containing compounds of general formula (II) may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occuring phosphatide, for example lecithin, or condensation products of an alkylene oxide with fatty acids for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be pr esent.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parentally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the p reparation of injectables.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa buffer and polyethylene glycols.

For topical application to the skin compounds of the invention may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

For topical applications to the eye, compounds of the invention may be made up into a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine, and thickening agents such as hypromellose may also be included.

Compounds of the invention may be administered parenterally in a sterile medium. Th e drug depending on the vehicle and c oncentration used, ca n either be suspended or dissolved in the vehicle. Advantageously, adjuvants such as a local anaesthetic, preservative and buffering agents can be dissolved in the vehicle.

Compounds of the invention may be used for the treatment of the respiratory tract by nasal or buccal administration of, for example, aerosols or sprays which can disperse the pharmacologic al active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid nonionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Dosage levels of the order of from about 0.1 mg to about 140 mg per kilogram of body weight per day are useful in the treatment of the above-indicated conditions (about 0.5 mg to about 71 g per patient per day). For example, inflammation may be effectively treated by the administration of from about 0.01 to 50 mg of the compound per kilogram of body weight per day (about 1.0 mg to about 3.5 g per patient per day). The dosage employed for the topical administration will, of course, depend on the size of the area being treated. For the eyes each dose will be typically in the range from 0.1 to 10 mg of the drug.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples illustrate the invention, but are not intended to limit the scope in any way. The following abbreviations have been used in the examples:

DCM—Dichloromethane
MPLC—Medium Pressure Liquid Chromatography
DMF—Dimethylformamide
THF—Tetrahydrofuran
DIBAL—Diisobutylaluminium hydride
DMSO—Dimethylsulphoxide Column chromatography was performed with flash grade silica gel. $^1$H-NMR and $^{13}$C-NMR were recorded either on a Bruker AC-250 spectrometer at 250 MHz and 62.5 MHz respectively or on a Bruker AMX-500 spectrometer at 500 MHz and 125.72 MHz respectively. CDCl$_3$ was used as a solvent and internal reference and spectra are reported as δ ppm from TMS.

EXAMPLE 1

N-Methyl-N-4-(1H-2-methylimidazo[(4,5-c]pyridinylmethyl)-phenylsulphonyl-L-leucine-2-(2-{4-[4-(chlorophenyl)-phenyl-methyl]-piperazin-1-yl}-ethoxy)-ethyl ester.

bicarbonate. The organic layer was separated, washed with brine and dried over sodium sulphate. Filtration and evaporation of solvent under reduced pressure provided the pentafluorophenylester as a colourless oil. The residue was taken up in DCM (15 ml) and treated with 2-{4-[4-(chlorophenyl)-phenylmethyl]-piperazin-1-yl}-ethoxyethanol dihydrochloride (700 mg, 1.6 mmol) and imidazole (320 mg, 4.7 mmol). The reaction was stirred overnight at room temperature. The reaction mixture was partitioned between DCM and 10% citric acid. The organic layer was separated, washed with saturated sodium bicarbonate and brine and dried over sodium sulphate. The crude product was purified by MPLC on a silica gel column with a gradient elution 5–7% methanol in DCM over 40 minutes and a flow rate of 60 ml/min. Product containing fractions were combined and solvent removed under reduced pressure to provide N-methyl-N-4-(1H-2-methylimidazo[4,5-c]pyridinylmethylphenylsulphonyl-L-leucine-2-(2-{4-[4-(chlorophenyl)-phenyl-methyl]-piperazin-1-yl}-ethoxy)-ethyl ester as a yellow oil (648 mg, 52%).

$^1$H-NMR; δ (CDCl$_3$), 8.99 (1H, s), 8.31 (1H, d, J=5.6 Hz), 7.69 (2H, d, J=8.4 Hz), 7.34–7.06 (12H, m), 5.32 (2H, s), 4.63–4.57 (1H, m), 4.16 (1H, s), 3.89–3.79 (2H, m), 3.45–3.34 (6H, m), 2.77 (3H, s), 2.53 (3H, s), 2.49–2.29 (8H, m), 1.64–1.50 (3H, m), 0.87 (3H, d, J=5.8 Hz) and 0.86 (3H, d, J=5.8 Hz).

$^{13}$C-NMR; δ (CDCl$_3$), 170.7, 153.2, 142.0, 141.8, 141.2, 140.0, 139.7, 139.5, 139.1, 132.3, 129.0, 128.4, 128.1, 127.7, 127.0, 126.6, 104.6, 75.2, 68.8, 68.2, 63.6, 57.5, 57.0, 53.7, 51.5, 50.1, 46.7, 38.0, 29.7, 24.3, 22.8 and 20.9.

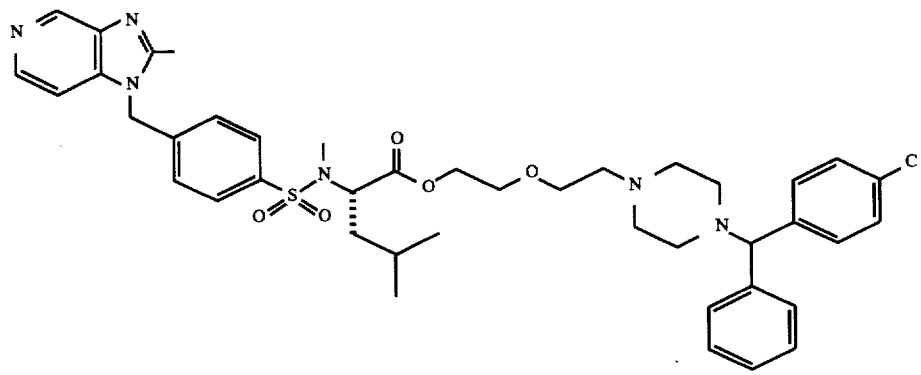

(a) N-Methyl-N-4-(1H-2-methylimidazo[4,5-c]pyridylmethyl)-phenylsulphonyl-L-leucine (675 mg, 1.6 mmol)(WO-92/03423) was dissolved in DCM (15 ml) and treated with pentafluorophenol (239 mg, 1.9 mmol), N-(3-dimethylaminopropyl)-N'-ethylcarbodiimide hydrochloride (360 mg, 1.9 mmol) and N-methylmorpholine (380 µl, 3.5 mmol). After stirring at room temperature for 3.5 hours the reaction mixture was partitioned with saturated sodium

EXAMPLE 2

N-Methyl-N-4-(1H-2-methylimidazo[4,5-c]pyridinylmethyl)-phenylsulphonyl-L-leucine-2-(4-[1,1-dimethylethyl]phenyl)-4-(hydroxydiphenylmethyl)-1-piperidinebutyl ester.

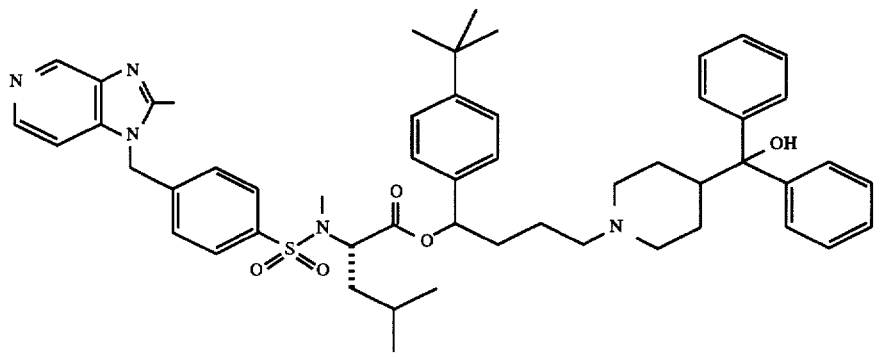

N-Methyl-N-4-(1H-2-methylimidazo[4,5-c]pyridylmethyl)-phenylsulphonyl-L-leucine (675 mg, 1.6 mmol) was reacted via a pentafluorophenyl ester derivative using conditions described in example 1 but using 4-[1,1-dimethylethyl]phenyl)-4-(hydroxydiphenylmethyl)-1-piperidinebutanol (755 mg, 1.6 mmol) in place of 2-{4-[4-(chlorophenyl)-phenylmethyl]-piperazin-1-yl}-ethoxyethanol dihydrochloride. Following column chromatography on silica gel, eluting with 3% methanol/DCM, N-methyl-N-4-(1H-2-methylimidazo[4,5-c]pyridinylmethyl)-phenylsulphonyl-L-leucine-2-(4-[1,1-dimethylethyl]phenyl)-4-(hydroxydiphenylmethyl)-1-piperidinebutyl ester was obtained as a white foam and a 2:1 mixture of diastereoisomers (at the 1,1-dimethylethylphenyl methyl group, 625 mg, 45%).

$^1$H-NMR; δ (CDCl$_3$), 8.99 (0.66H,s), 8.94 (0.33H,s), 7.73 (0.66H, d, J 8.3 Hz), 7.45–7.48 (5.33H, m), 7.31–6.81 (13H,m), 5.49–5.44 (1H, m), 5.36 (0.66H, s), 5.26 (1.33H, d, J 3.7 Hz), 4.72–4.67 (1H, m), 2.96–2.82 (2H, m), 2.78 (1H, s), 2.73 (2H, s), 2.57 (1H,s), 2.52 (2H, s), 2.52–2.35 (1H, m), 2.30–2.25 (2H, m), 2.07–1.89 (2H, m), 1.78–1.24 (11H, m), 1.28 (3H, s), 1.26 (6H, s) and 0.97–0.92 (6H, m).

$^{13}$C-NMR; δ (CDCl$_3$), 170.2, 170.6, 153.4, 151.0, 146.1, 142.0, 141.7, 140.1, 139.7, 139.4, 138.8, 136.9, 135.5, 128.1, 127.9, 126.6, 126.5, 126.3, 125.8, 125.2, 125.1, 104.7, 79.2, 76.7, 76.4, 57.6, 57.4, 57.1, 53.8, 53.7, 46.8, 44.0, 38.0, 37.6, 34.4, 34.2, 33.9, 31.7, 29.7, 29.5, 26.0, 24.3, 22.9, 22.6, 22.4, 21.0 and 13.8.

EXAMPLE 3

N-Methyl-N-4-(1H-2-methylimidazo[4,5-c]pyridinylmethyl)phenylsulphonyl-L-leucine-2-(4-benzhydryl-piperazin-1-yl)-ethyl ester.

(a) 2-(4-Benzhydry-piperazine)-ethan-2-ol

2-Bromoethanol (7.8 g, 62.4 mmol) was added to a solution of benzhydrylpiperazine in dry THF (150 ml). The reaction mixture was stirred at room temperature overnight. THF was removed under reduced pressure and the residue partitioned between ethyl acetate and saturated sodium bicarbonate solution. The organic layer was separated, dried over magnesium sulphate, filtered and solvent removed to leave 2-(4-benzhydryl-piperazine)-ethan-1-ol as a colourless oil (8.2 g, 44%).

$^1$H-NMR; δ (CDCl$_3$), 7.42 (4H, d, J=7.3 Hz), 7.27 (4H, m), 7.18 (2H, m), 4.23 (1H, s), 3.60 (2H, t, J=5.5 Hz), 2.85 (1H, bs) and 2.55–2.44 (10H, bm).

(b) N-Methyl-N-4-(1H-2-methylimidazo[4,5-c]pyridinylmethyl)phenylsulphonyl-L-leucine-2-(4-benzhydryl-piperazin-1-yl)-ethyl ester.

N-Methyl-N-4-(1H-2-methylimidazo[4,5-c]pyridinylmethyl)-phenylsulphonyl-L-leucine (1.0 g, 2.33 mmol) was dissolved in DCM (25 ml) and treated with N-(3-dimethylaminopropyl)-N'-ethylcarbodiimide hydrochloride (446 mg, 2.33 mmol), 2-(4-benzhydryl-piperazine)-ethan-1-ol (688 mg, 2.33 mmol) and dimethylaminopyridine (284 mg, 2.33 mmol). The reaction was stirred at room temperature overnight. The reaction mixture was partitioned between DCM and saturated sodium bicarbonate. The organic layer was separated and washed with brine dried over magnesium sulphate, filtered and concentrated. The crude product was purified by column chromatography using silica gel and eluting with 3–10% methanol/DCM. Product containing fractions were combined and solvent removed to provide as a white foam N-methyl-N-4-(1H-2-methylimidazo[4,5-c]pyridinylmethyl)-phenylsulphonyl-L-leucine-2-(4-benzhydryl-piperazin-1-yl)-ethyl ester (660 mg, 40%).

$^1$H-NMR; δ (CDCl$_3$), 9.06 (1H, bs), 8.39 (1H, bs), 7.75 (2H, d, J=8.2 Hz), 7.40 (4H, d, J=7.7 Hz), 7.28–7.25 (4H,

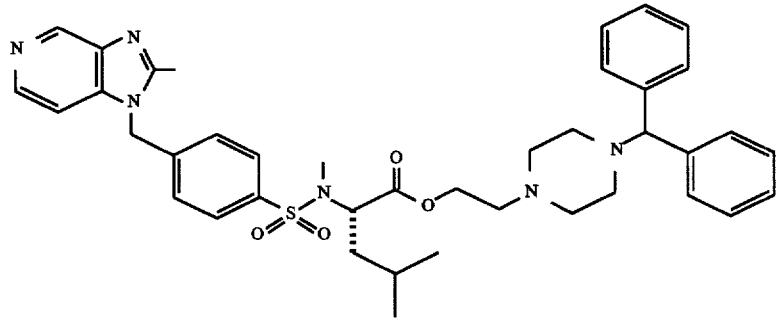

m), 7.19–7.12 (5H, m), 5.36 (2H, s), 4.65–4.62 (1H, m), 4.20 (1H, s), 3.98–3.91 (2H, m), 2.81 (3H, s), 2.57 (3H, s), 2.43–2.39 (8H, m), 1.87 (2H, bs), 1.62–1.54 (3H, m) and 0.93 (6H, t, J=2.5 Hz).

$^{13}$C-NMR; δ (CDCl$_3$), 170.8, 153.2, 142.5, 142.2, 142.1, 140.1, 139.8, 139.6, 139.4, 128.5, 128.3, 127.9, 127.0, 126.6, 104.6, 76.1, 62.0, 57.2, 56.2, 53.5, 51.7, 46.8, 38.1, 29.8, 24.4, 23.0, 21.2 and 14.0.

EXAMPLE 4

N-Methyl-N-4-(1H-2-methylimidazo[4,5-c]pyridinylmethyl)-phenylsulphonyl-L-leucine-3-(4-benzhydryl-piperazin-1-yl)-propyl ester.

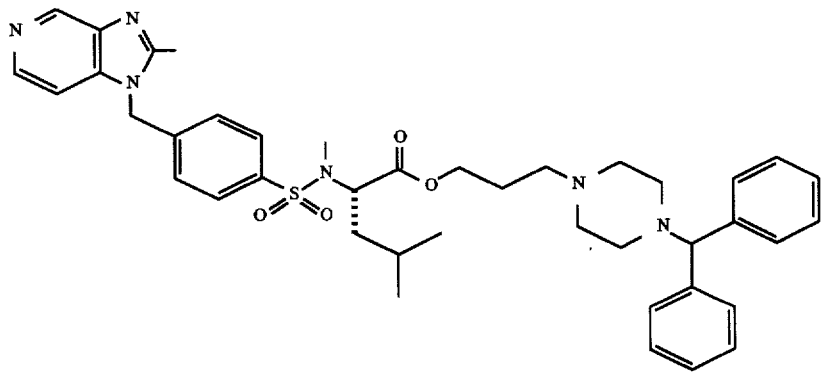

(a) 3-(4-Benzhydryl-piperazine)-propan-1-ol

Benzhydrylpiperazine (14.7 g, 58.3 mmol) was reacted with 3-bromopropanol (8.1 g, 58.3 mmol) using conditions described for example 3(a). 3-(4-Benzhydryl-piperazine)-propan-1-ol was produced as a colourless oil (12.4 g, 69%).

$^1$H-NMR; δ (CDCl$_3$), 7.48–7.25 (10H, m), 4.22 (1H, s), 3.78 (2H, t).2.69–2.35 (10H, m) and 1.72 (2H, m).

(b) N-Methyl-N-4-(1H-2-methylimidazo[4,5-c]pyridinylmethyl)phenylsulphonyl-L-leucine-3-(4-benzhydryl-piperazin-1-yl)-propyl ester.

N-Methyl-N-4-(1H-2-methylimidazo[4,5-c]pyridinylmethyl)phenylsulphonyl-L-leucine (1.0 g, 2.33 mmol) was reacted using conditions described for example 3(b) with 4-benzhydrylpiperazine-1-propanol (722 mg, 2.33 mmol) to provide N-methyl-N-4-(1H-2-methylimidazo[4,5-c]pyridinylmethyl)phenylsulphonyl-L-leucine-3-(4-benzhydryl-piperazin-1-yl)-propyl ester as a white foam (234 mg, 14%).

$^1$H-NMR; δ (CDCl$_3$), 9.01 (1H, s), 8.33 (1H, d, J=5.6 Hz), 7.71 (2H, d, J=8 Hz), 7.39 (4H, d, J=7.8 Hz), 7.38–7.09 (9H, m), 5.31 (2H, d, J=3 Hz), 4.61–4.58 (1H, m), 4.20 (1H, s), 3.87–3.77 (2H, m), 2.79 (3H, s), 2.54 (3H, s), 2.41 (8H, bs), 2.26 (2H, t, J=7.4 Hz), 1.63–1.55 (5H, m) and 0.99–0.90 (6H, m).

$^{13}$C-NMR; (CDCl$_3$), 170.9, 153.3, 142.6, 142.1, 142.0, 140.2, 139.8, 139.7, 139.3, 128.4, 128.2, 127.9, 126.9, 126.6, 104.7, 76.1, 63.4, 57.1, 54.7, 53.4, 51.8, 46.8, 38.1, 29.8, 25.8, 24.4, 23.0, 21.0 and 14.0.

EXAMPLE 5

N-Methyl-N-4-(1H-2-methylimidazo[4,5-c]pyridinylmethyl)-phenylsulphonyl-L-leucine-2-(4-benzhydyl-piperazin-1-yl)-ethylamide.

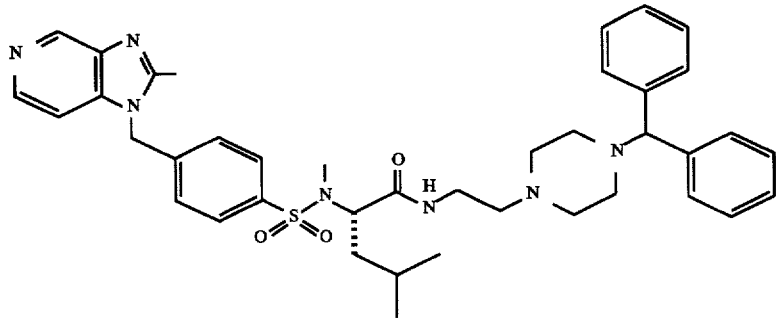

(a) (4-Benzyhydryl-piperazin-1-yl)-acetonitrile

Benzhyd.ylpiperazine (20 g, 79 mmol) was taken up in dry DCM (100 ml) and treated with triethylamine (11 ml, 79 mmol) and bromoacetonitrile (7.7 ml, 110 mmol). The reaction was stirred at room temperature overnight. The reaction mixture was partitioned between DCM and water. The organic layer was separated, washed with water, dried over magnesium sulphate and filtered. Solvent was removed under reduced pressure and the residue recrystallised from ethyl acetate to yield (4-benzhydryl-piperazin-1-yl)-acetonitrile as a white solid (19 g, 82%).

¹H-NMR; δ (CDCl₃), 7.48–7.44 (4H, m), 7.34–7.17 (6H, m), 4.27 (1H,m), 2.66–2.62 (4H,m), 2.49 (4H, bs).

(b) 2-(4-Benzhydryl-piperazine)-ethylamine (4-Benzyhydryl-piperazin-1-yl)-acetonitrile (19 g, 65 mmol) was taken up in dry THF (150 ml) and cooled in an ice/water bath. Lithium aluminium hydride (7.4 g, 1 95 mmol) was added slowly over 40 minutes and the reaction allowed to stir at room temperature overnight. The reaction mixture was treated dropwise with water (7.4 ml), 15% sodium hydroxide solution (7.4 ml) and more water (22.2 ml). The resulting precipitate was filtered off through sodium sulphate and silica. Removal of solvent under reduced pressure gave 2-(4-benzhydryl-piperazine)-ethylamine (19 g, 99%).

¹H-NMR; δ (CDCl₃), 7.45–7.41 (4H, m), 7.30–7.14 (6H, m), 4.22 (1H, s), 2.77 (2H, t, J=6.3 Hz), 2.47–2.27 (10H, m).

(c) N-Methyl-N-4-(1H-2-methylimidazo[4,5-c]pyridinylmethyl)phenylsulphonyl-L-leucine-2-(4-benzhydryl-piperazin-1-yl)-ethylamide.

N-Methyl-N-4-(1H-2-methylimidazo[4,5-c]pyridinylmethylphenylsulphonyl-L-leucine (435 mg, 1.01 mmol) was taken up in DMF (10 ml) and cooled in an ice/water bath. Hydroxybenzotriazole (177 mg, 1.31 mmol), N-(3-dimethylaminopropyl)-N'-ethylcarbodiimide hydrochloride (232 mg, 1.21 mmol) and 2-(4-benzhydryl-piperazine)-ethylamine (298 mg, 1.01 mmol) were added with stirring. The reaction was allowed to warm to ambient temperature and stirred for 48 hours. DMF was removed under vaccuum and the residue partitioned between ethyl acetate and sodium bicarbonate. The organic layer was separated and washed with brine before drying over sodium sulphate. The product was purified by flash chromatography on silica-gel, eluting with 10% methanol/DCM. Product containing fractions were combined and solvent removed to yield N-methyl-N-4-(1H-2-methylimidazo[4,5-c]-pyridinylmethyl)phenylsulphonyl-L-leucine-2-(4-benzhydryl-piperazin-1-yl)-ethylamide as a white foam (374 mg, 0.53 mmol).

¹H-NMR; δ (CDCl₃), 9.06 (1H, s), 8.39 (1H, d, J=5.6 Hz), 7.79 (2H, m), 7.41 (4H, d, J=7.6 Hz), 7.26 (3H, t, J=7.5 Hz), 7.15 (5H, m), 6.63 (1H, bs), 5.39 (2H, s), 4.32 (1H, t, J=7.5 Hz), 4.21 (1H, s), 3.23 (2H, dd, J=3.4, 5.0 Hz), 2.80 (3H, s), 2.59 (3H, s), 2.58–2.42 (10H, bm), 1.70 (1H, m), 1.32 (1H, m), 1.15 (1H, m), and 0.78 (6H, dd, J=5.0, 6.5 Hz).

¹³C-NMR; δ (CDCl₃), 169.6, 153.2, 142.8, 142.3, 142.2, 140.1, 139.9, 139.8, 139.6, 128.6, 128.4, 128.2, 128.1, 127.9, 126.9, 126.7, 126.6, 104.5, 76.2, 57.7, 56.1, 53.1, 53.0, 52.5, 51.8, 46.8, 37.1, 36.1, 169.6, 153.2, 142.8, 142.3, 142.2, 140.1, 139.9, and 14.0.

EXAMPLE 6

4-(8-Chloro-5,6-dihydro-11H-benzo[5,6]cyclohepta[1,2-b]-pyridin-11-ylidene)-1-(N-methyl-N-4-{1H-2-methylimidazo[4,5-c]pyridinylmethyl}-phenylsulphonyl-L-leucyl)-piperidine amide.

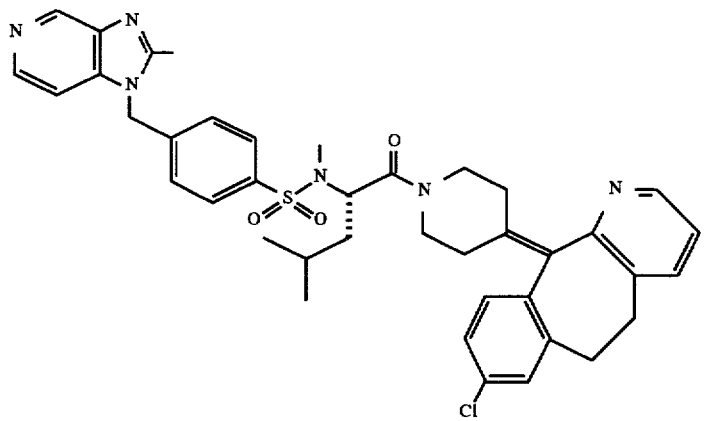

N-Methyl-N-4-(1H-2-methylimidazo[4,5-c]pyridinylmethylphenylsulphonyl-L-leucine (215 mg, 0.5 mmol) was converted to the pentafluorophenol derivative using the procedure described for example 1 (a). The pentafluorophenylester was dissolved in DCM (15 ml) and treated with 4-(8-chloro-5,6-dihydro-11H-benzo[5,6]-cyclohepta[1,2-b]pyridin-11-ylidene)piperidine (150 mg, 0.5 mmol). The reaction mixture was stirred overnight at room temperature before partitioning between DCM and saturated sodium bicarbonate. The organic layer was separated, washed with brine, dried over sodium sulphate and concentrated. The product was purified by column chromatography on silica gel and eluting with 3–5% methanol/VDCM. Product containing fractions were combined and solvent removed under reduced pressure to provide 4-(8-chloro-5,6-dihydro-11H-benzo[5,6]cyclohepta[1,2-b]-pyridin-11-ylidene)-1-(N-methyl-N-4-(1H-2-methylimidazo[4,5-c]pyridinylmethyl}-phenylsulphonyl-L-leucyl)-piperidine amide as a white foam (151 mg, 42%).

¹H-NMR; δ (CDCl₃), 9.01, 8.98 (1H, 2s), 8.39–8.34 (2H, m), 7.73–7.65 (2H, m), 7.46–7.41 (1H, m), 7.24–7.03 (7H, m), 5.40, 5.36 (2H, 2s), 4.94–4.89 (1H, m), 4.02–3.70 (2H, m), 3.52–2.94 (3H, m), 2.94–2.69 (2H, m), 2.89, 2.83 (3H, 2s), 2.65–2.04 (4H, m), 2.57, 2.54 (3H, 2s), 1.72–1.36 (2H, m), 1.27–0.96 (2H, m) and 0.88–0.79 (6H, m).

¹³C-NMR; δ (CDCl₃), 168.2, 156.6, 153.2, 146.7, 142.1, 142.0, 140.1, 139.8, 139.2, 137.6, 136.1, 134.9, 133.2, 133.1, 130.3, 129.0, 126.6, 126.2, 122.3, 104.6, 53.3, 53.1, 46.8, 46.3, 43.0, 37.2, 31.6, 31.5, 30.3, 24.8, 22.4, 22.2, 21.9 and 13.9.

EXAMPLE 7

4-(8-Chloro-5,6-dihydro-11H-benzo[5,6]cyclohepta
[1,2-b]-pyridin-11-ylidene)-1-(N-methyl-N-4-{1H-2-
methylimidazo[4,5-c]pyridinylmethyl}-
phenylsulphonyl-L-leucinol)-piperidine carbamate.

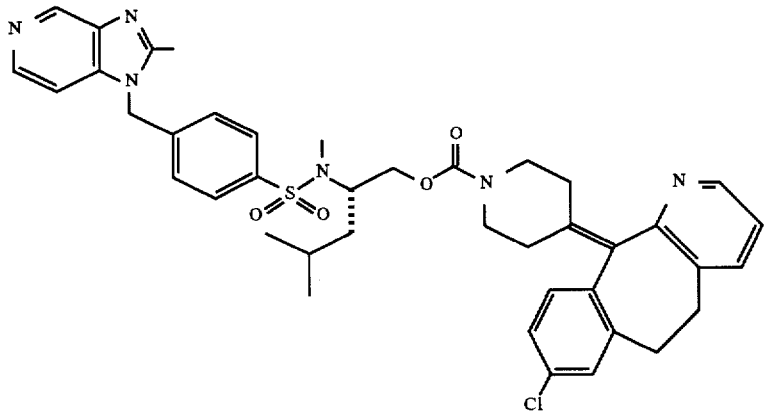

N-Methyl-N-4-(1H-2-methylimidazo[4,5-c]
pyridinylmethyl)-phenylsulphonyl-L-leucinol (200 mg, 0.48 mmol) was stirred in acetonitrile (4 ml) at room temperature and treated with N,N'-disuccinimidyl carbonate (185 mg, 0.72 mmol) and triethylamine (200 μl, 1.44 mmol). After 4 hours solvent was removed under reduced pressure and the solvent partitioned between ethyl acetate and saturated sodium bicarbonate. The organic layer was separated, washed with brine, dried over sodium sulphate, filtered and concentrated to yield a white foam. A solution of this mixed carbonate in DCM (2 ml) was added to a solution of 4-(8-chloro-5,6-dihydro-11H-benzo[5,6]-cyclohepta[1,2-b] pyridin-11-ylidene)piperidine (170 mg, 0.57 mmol) and triethylamine (100 μl, 0.72 mmol). The reaction was stirred at room temperatue overnight before diluting with DCM and partitioning with saturated sodium bicarbonate. The organic layer was separated, washed with brine, dried over sodium sulphate, filtered and solvent removed. The crude product was purified by MPLC using a siica gel column and a gradient elution of 6.5–7.5% methanol/DCM in 40 minutes with a flow rate of 70 ml/minute. Product contaning fractions were combined and solvent removed to yield 4-(8-chloro-5,6-dihydro-11H-benzo[5,6]-cyclohepta[1,2-b]-pyridin-11-ylidene)-1-(N-methyl-N-4-{1H-2-methylimidazo[4,5-c]-pyridinylmethyl}-phenylsulphonyl-L-leucinol)-piperidine carbamate as a white foam (304 mg, 87%). $^1$H-NMR; δ (CDCl$_3$), 9.04 (1H, s), 8.37 (2H, m), 7.77 (2H, d, J=8.1 Hz), 7.42 (1H, d, J=7.3 Hz), 7.06–7.15 (7H, m), 5.38 (2H, s), 4.20–4.35 (1H, m), 3.90–4.10 (2H, m), 3.70–3.90 (2H, m), 3.07–3.47 (4H, m), 2.70–3.06 (2H, m), 2.65 (3H, s), 2.58 (3s), 2.25–2.55 (4H, m), 1.12–1.46 (3H, m) and 0.75–0.85 (6H, bd).

$^{13}$C-NMR; δ (CDCl$_3$), 167.6, 157.2, 154.8, 153.2, 149.6, 146.7, 142.3, 140.9, 140.3, 140.0, 139.6, 137.8, 137.4, 137.3, 134.4, 133.3, 133.0, 130.5, 129.0, 128.0, 126.8, 126.2, 122.2, 104.6, 64.2, 54.4, 46.9, 45.0, 37.9, 31.8, 31.6, 30.7, 30.5, 28.3, 24.6, 22.9, 22.3 and 13.9.

EXAMPLE 8

(E)-3-(6-[Pyrrolidino-1-{4-tolyl}prop-1E-enyl]-2-
pyridyl)acrylic acid, N-methyl-N-4-(1H-2-
methylimidazo[4,5-c]pyridinylmethyl)-
phenylsulphonyl-L-leucyl ester.

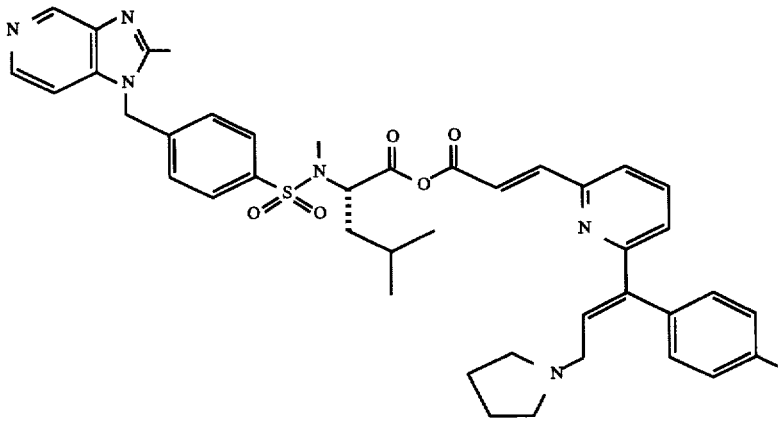

N-Methyl-N-4-(1H-2-methylimidazo[4,5-c]
pyridinylmethylphenylsulphonyl-L-leucinol (253 mg, 0.61 mmol) was dissolved in DCM (10 ml) and treated with N-(3-dimethylaminopropyl)-N'-ethylcarbodiimide hydrochloride (140 mg, 0.73 mmol), (E)-3-(6-[pyrrolidino-1-{4-tolyl}prop-1E-enyl]-2-pyridyl)acrylic acid (acrivastine) 0.61 mmol) and dimethylaminopyridine (3 mg). The reaction was stirred at room temperature overnight and directly added to a silica gel column for purification. Elution with 5% methanol/DCM and removal of solvent under reduced pressure yielded (E)-3-(6-[pyrrolidino-1-{4-tolyl}prop-1E-enyl]-2-pyridyl)acrylic acid, N-methyl-N-4-(1H-2-methylimidazo[4,5-c]pyridinylmethyl)-phenylsulphonyl-L-leucyl ester as a pale brown foam (199 mg, 44%).

$^1$H-NMR; δ (CDCl$_3$), 9.02 (1H, d, J=0.7 Hz), 8.33 (1H, d, J=5.7 Hz), 7.82 (2J=8.4 Hz), 7.59 (1H, d, J=2.8 Hz), 7.58 (1H, t, J=3.6 Hz), 7.10 (11H, m), 5.26 (2H, s), 4.38 (1H, m), 4.13 (1H, dd, J=11.9, 7.4 Hz), 4.04 (1H, dd, J=11.8, 4.8 Hz), 3.26 (2H, d, J=6.8 Hz), 2.79 (3H, s), 2.59 (4H, m), 2.50 (3H, s), 2.40 (3H, s), 1.82 (4H, m), 1.51 (1H, m), 1.36 (1H, m), 1.25 (1H, m), 0.95 (3H, d, J=2.8 Hz) and 0.93 (3H, d, J=2.9 Hz).

$^{13}$C-NMR; δ (CDCl$_3$), 166.3, 158.2, 153.3, 151.6, 144.2, 142.2, 142.1, 140.4, 140.2, 139.8, 139.6, 137.3, 137.2, 134.8, 129.6, 129.3, 128.1, 126.8, 123.2, 123.1, 121.3, 104.6, 64.1, 54.7, 54.1, 54.0, 46.7, 38.0, 28.6, 24.4, 23.5, 23.1, 22.0, 21.2 and 13.9.

EXAMPLE 9

(4-Benzhydrylpiperazin-1-yl)-acetic acid, N-methyl-N-4-(1H-2-methylimidazo[4,5-c]-pyridinylmethyl)-phenylsulphonyl-L-leucyl ester.

(a) (4-Benzhydrylpiperazin-1yl)-acetic acid, methyl ester.

Methylbromoacetate (2.75 g, 18 mmol) was added dropwise to a solution of benzhydrylpiperazin (4.5 g, 18 mmol) in THF (150 ml). The reaction was stirred for 30 minutes at room temperature and a white precipitate formed. THF was removed under reduced pressure and the residue partitioned between ethyl acetate and saturated sodium bicarbonate solution. The organic layer was washed with saturated sodium bicarbonate solution and water before drying over magnesium sulphate, filtration and removal of solvent to leave (4-benzhydrylpiperazin-1-yl)-acetic acid, methyl ester as a pale brown oil (2.80 g, 48%).

$^1$H-NMR; δ (CDCl$_3$) 7.42 (4H, d), 7.37 (4H, m), 7.18 (2H, m), 4.25 (1H, s), 3.70 (3H, s), 3.24 (2H, s), 2.66 (4H, bs) and 2.48 (4H, bs).

(b) (4-Benzhydrylpiperazin-1-yl)-acetic acid.

An aqueous solution of lithium hydroxide (486 mg, 11.58 mmol, 2 ml water) was added to a solution of (4-benzhydrylpiperazin-1-yl)-acetic acid, methyl ester (2.5 g, 7.72 mmol) in a 5:1 mixture of THF/water (20 ml). The reaction was stirred at room temperature overnight. THF was removed under reduced pressure. The reaction mixture was partitioned between ethyl acetate and water. The aqueous layer was separated and neutralised to pH7 with 1M HCl. A white gelatinous precipitate of (4-benzhydrylpiperazin-1-yl)-acetic acid was formed which was collected by filtration and dried (1.10 g, 46%).

$^1$H-NMR; δ (CDCl$_3$), 7.45 (4H, d, J 7.5 Hz), 7.29 (4H, t, J=7.4 Hz), 7.21 (2H, m), 4.39 (1H, s), 3.60 (2H, s), 3.33 (4H, bs), 2.67 (4H, bs).

(c) (4-Benzhydrylpiperazin-1-yl)-acetic acid, N-methyl-N-4-(1H-2-methylimidazo[4,5-c]-pyridinylmethyl)-phenylsulphonyl-L-leucyl ester.

N-Methyl-N-4-(1H-2-methylimidazo[4,5-c]pyridinylmethyl)-phenylsulphonyl-L-leucinol (800 mg, 1.92 mmol), (4-benzhydrylpiperazin-1-yl)-acetic acid (595 mg, 1.92 mmol), N-(3-dimethylaminopropyl)-N'-ethylcarbodiimide hydrochloride (368 mg, 1.92 mmol) and dimethylaminopyridine (235 mg, 1.92 mmol) were dissolved in DCM (30 ml) and allowed to stand at room temperature overnight. The reaction mixture was partitioned between DCM and brine. The organic layer was separated, dried over magnesium sulphate, filtered and solvent removed to leave a white foam. The product was isolated by chromatography on silica-gel using 4% methanol/DCM as eluant. Product containing fractions were combined and solvent removed to provide (4-benzhydrylpiperazin-1-yl)-acetic acid, N-methyl-N-4-(1H-2-methylimidazo[4,5-c]-pyridinylmethyl)-phenylsulphonyl-L-leucyl ester as a white foam (510 mg, 38%).

$^1$H-NMR; δ (CDCl$_3$), 9.04 (1H, s), 8.38 (1H, d, J=5.5 Hz), 7.78 (2H, d, J=8.3 Hz), 7.28 (4H, m), 7.45 (4H, d), 7.15 (5H,

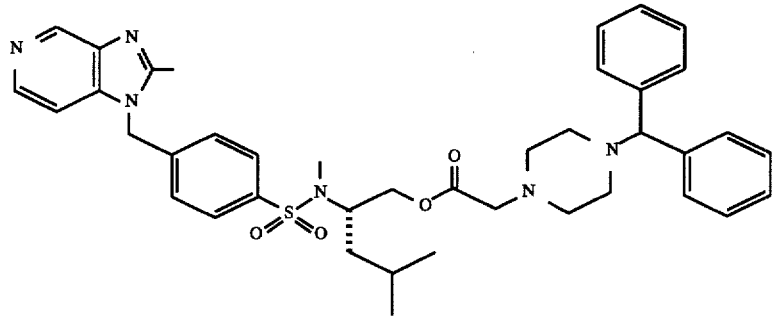

m), 5.42 (2H, s), 4.27 (1H, m), 4.23 (1H, s) 4.03 (1H, dd, J=11.7 and 8.2 Hz), 3.96 (1H, dd, J=11.7 and 4.5 Hz), 3.19 (2H, d, J=2.1 Hz), 2.60 (3H, s), 2.59 (4H, bs), 2.59 (3H, s), 2.45 (4H, bs), 1.37 (1H, m), 1.18 (2H, t, J=7.0 Hz) and 0.86 (6H, m).

$^{13}$C-NMR; δ (CDCl$_3$), 170.0, 153.2, 142.3, 142.2, 140.4, 140.2, 139.6, 128.4, 128.1, 127.9, 126.9, 126.7, 104.6, 76.1, 63.1, 58.9, 53.7, 53.1, 51.6, 46.8, 37.6, 28.2, 24.4, 22.9, 22.1 and 14.0.

EXAMPLE 10

N-Methyl-N-(S)-(1-[4-benzhydrylpiperazin-1-yl]-methyl-3-methyl-butyl)-N-4-(1H-2-N-methylimidazo[4,5c]pyridinylmethyl)-phenylsulphonamide.

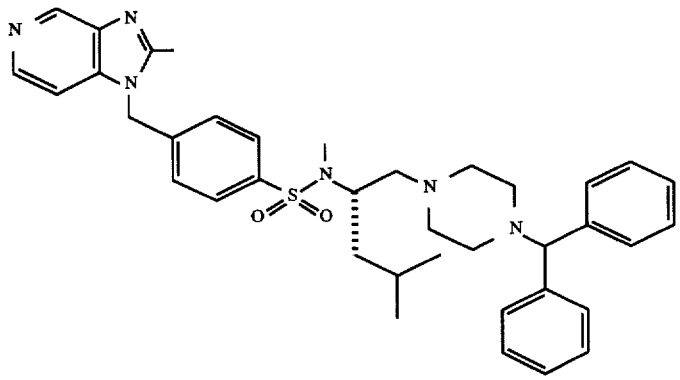

(a) N-Methyl-N-(S)-(1-methyl-O-methanesulphonate-3-methyl-butyl)-N-4-(1H-2-methylimidazo[4,5c]-pyridinylmethyl)-phenylsulphonamide.

N-Methyl-N-4-(1H-2-methylimidazo[4,5c]pyridinylmethyl)-phenylsulphonyl-L-leucinol (890 mg, 2.1 mmol) was dissolved in THF (30 ml) and treated with triethylamine (0.33 ml, 2.5 mmol) and methane sulphonylchloride. After 30 minutes solvent was removed under reduced pressure and the residue partitioned between DCM and saturated sodium bicarbonate solution. The organic layer was separated, washed with brine, dried over sodium sulphate, filtered and solvent removed to leave N-Methyl-N-(S)-(1-methyl-O-methanesulphonate-3-methyl-butyl)-N-4-(1H-2-methylimidazo[4,5c]-pyridinylmethyl)-phenylsulphonamide as a yellow foam (1.02 g, 96%).

$^1$H-NMR; δ (CDCl$_3$), 9.05 (1H, s), 8.40 (1H, d, J 5.7 Hz), 7.81 (2H, d, J=8.3 Hz), 7.26 (1H, d, J=6.5 Hz), 7.16 (2H, d, J 8.2 Hz), 5.44 (2H, s), 4.34–4.30 (1H, m), 4.06–3.98 (2H, m), 2.91 (3H, s), 2.72 (3H, s), 2.64 (3H, s), 1.54–1.50 (1H, m), 1.43–1.34 (1H, m), 1.24–1.18 (1H, m) and 0.91 (6H, t, J=2.6 Hz).

(b) N-Methyl-N-(S)-(1-[4-benzhydrylpiperazin-1-yl]-methyl-3-methyl-butyl)-N-4-(1H-2-methylimidazo[4,5c]pyridinylmethyl)-phenylsulphonamide.

N-Methyl-N-(S)-(1-methyl-O-methanesulphonate-3-methyl-butyl)-N-4-(1H-2-methylimidazo[4,5c]-pyridinylmethyl)-phenylsulphonamide (300 mg, 0.61 mmol) in THF (20 ml) was added to a stirred solution of 1-benzhydryl-piperazine (306 mg, 1.21 mmol) and triethylamine (0.1 ml, 0.71 mmol) in THF (30 ml). The reaction mixture was heated under reflux for 3 days. Solvent was removed under reduced pressure and the residue partitioned between DCM and water. The organic layer was separated, dried over sodium sulphate and concentrated. Purification by column chromatography on silica gel, eluting with 5% methanol/DCM yielded N-methyl-N-(S)-(1-[4-benzhydrylpiperazin-1-yl]-methyl-3-methyl-butyl)-N-4-(1H-2-methylimidazo[4,5c]pyridinylmethyl)-phenylsulphonamide as a white foam (234 mg, 59%).

$^1$H-NMR; δ (CDCl$_3$), 9.03 (1H, s), 8.34 (1H, d, J=5.5 Hz), 7.90–7.29 (2H, m) (4H, m), 7.30–6.99 (9H, m), 5.30 (2H, s), 4.21–4.06 (1H, m), 4.13 (1H, s), 2.55 (3H, s), 2.53 (3H, s), 2.51–2.07 (10H, m), 1.59–1.40 (1H, m), 1.33–1.2H, m) and 0.82 (6H, d, J=6.6 Hz).

$^{13}$C-NMR; δ (CDCl$_3$), 153.2, 142.5, 142.0, 141.8, 140.6, 140.1, 139.7, 139.2, 128.3, 128.2, 127.6, 126.7, 126.4, 104.6, 76.1, 60.0, 53.6, 52.3, 51.7, 46.6, 39.7, 27.6, 24.4, 23.1, 21.7 and 13.8.

EXAMPLE 11

N-Methyl-N-(S)-(1-aminomethyl-[{4-benzhydrylpiperazin-1-yl}-acetamidel-3-methyl-butyl)-N-4-(1H-2-methylimidazo[4,5c]-pyridinylmethyl)-phenylsulphonamide.

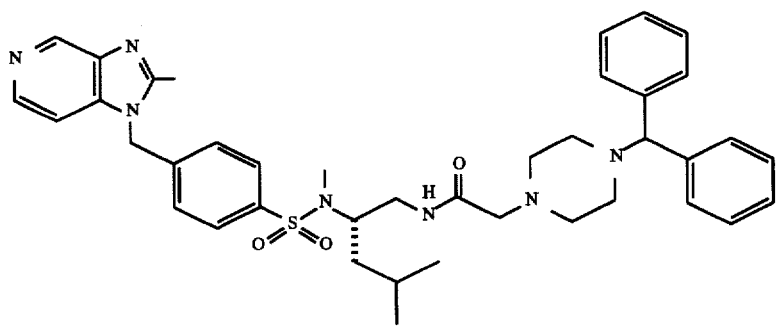

(a) N-Methyl-N-(S)-(1-azidomethyl-3-methyl-butyl)-N-4-(1H-2-methylimidazo[4,5c]-pyridinylmethyl)-phenylsulphonamide.

N-Methyl-N-(S)-(1-methyl-O-methanesulphonate-3-methyl-butyl)-N-4-(1H-2-methylimidazo[4,5c]-pyridinylmethyl)-phenylsulphonamide (850 mg, 1.7 mmol) was dissolved in DMF (15 ml), treated with sodium azide (1 44 mg, 2.2 mmol) and heated at 100° C. for 6 hours. The reaction mixture was partitioned between diethylether and brine. The organic layer was separated, dried over sodium sulphate, filterd and solvent removed to yield N-methyl-N-(S)-(1-azidomethyl-3-methyl-butyl)-N-4-(1H-2- methylimidazo[4,5c]-pyridinylmethyl)-phenylsulphonamide as a colourless oil (476 mg, 63%).

¹H-NMR; δ (CDCl₃), 9.02 (1H, d, J=2.9 Hz), 8.36 (1H, m), 7.79 (2H, m), 7.14 (3H, m), 5.39 (2H, s), 4.12–4.06 (1H, m), 3.20–3.16 (2H, m), 2.68 (3H, s), 2.56 (3H, S), 1.51–1.42 (1H, m), 1.33–1.25 (1H, m), 1.19–1.15 (1H, m), 0.86 (3H, d, J =3.3 Hz) and 0.84 (3H, d, J=3.4 Hz.

(b) N-Methyl-N-(S)-(1-aminomethyl-3-methyl-butyl)-N-4-(1H-2-methylimidazo[4,5c]-pyridinylmethyl)-phenylsulphonamide A solution of N-methyl-N-(S)-(1-azidomethyl-3-methyl-butyl)-N-4-(1H-2-methylimidazo[4,5c]-pyridinylmethyl)-phenylsulphonamide (310 mg, 0.70 mmol) in ethanol (25 ml) was treated with palladium on charcoal catalyst (50 mg, 10% Pd/C) and stirred under an atmosphere of hydrogen for 90 minutes. The catalyst was removed by filtration and solvent evaporated under reduced pressure to yield N-Methyl-N-(S)-(1-aminomethyl-3-methyl-butyl)-N-4-(1H-2-methylimidazo[4,5c]-pyridinylmethyl)-phenylsulphonamide as a white foam (285 mg, 98%).

¹H-NMR; δ (CDCl₃), 9.04 (1H, s), 8.37 (1H, d, J=5.6 Hz), 7.81 (2H, d, J=8.3 Hz), 7.16 (2H, d, J=8.4 Hz), 7.13 (1H, d, J=5.9 Hz), 5.40 (2H, s), 3.96–3.91 (1H, m), 2.76 (1H, dd, J=13.7, 4.44 Hz), 2.67 (3H, s), 2.64 (1H, dd, J=13.7, 4.1 Hz), 2.59 (3H, s), 1.32–1.27 (1H, m), 1.17–1.12 (1H, m), 0.97–0.92 (1H, m), and 0.74 (6H, t, J=6.2 Hz).

¹³C-NMR; δ (CDCl₃), 152.5, 142.2, 142.1, 128.2, 126.8, 104.6, 57.8, 46.4, 42.3, 38.5, 28.0, 24.6, 22.7 and 15.5.

(c) N-Methyl-N-(S)-(1-aminomethyl-[{4-benzhydrylpiperazin-1-yl}-acetamide]-3-methyl-butyl)-N-4-(1H-2-methylimidazo[4,5c]-pyridinylmethyl)-phenylsulphonamide.

A solution of (4-benzhydrylpiperazin-1-yl)-acetic acid (180 mg, 0.58 mmol), pentafluorophenol (106 mg, 0.58 mmol) and N-(3-dimethylaminopropyl)-N'-ethylcarbodiimide hydrochloride (111 mg, 0.58 mmol) in DCM (15 ml) was stirred at room temperature for 30 minutes. A solution of N-methyl-N-(S)-(1-aminomethyl-3-methyl-butyl)-N-4-(1H-2-methylimidazo[4,5c]-pyridinylmethyl)-phenylsulphonamide (200 mg, 0.48 mmol) in DCM (5 ml) was added to the reaction mixture which was stirred at room temperature overnight. The reaction mixture was partitioned between DCM and 1 M sodium carbonate. The organic layer was separated and washed with brine before drying over magnesium sulphate. Filtration and concentration gave a colourless oil. The product was purified by column chromatography on silica-gel eluting with 5% methanol/DCM. Product containing fractions were combined and solvent removed to yield N-methyl-N-(S)-(1-aminomethyl-[{4-benzhydrylpiperazin-1-yl)-acetamide]-3-methyl-butyl)-N-4-(1H-2-methylimidazo[4,5c]-pyridinylmethyl)-phenylsulphonamide as a white solid (45 mg, 13%).

¹H-NMR; δ (CDCl₃), 9.03 (1H, s), 8.36 (1H, d, J=5.5 Hz), 7.56 (2H, d, J=8.36 Hz), 7.56 (1H, t, J=7.56 Hz), 7.39 (4H, d, J=7.3 Hz), 7.26–7.21 (4H, m), 7.15–7.10 (5H, m), 5.36 (2H, s), 4.23 (1pH, s), 4.04–4.01 (1pH, m), 3.31–3.24 (1H, m), 3.21–3.05 (1H, m), 3.02 (2H, d, J=5.4 Hz), 2.63 (3H, s), 2.59 (4H, bm), 2.56 (3H, s), 2.54–2.40 (4H, m), 1.23–1.18 (1H, m), 1.15–1.09 (1H, m), 0.98–0.92 (1H, m), 0.72 (3H, d, J=3.5 Hz), and 0.71 (3H, d, J=3.6 Hz).

¹³C-NMR; δ (CDCl₃), 171.1, 153.3, 142.7, 142.2, 142.1, 140.3, 140.2, 139.8, 139.6, 128.4, 128.0, 127.8, 126.9, 126.8, 104.6, 76.0, 61.4, 54.8, 53.9, 51.9, 46.8, 39.6, 38.8, 27.8, 24.6, 22.6, 22.6 and 14.0.

EXAMPLE 12

N-(S)-(4-Methyl-2-{methyl-[4-(1H-2-methyl-imidazo[4,5-c]pyridin-1-ylmethyl)-phenylsulphonyl]-amino)-pentyl)-3-[6-(3-pyrrolidin-1-yl-p-tolyl-prop-1E-enyl)-pyridin-2-yl] acrylamide.

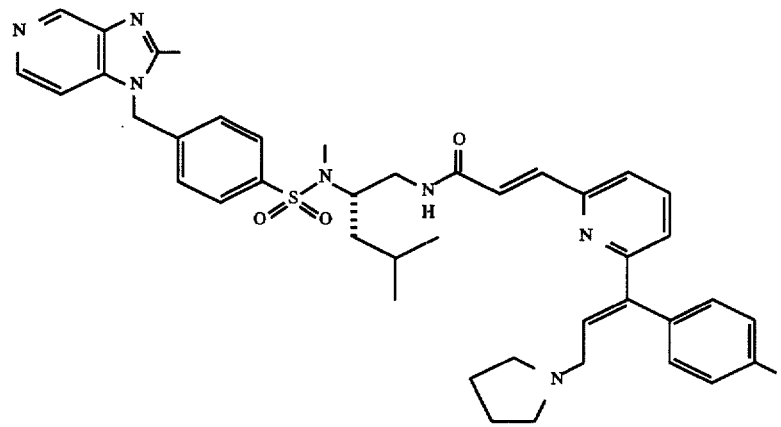

Using a procedure similar to that described for example 11, N-methyl-N-(S)-(1-aminomethyl-3-methyl-butyl)-N-4-(1H-2-methylimidazo[4,5c]-pyridin-1-ylmethyl)-benzenesulphonamide (1.00 g, 2.41 mmol) was coupled to (E)-3-(6-[pyrrolidino-1-{4-tolyl)prop-1E-enyl]- 2-pyridyl) acrylic acid (0.92 g, 2.65 mmol) to provide N-(S)-(4-methyl-2-{methyl-[4-(1H-2-methyl-imidazo[4,5-c]pyridin-1-ylmethyl)-benzenesulphonyl]-amino)-pentyl)-3-[6-(3-pyrrolidin-1-yl-p-tolyl-prop-1E-enyl)-pyridin-2-yl] acrylamide as a pink solid (106 mg, 4.5%).

¹H-NMR; δ (CDCl₃), 9.00 (1H, s), 8.33 (1H, d, J=5.5 Hz), 7.91 (2H, d, J=8.3 Hz), (1H, m), 7.50 (3H, m), 7.27 (1H, d, J=7.7 Hz), 7.20 (1H, d, J=7.5 Hz), 7.16 (3H, d, J=8.3 Hz), 7.09 (3H, d, J=7.9 Hz), 7.03 (1 H, d, J=5.6 Hz), 6.83 (1H, d, J=7.7 Hz), 5.22 (2H, s), 4.16 (1H, m), 3.61 (2H, d, J=7.0 Hz), 3.30 (2H, m), 2.99 (4H, br m), 2.78 (3H, s), 2.49 (3H, s), 2.43 (3H, s), 1.97 (4H, br m), 1.54 (1 H, m), 1.29 (2H, m) and 0.87 (6H, t, J=6.2 Hz).

¹³C-NMR; δ (CDCl₃), 166.0, 155.8, 153.4, 152.4, 144.8, 142.0, 141.8, 140.3, 140.2, 139.7, 139.4, 138.2, 137.6, 137.5, 137.4, 133.2, 129.6, 129.6, 129.3, 128.2, 127.0, 124.1, 122.4, 104.8, 55.1, 54.4, 54.2, 53.7, 53.6, 46.8, 40.6, 39.0, 28.0, 24.5, 23.3 and 13.9.

EXAMPLE 13

2-[4-(8-Chloro-5,6-dihydro-11H-benzo[5,6]
cyclohepta[1,2-b]pyridin-11-ylidene)-piperidin-1-yl]
-N-(4-methyl-2-{methyl-[4-(1H-2-methylimidazo[4,
5-c]pyridin-1-ylmethyl)-phenylsulphonyl]-amino}-
pentyl)-acetamide.

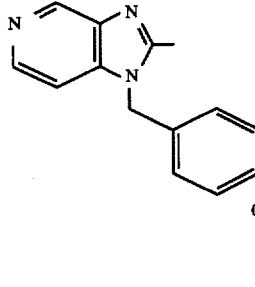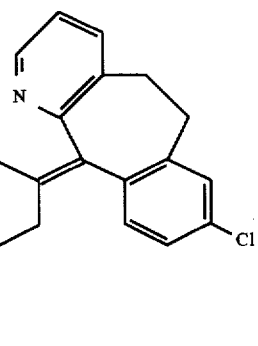

(a) Methyl-[4-{8-chloro-5,6-dihydro-11H-benzo[5,6]
cyclohepta[1,2-b]pyridin-11ylidene}-piperidin1-yl]acetate Methylbromoacetate (0.17 ml, 1.77 mmol) was added dropwise to a solution of 4-{8-chloro-5,6-dihydro-11H-benzo[5,6]cyclohepta[1,2-b]pyridin-11-ylidene}-piperidine (0.50 g, 1.61 mmol) and triethylamine (0.45 ml, 3.22 mmol) in THF (15 ml) under an inert atmosphere. The reaction was left to stir for 18 hours. THF was removed under reduced pressure and the product purified by column chromatography on silica gel, eluting with 5% methanol/DCM. Product containing fractions were combined and solvent removed under reduced pressure to yield methyl-[4-{8-chloro-5,6-dihydro-11H-benzo[5,6]cyclohepta[1,2-b]pyridin-11-ylidene}-piperidin-1-yl]acetate as an orange solid (550 mg, 90%).

$^1$H-NMR; δ (CDCl$_3$), 8.40 (1H, m), 7.42 (1H, m), 7.09 (4H, m), 3.71 (3H, s), 3.37 (2H, m), 3.24 (2H, s), 2.79 (4H, m), 2.57 (1 H, m), 2.47 (1 H, m), and 2.37 (4H, m).

$^{13}$C-NMR; δ (CDCl$_3$), 170.9, 157.5, 146.6, 139.5, 138.1, 137.7, 137.2, 133.4, 133.0, 132.7, 130.8, 128.9, 126.0, 122.1, 59.3, 54.6, 51.7, 31.8, 31.4, 30.8 and 30.5.

(b) 4-{8-chloro-5,6-dihydro-11H-benzo[5,6]cyclohepta[1,2-b]pyrid-11-ylidene}-piperidin-1-ylacetic acid Using the procedure described for example 9(b), methyl-[4-{8-chloro-5,6-dihydro-11H-benzo[5,6]cyclohepta[1,2-b]pyridin-11-ylidene}-piperidin-1-yl]acetate (460 mg, 1.1 9 mmol) was hydrolysed to provide 4-{8-chloro-5,6-dihydro-11H-benzo[5,6]-cyclohepta-[1,2-b]-pyridin-11-ylidene}piperidin-1-ylacetic acid as a yellow glass (440 mg, 99%).

$^1$H-NMR; δ (MeOD), 8.31 (1H, d, J=4.9 Hz), 7.65 (1H, d, J=7.7 Hz), 7.2 (4H, m), (2H, m), 3.31 (2H, s), 3.05 (2H, s), 2.86 (2H, m), 2.55 (4H, m), 2.46 (1H, m) 2.31 (1H, m).

$^{13}$C-NMR; δ (MeOD), 158.4, 147.0, 141.2, 139.5, 138.4, 138.0, 135.9, 134.2, 131.7, 130.3, 127.0, 124.1, 62.3, 55.2, 55.2, 32.6, 32.0, 30.6 and 30.5.

(c) 2-[4-(8-Chloro-5,6-dihydro-11H-benzo[5,6]cyclohepta [1,2-b]pyridin-11-ylidene)-piperidin-1-yl]-N-(4-methyl-2-{methyl-[4-(1H-2-methylimidazo[4,5-c]pyridin-1-ylmethyl)-phenylsulphonyl]-amino}-pentyl)-acetamide.

Using a procedure similar to that described for example 11(c), 4-{8-chloro-5,6-dihydro-11H-benzo[5,6]cyclohepta[1,2-]pyridin-11-ylidene}piperidin-1-ylacetic acid (445 mg, 1.19 mmol) was coupled to N-methyl-N-(S)-(1-aminomethyl-3-methyl-butyl)-N-4-(1H-2-methylimidazo[4,5-c]pyridinylmethyl)-phenylsulphonamide (459 mg, 108 mmol) to provide 2-[4-(8-chloro-5,6-dihydro-11H-benzo[5,6]cyclohepta[1,2-b]pyridin-11-ylidene)-piperidin-1-yl]-N-(4-methyl-2-{methyl-[4-(1H-2-methylimidazo[4,5-c]pyridin-1-ylmethyl)-phenylsulphonyl]-amino)-pentyl)-acetamide as an off white solid (264 mg, 32%).

$^1$H-NMR; δ (CDCl$_3$), 8.98 (1H, s), 8.31 (2H, m), 7.70 (2H, d, J=8.3 Hz), 7.66 (1H, dd, J=10.2, 5.0 Hz), 7.35 (1H, d, J=7.1 Hz), 7.05 (7H, m), 5.33 (2H, s), 4.00 (1H, m), 3.25 (4H, m), 2.94 (2H, m), 2.74 (4H, m), 2.60 (3H, d, J=1.1 Hz), 2.53 (3H, s), 2.52 (1H, m), 2.43 (1H, m), 2.28 (4H, m), 1.12 (2H, m), 0.88 (1H, m) and 0.66 (6H, m).

$^{13}$C-NMR; δ (CDCl$_3$), 171.3, 171.2, 157.5, 153.2, 146.6, 142.2, 142.1, 140.4, 140.3, 140.1, 139.8, 139.6, 139.5, 138.1, 138.0, 137.7, 137.3, 133.4, 132.9, 132.6, 130.8, 128.9, 128.0, 126.8, 126.0, 122.1, 104.6, 61.3, 55.5, 55.4, 54.9, 54.7, 46.8, 39.7, 39.6, 38.9, 38.9, 31.8, 31.4, 30.9, 30.8, 27.8 and 22.6.

EXAMPLE 14

N-[1-{(4-Chlorobenzhydryl)-piperazin-1-ylmethyl}-
3-methyl-butyl]-N-methyl-4-(1H-2-methylimidazo
[4,5-c]pyridin-1-ylmethyl)-phenylsulphonamide.

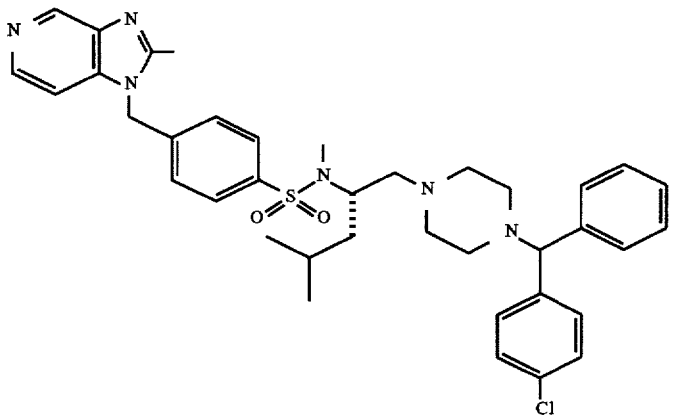

Following the procedure described for example 10, N-methyl-N-(S)-(1-methyl-O-methanesuiphonate-3-methyl-butyl)-N-4-(1H-2-methylimidazo[4,5c]-pyridinylmethyl)-phenylsulphonamide (300 mg, 0.61 mmol) was reacted with 4-chlorobenzhydrylpiperazine (350 mg, 1.22 mmol) to provide N-[1-{(4-chlorobenzhydryl)-piperazin-1-ylmethyl}-3-methyl-butyl]-N-methyl-4-(1H-2-methylimidazo[4,5-c]pyridin-1-ylmethyl)-phenylsulphonamide as a white solid (39 mg, 9%).

$^1$H-NMR; δ (CDCl$_3$), 9.08 (1H, s), 8.41 (1H, dd, J=1.3, 5.6 Hz), 7.91 (2H, dd, J8.4 Hz), 7.36–7.08 (12H, m), 5.40 (2H, s), 4.16 (2H, m), 2.61 (3H, s), 2.58 (3H, s), 2.42 (8H, brs), 2.23 (1H, m), 2.15 (1H, m), 1.50 (1H, m), 1.25 (2H, m), and 0.86 (6H, m).

$^{13}$C-NMR; (CDCl$_3$), 153.3, 142.2, 140.9, 140.2, 139.9, 139.2, 132.5, 129.2, 128.6, 128.5, 127.8, 127.2, 126.5, 104.6, 75.5, 60.1, 53.6, 52.2, 51.7, 46.8, 39.6, 27.7, 24.5, 23.3, 21.8 and 14.0.

EXAMPLE 15

N-Methyl-N-4-(1H-2-methylimidazo[4,5-c]pyridinylmethyl)phenylsulphonyl-L-leucine-2-(4-{8-chloro-5,6-dihydro-11H-benzo[5,6]cyclohepta[1,2-b]pyridin-11-ylidene}piperidin-1-yl)-ethyl ester.

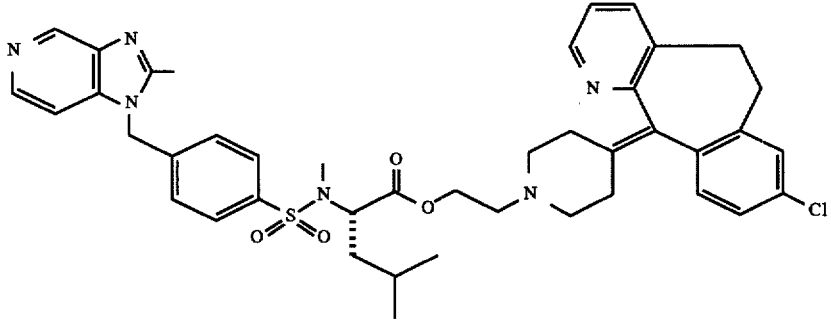

(a) Ethyl-(4-{8-chloro-5,6-dihydro-11H-benzo[5,6]cyclohepta[1,2-b]-pyridin-11-ylidene}piperidin1-yl)acetate 2-Bromoethyl acetate (267 mg, 1.6 mmol) was added dropwise to a stirred solution of 4-{8-chloro-5,6-dihydro-11H-benzo[5,6]cyclohepta[1,2-b]pyridin-11-ylidene}piperidine (500 mg, 1.6 mmol) in THF (12 ml) and the reaction stirred at room temperature overnight. THF was removed under reduced pressure and the residue partitioned between ethylacetate and saturated sodium bicarbonate solution. The organic layer was separated, dried over magnesium sulphate, filtered and solvent removed to leave a white solid. The product was purified by column chromatography on silica gel eluting with 5% methanol/DCM. Product containing fractions were combined and solvent removed to yield ethyl-(4-{8-chloro-5,6-dihydro-11H-benzo[5,6]cyclohepta[1,2-b]pyridin-11-ylidene)piperidin-1-yl)acetate as a white solid (214 mg, 34%)

$^1$H-NMR; δ (CDCl$_3$), 8.40 (1H, dd, J=4.6, 1.3 Hz), 7.43 (1H, dd, J=7.6, 1.6 Hz), 7.15–7.07 (4H, m), 4.23–4.15 (2H, m), 3.44–3.33 (2H, m), 2.87–2.76 (4H, m), 2.63 (2H, t, J=6.0 Hz), 2.56–2.18 (6H, m), 2.05 (3H, s).

(b) 4-{8-Chloro-5,6-dihydro-11H-benzo{5,6,}cyclohepta{1,2-b}pyridin-11-yliden}piperidin-1-yl-ethanol An aqueous solution of potassium carbonate (299 mg, 2.16 mmol, 5 ml water) was added to a solution of ethyl-(4-{8-chloro-5,6-dihydro-11H-benzo[5,6]cyclohepta-[1,2-b]pyridin-11-ylidene)piperidin-1-yl)acetate (214 mg, 0.54 mmol) in methanol (20 ml). The reaction was stirred at room temperature for 24 hours followed by 3 hours at 800° C. Methanol was removed under reduced pressure and the residue partitioned between DCM and brine. The crude product was purified by chromatography on silica gel using a gradient elution of 5% methanol in DCM. Product containing fractions were combined and solvent evaporated to leave 4-{8-chloro-5,6-dihydro-11H-benzo[5,6]cyclohepta[1,2-b]pyridin-11-ylidene}-piperidin-1-yl-ethanol as a white solid (136 mg, 71%).

$^1$H-NMR; δ (CDCl$_3$), 8.40 (1H, dd, J=4.9, 1.5 Hz), 744 (1H, dd, J=7.7, 1.2 Hz), 7.16–709 (4H, m), 3.65 (2H, t, J=5.2

Hz), 3.44–3.33 (2H, m), 2.88–2.80 (4H,m), 2.61–2.54 (3H, m), 2.54–2.37 (5H, m).

(c) N-Methyl-N-4-(1H-2-methylimidazo[4,5-c]pyridinylmethyl)phenylsulphonyl-L-leucine-2-(4-{8-chloro-5,6-dihydro-11H-benzo[5,6]cyclohepta[1,2-b]pyridin-11-ylidene)piperidin-1-yl)-ethyl ester.

Following a procedure similar to that described for example 3(b), N-methyl-N-4-(1H-2-methylimidazo[4,5-c]pyridinylmethyl)-phenylsulphonyl-L-leucine (198 mg, 0.46 mmol) was coupled to 4-{8-chloro-5,6-dihydro-11H-benzo[5,6]cyclohepta[1,2-b]pyridin-11-ylidene}-piperidin-1-yl-ethanol (135 mg, 0.38 mmol) to yield N-methyl-N-4-(1H-2-methylimidazo[4,5-c]pyridinylmethyl)phenylsulphonyl-L-leucine-2-(4-{8-chloro-5,6-dihydro-11H-benzo[5,6]cyclohepta[1,2-b]pyridin-11-ylidene}piperidin-1-yl)-ethyl ester as a white solid (32 mg, 11%).

1H-NMR; δ (CDCl$_3$), 9.02 (1H, s), 8.39–8.35 (2H, m), 7.76 (2H, d, J=8.4 Hz), 7.43 (1H, m), 7.15–7.08 (7H, m), 5.38 (2H, d, J=2.8 Hz), 4.65–4.62 (1H, m), 3.97–3.87 (2H,m), 3.43–3.32 (2H, m), 2.87–2.76 (1H, m), 2.83 (3H, s), 2.68–2.64 (2H, m), 2.58 (3H, s), 2.48–2.26 (7H, m), 2.17–2.05 (2H, m), 1.64–1.55 (3H, m) and 0.93 (6H, d, J=4.6 Hz).

13C-NMR; δ (CDCl$_3$), 170.8, 157.3, 153.3, 146.6, 142.2, 142.1, 140.2, 139.8, 139.6, 139.5, 139.4, 137.9, 137.7, 137.4, 133.4, 133.0, 132.7, 130.7, 128.9, 128.3, 126.6, 126.0, 122.2, 104.7, 62.0, 57.2, 56.1, 55.0, 54.9, 54.8, 46.9, 38.1, 31.7, 31.4, 30.8, 30.6, 29.8, 29.7, 24.4 and 14.0.

EXAMPLE 16

N-Methyl-N-4-(1H-2-methylimidazo[4,5-c]pyrdinylmethyl)phenylsulphonyl-L-leucine-(R,S)-5-(4-benzhydrylpiperazin-1yl-2-pentyl ester.

(a) 5-(4-Benzhydrylpiperazin-1-yl)-2-pentanone ethylene ketal

A solution of 5,chloro-2-pentanone (2.00 mg, 12.2 mmol), benzhydrylpiperazine (3.70 g, 14.6 mmol), sodium iodide (10 mg) and potassium carbonate (3.36 g, 24.3 mmol) in acetone (40 ml) was heated under reflux for 18 hours. Acetone was removed under reduced pressure. Dichloromethane was added to the residue and the undissolved inorganic salts removed by filtration. The product was purified by column chromatography on silica gel eluting with 4% methanol/DCM. Product containing fractions were combined and solvent removed to yield 5-(4-benzhydrylpiperazin-1-yl)-2-pentanone ethylene ketal as a colourless oil (1.54 g, 33%).

1H-NMR; δ (CDCl$_3$), 7.41 (4H, d, J=7.5 Hz), 7.27–7.25 (4H, m), 7.19–7.16 (2H, m), 4.23 (1H, s), 3.96–3.89 (4H, m), 2.67–2.40 (10H, m), 1.91–1.78 (4H, m), 1.31 (3H, s).

(b) 5-(4-Benzhydrylpiperazin-1-yl)-2-pentanone

A solution of 5-(4-benzhydrylpiperazin-1-yl)-2-pentanone ethylene ketal (1.10 g, 2.9 mmol) in THF (25 ml) was treated with concentrated hydrochloric acid (2 ml) and stirred at room temperature overnight. The reaction mixture was evaporated to dryness before partitioning between ethyl acetate and saturated sodium bicarbonate solution. The organic layer was separated, dried over anhydrous sodium sulphate, filtered and concentrated to yield 5-(4-benzhydrylpiperazin-1-yl)-2-pentanone as a colourless oil (716 mg, 80%).

1H-NMR; δ (CDCl$_3$), 7.41 (4H, J=7.4 Hz), 7.28–7.24 (4H, m), 7.19–7.16 (2H, m), 4.20 (1H, m), 2.56–2.34 (10H, m), 2.32 (2H, t, J=7.2 Hz), 2.14 (3H, s), 1.78–1.72 (2H, m).

(c) (RS)-5-(4-Benzhydrylpiperazin-1-yl)-2-pentanol

Lithium aluminium hydride (97 mg, 2.56 mmol) was taken up in dry THF (15 ml) and stirred under an inert atmosphere at -78° C. 5-(4-Benzhydrylpiperazin-1-yl)-2-pentanone (717 mg, 2.13 mmol) as a solution in THF (35 ml) was added dropwise. The reaction was stirred at -78° C. for 15 minutes before allowing to warm to room temperature. After a total reaction time of 30 minutes the reaction was quenched with a 15% aqueous solution of sodium hydroxide (25 ml). The reaction mixture was filtered through Kieselguhr gel and partitioned between ethyl acetate and water. The organic layer was separated, dried over sodium sulphate, filtered and solvent removed under reduced pressure to yield (RS)-5-(4-benzhydrylpiperazin-1-yl)-2-pentanol as a white powder (686 mg, 95%).

1H-NMR; δ (CDCl$_3$), 7.40 (4H, d, J=7.9 Hz), 7.27–7.24 (4H, m), 7.18–7.15 (2H, m,), 4.20 (1H, s), 3.69–3.66 (1H, m), 2.80–2.20 (10H, m), 1.81–1.55 (4H, m), 1.15 (3H, d, J=6.1 Hz).

(d) N-Methyl-N-4-(1H-2-methylimidazo[4,5-c]pyridinylmethyl)phenylsulphonyl-L-leucine-(R,S)-5-(4-benzhydrylpiperazin-1yl)-2-pentyl ester.

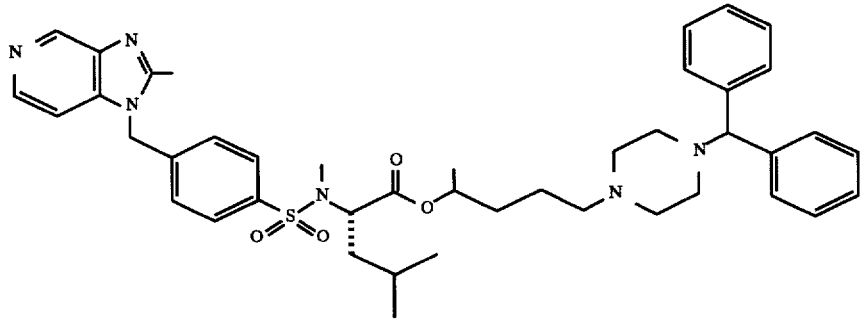

Following a procedure similar to that described for example 3(b) N-methyl-N-4-(1H-2-methylimidazo[4,5-c]pyridinylmethyl)phenylsulphonyl-L-leucine (1.05 g, 2.44 mmol) was coupled to (RS)-5-(4-benzhydrylpiperazin-1-yl)-2-pentanol (0.69 g, 2.03 mmol) to yield N-methyl-N-4-(1H-2-methylimidazo[4,5-c]pyridinylmethyl) phenylsulphonyl-L-leucine- (R,S)-5-(4-benzhydrylpiperazin-lyl)-2-pentyl ester as a white solid (612 mg, 40%).

1H-NMR; δ (CDCl$_3$), 9.05 (1H, d, J=4.7 Hz), 8.38 (1H, m), 7.77 (2H, m), 7.40 (3H, d, J=7.6 Hz), 7.26 (4H, m), 7.18–7.12 (6H, m), 5.44–5.23 (2H, m), 4.68–4.58 (2H, m), 3.40 (1H, s), 2.82 (3H, m), 2.59 (3H, m), 2.49–2.13 (5H, m), 1.92–1.52 (8H, m), 1.42–1.14 (4H, m), 1.01–0.96 (3H, m), and 0.95–0.92 (6H, m).

13C-NMR; δ (CDCl$_3$), 170.6, 142.6, 142.2, 142.1, 139.8, 139.6, 128.4, 128.3, 127.9, 126.9, 126.7, 126.6, 104.6, 76.2, 72.0, 71.9, 58.1, 57.3, 57.1, 53.4, 51.8, 46.9, 38.1, 38.0, 33.4, 29.8, 24.4, 21.0, 19.7, 19.6 and 14.0.

EXAMPLE 17

4-Methyl-2-{methyl-[4-(2-methyl-imidazo[4,5-c] pyridin-1-ylmethyl)-phenylsulphonyl]-amino}- pentanoic acid-(E)-3-(6-[3-pyrrolidino-1-{4-tolyl}- prop-1E-enyl]-pyridin-2-yl)-prop-2-en-1-yl ester.

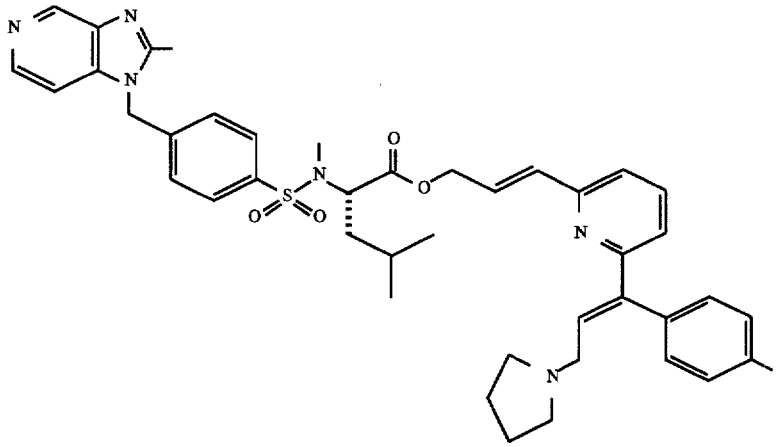

(a) Methyl-(E)-3-(6-[3-pyrrolidin-1-yl-{4-tolyl}-prop-1E-enyl]-pyridin-2-yl)-acrylate A solution of (E)-3-(6-[3-pyrrolidin-1-yl-{4-tolyl}-prop-1E-enyl]-pyridin-2-yl)-acrylic acid (2.04 g, 5.9 mmol) in methanol (50 m l) was treated with concentrated hydrochloric acid (10 ml) and stirred at room temperature for 6 days. The reaction was neutralised with sodium hydrogen carbonate and solvent removed under reduced pressure. DCM was added to the filtrate and inorganic solids removed by filtration. Concentration of the filtrate under reduced pressure yielded methyl-(E)-3-(6-[3-pyrrolidin-1-yl-}4-tolyl{4-tolyl}-prop-1E-enyl]-pyridin-2-yl)-acrylate as a pink foam (1.98 g, 93%).

$^1$H-NMR; δ (CDCl$_3$), 7.70 (1H, d, J=15.7 Hz), 7.57 (1H, t, J=7.7 Hz), 7.30 (1H, t, J=7.6 Hz), 7.25 (2H, d, J=8.3 Hz), 7.17 (1H, d, J=7.2 Hz), 7.10 (2H, dt, J=8.2, 1.8 Hz), 6.96 (1H, d, J=15.6 Hz), 6.93 (1H, d, J=7.9 Hz), 3.83 (3H, s), 3.65 (2H, s), 3.65 (2H,brs), 2.85 (4H, brm), 2.41 (3H, s), 2.04 (4H, brm).

(b) (E)-3-(6-[3-Pyrrolidino-1-{4-tolyl}-prop-1E-enyl]-pyridin-2-yl)-prop-2-en-1-ol A solution of methyl-(E)-3-(6-[3-pyrrolidin-1-yl-{4-tolyl}-prop-1E-enyl]-pyridin-2-yl) acrylate (1.98 g, 5.47 mmol) in dry THF (100 ml) was cooled to -78° C. and treated under an inert atmosphere with a solution of DIBAL (1M in toluene, 16.4 ml, 16.4 mmol). After stirring for 3 hours at -78° C. more DIBAL was added (11 ml, 11 mmol) and the reaction allowed to warm to room temperature. Following a total reaction time of 24 hours the reaction was quenched with water (0.5 ml). The reaction mixture was partitioned between DCM and water. The aqueous layer was separated, acidified (20 ml, 1 M HCl) and extracted with DCM. The organic extracts were combined, dried over sodium sulphate, filtered and concentrated under reduced pressure to yield (E)-3-(6-[3-pyrrolidino-1-{4-tolyl}-prop-1E-enyl]-pyridin-2-yl)-prop-2-en-1-ol as an off white solid (1.69 g, 93%).

$^1$H-NMR; δ (CDCl$_3$), 7.40 (1H, t, J=7.9 Hz), 7.19 (2H, d, J=7.8 Hz), 7.16 (1H, t, J=7.3 Hz), 7.08 (1H, d, J=7.7 Hz), 7.01 (2H, d, J=7.9 Hz), 6.96 (1H, dt, J=15.7, 5.0 Hz), 6.69 (1H, d, J=15.7 Hz), 6.66 (1H, d, J=7.8 Hz), 4.36 (2H, dd, J=5.0, 1.4 Hz), 3.58 (2H, d, J=7.2 Hz), 3.04 (4H, br s), 2.36 (3H, s) and 1.96 (4H, br s).

$^{13}$C-NMR; δ (CDCl$_3$), 155.8, 154.7, 146.6, 137.9, 136.9, 134.8, 133.8, 129.5, 129.4, 129.3, 129.1, 121.1, 120.8, 62.6, 53.0, 52.8, 29.6, 23.4, 23.4 and 21.2.

(c) 4-Methyl-2-{methyl-[4-(2-methyl-imidazo[4,5-c] pyridin-1-ylmethyl)-phenylsulphonyl]-amino}-pentanoic acid-(E)-3-(6-[3-pyrrolidino-1-{4-tolyl}-prop-1E-enyl]-pyridin-2-yl)-prop-2-en-1-yl ester.

Following a procedure similar to that described for example 3(b), N-methyl-N-4-(1H-2methylimidazo[4,5-c] pyridinylmethyl)phenylsulphonyl-L-leucine (300 mg, 0.70 mmol) was coupled to (E)-3-(6-[3-pyrrolidino-1-{(4-tolyl}-prop-1E-enyl]-pyridin-2-yl)-prop-2-en-1-ol (194 mg, 0.58 mmol) to yield 4-methyl-2-{methyl-[4-(2-methyl-imidazo [4,5-c]pyridin-1-ylmethyl)-phenylsulphonyl]-amino}-pentanoic acid-(E)-3-(6-[3-pyrrolidino-1-{4-tolyl}-prop-1E-enyl]-pyridin-2-yl)-prop-2-en-1-yl ester as a pink foam (108 mg, 25%).

$^1$H-NMR; δ (CDCl$_3$), 8.98 (1H, s), 8.31 (1H, d, J=5.2 Hz), 7.75 (2H, d, J=8.3 Hz), 7.51 (1H, t, J=7.8 Hz), 7.24 (3H, m), 7.14 (4H, m), 7.04 (2H, d, J=7.9 Hz), 6.79 (1H, d, J=7.8 Hz), 6.72–6.68 (1H, dt, J=15.8, 5.7 Hz), 6.54 (1H, d, J=15.8 Hz), 5.40 (2H, d, J=2.3 Hz), 4.71 (1 H, t, J=9.5 Hz), 4.47 (2H, m), 3.68 (2H, d, J=7.2 Hz), 2.92 (4H, m), 2.85 (3H, s), 2.55 (3H, s), 2.39 (3H, s), 2.01 (4H, m), 1.65 (3H, m) and 0.96 (6H, m).

$^{13}$C-NMR; (CDC l$_3$), 170.5, 155.8, 153.7, 153.6, 140.3, 140.0, 139.8, 139.1, 138.3, 137.2, 133.3, 132.7, 129.7, 129.2, 128.2, 127.5, 126.8, 121.8, 121.1, 104.8, 64.4, 57.3, 53.2, 52.8, 46.9, 38.1, 29.9, 24.4, 23.3, 23.0, 21.2 and 14.0.

EXAMPLE 18

N-(1-{2-[4-(8-Chloro-5,6-dihydro-benzo[5,6] cyclohepta[1,2-b]pyridin-11-ylidene)-piperidin-1-yl] -2-oxo-ethoxymethyl}-3-methyl-butyl)-N-methyl-4- (1H-2-methylimidazo[4,5-c]pyridin-1-ylmethyl)- phenylsulphonamide.

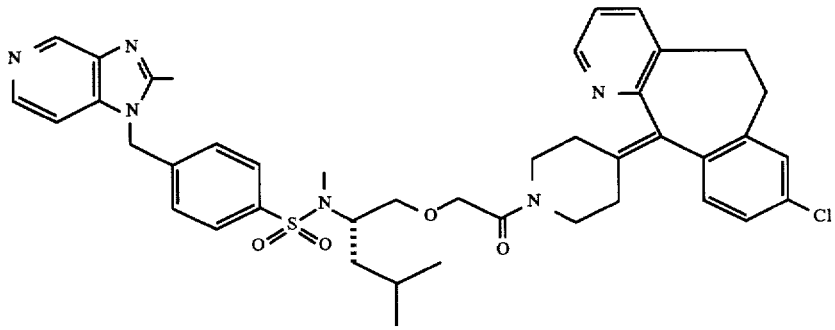

(a) (4-Methyl-2-{methyl-[4-(1H-2-methyl-imidazo[4,5-c]pyridin-1-ylmethyl)-phenylsulphonyl]-amino}-pentyloxy)-acetic acid tert-butyl ester.

A solution of N-methyl-N-4-(1H-2-methylimidazo[4,5-c]pyridinylmethyl)-phenylsulphonyl-L-leucinol (2.00 g, 4.80 mmol) in dry DMF (30 ml) was treated with sodium hydride (127 mg, 5.28 mmol, 60% dispersion in oil) under an inert atmosphere and stirred for 30 minutes at room temperature. The reaction mixture was cooled to 0° C. and tert-butylbromoacetate (775 μl, 4.48 mmol) added. The reaction was allowed to warm to ambient temperature and stirred for 18 hours. Solvent was removed under reduced pressure and the residue resuspended in DCM before washing with saturated sodium bicarbonate solution and brine. The organic solution was dried over sodium sulphate, filtered and concentrated to leave a red oil. The product was purified by chromatography on silica gel eluting with 4–6% methanol/DCM. Product containing fractions were combined and solvent removed to yield (4-methyl-2-{methyl-[4-(1H-2-methyl-imidazo[4,5-c]pyridin-1-ylmethyl)-phenylsulphonyl]-amino}-pentyloxy)-acetic acid tert-butyl ester as an orange foam (480 mg, 19%).

$^1$H-NMR; δ (CDCl$_3$), 9.04 (1H, s), 8.38 (1H, d, J=5.6 Hz), 7.85 (2H, d, J=8.3 Hz), 7.14 (1H, d, J=5.6 Hz), 7.12 (2H, d, J=8.3 Hz), 5.40 (2H, s), 4.22–4.19 (1H, m), 3.69 (2H, m), 3.46–3.36 (2H, m), 2.74 (3H, s), 2.59 (3H, s), 1.56–1.45 (1H, m), 1.43 (9H, s), 1.38–1.19 (2H, m), 0.89 (3H, d, J=5.1 Hz), 0.88 (3H, d, J=5.3 Hz).

(b) N-(1-{2-[4-(8-Chloro-5,6-dihydro-benzo[5,6]cyclohepta[1,2-b]pyridin-11-ylidene)-piperidin-1-yl]-2-oxo-ethoxymethyl}-3-methyl-butyl)-N-methyl-4-(1H-2-methylimidazo[4,5-c]pyridin-1-ylmethyl)-phenylsulphonamide.

A solution of (4-methyl-2-{methyl-[4-(1H-2-methyl-imidazo[4,5-c]pyridin-1-ylmethyl)-phenylsulphonyl]-amino}-pentyloxy)-acetic acid tert-butyl ester (325 mg, 0.61 mmol) in DCM (8 ml) was cooled to 0° C. and treated with trifluoroacetic acid (2 ml). The reaction was stored at 5° C. for 18 hours before concentrating under reduced pressure. The resulting white foam was coupled to 4-(8-chloro-5,6-dihydro-11H-benzo[5,6]cyclohepta[1,2-b]pyrid-11-ylidene) piperidine (208 mg, 0.67 mmol) using a procedure similar to that described for example 6 to yield N-(1-{2-[4-(8-chloro-5,6-dihydro-benzo[5,6]-cyclohepta[1,2-b]pyridin-11-ylidene)-piperidin-1-yl]-2-oxo-ethoxymethyl}-3-methyl-butyl)-N-methyl-4-(1H-2-methylimidazo[4,5-c]pyridin-1-ylmethyl}-phenylsulphonamide as a white foam (214 mg, 42%).

$^1$H-NMR; δ (CDCl$_3$), 9.01 (1H, d, J=8.0 Hz), 8.38 (2H, m), 7.81 (2H, m), 7.45 (1H, d, J=7.7 Hz), 7.18–7.08 (7H, m), 5.38 (2H, s), 4.18 (1 H, t, J=3.3 Hz), 4.04–3.89 (3H, m), 3.55 (1 H, m), 3.45–3.32 (4H, m), 3.16–3.05 (2H, m), 2.90–2.78 (2H, m), 2.70 (3H, s), 2.58 (3H, s), 2.47 (1-H, m), 2.33 (3H, m), 1.48 (H, m), 1.31–1.17 (2H, m), and 0.86 (6H, m).

$^{13}$C-NMR; δ (CDCl$_3$), 167.0, 156.7, 153.3, 146.7, 142.2, 140.5, 140.2, 139.8, 139.5, 139.3, 137.7, 137.5, 137.4, 136.3, 134.9, 133.4, 133.1, 130.3, 129.0, 128.3, 126.5, 126.3, 122.4, 104.7, 71.9, 70.0, 54.6, 46.8, 45.6, 42.9, 37.7, 31.6, 31.2, 31.0, 30.4, 30.2, 28.6, 24.4, 23.1, 22.0, 14.0.

EXAMPLE 19

(S)-N-{1-[2-(4-Benzhydryl-piperazin-1-yl)-ethoxymethyl]-3-methyl-butyl}-methyl-4-(1H-2-methylimidazo[4,5-c]pyridin-1-ylmethyl)-phenylsulphonamide.

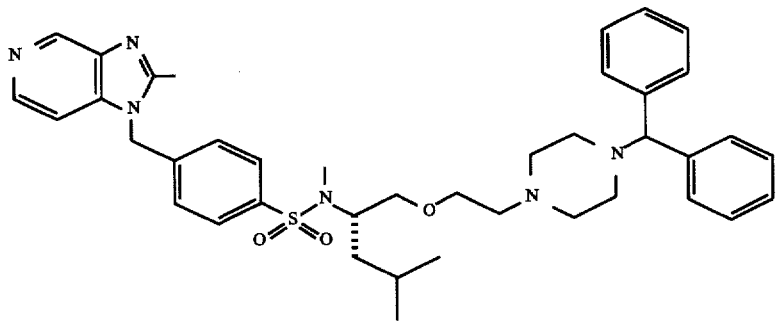

methylimidazo[4,5-c]pyridin-1-ylmethyl)-phenylsulphonamide.

A solution of (4-methyl-2-{methyl-[4-(1H-2-methyl-imidazo[4,5-c]pyridin-1-ylmethyl)-phenylsulphonyl]-amino}-pentyloxy)-acetic acid tert-butyl ester (325 mg, 0.61 mmol) in DCM (8 ml) was cooled to 0° C. and treated with (a) N-[1-(2-Hydroxy-ethoxymethyl)-butyl]-N-methyl-4-(1H-2-methyl-imidazo[4,5-c]pyridin-1-ylmethyl)-phenylsulphonamide Lithium aluminium hydride was taken up in dry THF (25 ml), cooled to −78° C. and treated under an inert atmosphere with a solution of tert-butyl-[N-methyl-N-4-(1H-2- methylimidazo[4,5-c]pyridinylmethyl)-phenylsulphonyl-L-leucinol-O-acetate (1.00 g, 1.88 mmol) in THF (10 ml). The reaction mixture was stirred at -78° C. for 15 minutes before warming to ambient temperature. After a total reaction time of 40 minutes the reaction was cooled to −780° C. and quenched with sodium hydroxide solution (5 ml, 15%). The reaction mixture was filtered through Kieselguhr gel and partitioned between ethyl acetate and water. The organic layer was separated, dried over sodium sulphate, filtered and solvent removed to yield N-[1-(2-hydroxy-ethoxymethyl)-butyl]-N-methyl-4-(1H-2-methyl-imidazo[4,5-c]pyridin-1-ylmethyl)-phenylsulphonamide as a yellow oil (838 mg, 97%).

$^{1}$H-NMR; δ (CDCl$_{3}$), 9.03 (1H, s), 8.38 (1H, d, J=5.6 Hz), 7.81 (2H, d, J=8.5 Hz), 7.18 (1H, d, J=5.9 Hz), 7.13 (2H, d, J=8.2 Hz), 5.40 (2H, s), 4.31–4.28 (1H, m), 3.57–3.27 (6H, m), 2.61 (3H, s), 2.60 (3H, s), 1.55–1.51 (1H, m), 1.35–1.28 (1H, m), 1.15–1.11 (1H, m), 0.92 (3H, d, J=6.6 Hz), 0.89 (3H, d, J=6.6 Hz).

(b) Methanesulphonic acid 2-(4-methyl-2-(methyl-imidazo[4,5-c]pyridin-1-ylmethyl)-phenylsulphony]-amino}-pentyloxy)ethyl ester.

A solution of N-[1-(2-hydroxy-ethoxymethyl)-butyl]-N-methyl-4-(1 H-2-methyl-imidazo[4,5-c]pyridin-1-ylmethyl)-phenylsulphonamide (830 mg, 1.80 mmol) in DCM (15 ml), stirred under an inert atmosphere at 0° C., was treated with triethylamine (264 mg, 3.6 mmol) and methane sulphonylchloride (309 mg, 2.7 mmol). The reaction was allowed to warm to room temperature and stirred for 18 hours before partitioning between DCM and 1M HCl. The organic layer was separated, washed with brine, dried over sodium sulphate, filtered and concentrated under reduced pressure to yield methanesulphonic acid 2-(4-methyl-2-{methyl-imidazo[4,5-c]pyridin-1-ylmethyl)-phenylsulphony]-amino}-pentyloxy)ethyl ester as a yellow oil (882 mg, 91%).

$^{1}$H-NMR; δ (CDCl$_{3}$), 9.01 (1H, s), 8.47 (1H, d, J=6.4 Hz), 7.90 (1H, d, J=6.4 Hz), 7.81 (2H, d, J=8.3 Hz), 7.21 (2H, d, J=8.4 Hz), 5.67 (2H, s), 4.25–4.17 (1H, m), 4.09 (2H, t, J=4.4 Hz), 3.57–3.53 (1 H, m), 3.48–3.42 (1 H, m), 3.31 (2H,d, J=6.7 Hz), 3.02 (3H,s), 2.71 (3H, s), 2.66 (3H, s), 1.62–1.58 (1H, m), 1.38–1.32 (1H, m), 1.18–1.10 (1H, m), 0.92 (3H, d, J=6.6 Hz), 0.90 (3H, d, J=6.8 Hz).

(c) (S)-N-{1-[2-(4-Benzhydryl-piperazin-1-yl)-ethoxymethyl]-3-methyl-butyl}-methyl-4-(1H-2-methylimidazo[4,5-c]pyridin-1-ylmethyl)-phenylsulphonamide A solution of methanesulphonic acid 2-(4-methyl-2-{methyl-imidazo[4,5-c]pyridin-1-ylmethyl)-phenylsulphonyl]-amino}-pentyloxy)ethyl ester (440 mg, 0.82 mmol), benzhydrylpiperazine (414 mg, 1.64 mmol), triethylamine (100 mg, 0.98 mmol) and sodium iodide (20 mg) in THF (30 ml) was heated under reflux for 96 hours. The reaction mixture was concentrated under reduced pressure and the residue partitioned between DCM and water. The organic layer was separated, dried over sodium sulphate, filtered and concentrated to leave a yellow gum. The product was purified by column chromatography on silica gel eluting with 5% methanol/DCM. Product containing fractions were combined and solvent removed to yield (S)-N-{1-[2-(4-Benzhydryl-piperazin-1-yl)-ethoxymethyl]-3-methyl-butyl}-methyl-4-(1H-2-methylimidazo[4,5-c]pyridin-1-ylmethyl)-phenylsulphonamide as a yellow glass (188 mg, 33%).

$^{1}$H-NMR; δ (CDCl$_{3}$), 9.04 (1H, s), 8.38 (1H, d, J=5.7 Hz), 7.80 (2H, m), 7.41 (4H, m), 7.29–7.25 (4H, m), 7.19–7.10 (5H, m), 5.37 (2H, s), 4.20 (1H, s), 4.13 (1H, m), 3.43–3.32 (2H, m), 3.31–3.27 (2H, m), 2.68 (3H, s), 2.58 (3H, s), 2.43 (10H, brs), 1.48 (1H, m), 1.29–1.17 (2H, m), and 0.85 (6H, m).

$^{13}$C-NMR; δ (CDCl$_{3}$), 142.6, 142.2, 142.2, 140.6, 140.2, 139.8, 139.2, 128.5, 128.4, 127.9, 126.9, 126.4, 104.6, 76.2, 71.6, 68.7, 57.4, 54.6, 53.8, 51.7,46.8, 37.8, 24.4, 23.1, 22.1 and 14.0.

Examples 20–25 were synthesised using (S)-(1-ethoxymethyl-3-methylbutyl)-4-(1H-2-methylimidazo[4,5-c]pyridin-1-ylmethyl)-phenylsulphonamide, the synthesis of which is described in international patent application WO 92/03422.

EXAMPLE 20

N-(2-[4-(8-Chloro-5,6-dihydro-11H-benzo[5,6] cyclohepta[1,2-b]pyridin-11-ylidene)-piperidin-1-yl]- 2-oxo-ethyl}-N-(S)-(1-ethoxymethyl-3-methylbutyl)-4-(1H-2-methylimidazo[4,5-c]pyridin-1-ylmethyl)-phenylsulphonamide.

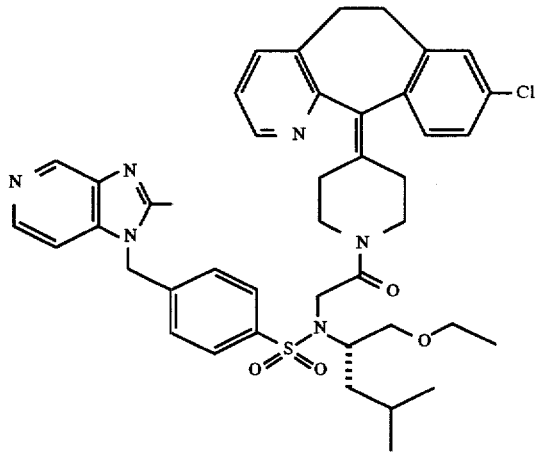

(a) {(S)-(1-Ethoxymethyl-3-methylbutyl)-[4-(1H-2-methylimidazo[4,5-c]pyridin-1-ylmethyl)-phenylsulphonyl]-amino)-acetic acid tert butyl ester.

A solution of (S)-(1-ethoxymethyl-3-methylbutyl)-4-(1H-2-methylimidazo[4,5-c]pyridin-1-ylmethyl)-phenylsulphonamide (5.00 g, 11.61 mmol) in anhydrous DMF (50 ml) under an inert atmosphere was treated with sodium hydride (557 mg, 60% in oil, 13.93 mmol) and stirred at room temperature for 30 minutes. The reaction mixture was cooled in an ice-water bath and tert-butyl obromoacetate added. After warming to room temperature the reaction was stirred for 18 hours. DMF was removed under reduced pressure. The residue was resuspended in DCM and washed with saturated aqueous sodium bicarbonate and brine, before drying over magnesium sulphate, filtration and concentration to a red oil. The product was purified by column chromatography on silica gel eluting with 4–5% methanol/DCM. Product containing fractions were combined and solvent removed to yield {(S)-(1-ethoxymethyl-3-methylbutyl)-[4-(1H-2-methylimidazo[4,5-c]pyridin-1-ylmethyl)-phenylsulphonyl]-amino }acetic acid tert butyl ester as an orange foam (4.95 g, 78%).

$^{1}$H-NMR; δ (CDCl$_{3}$), 9.03 (1H, s), 8.37 (1H, d, J=5.5 Hz), 7.91 (2H, d, J=8.3 Hz), 7.13 (3H, m), 5.38 (2H, s), 3.97 (2H, d, J=3.9 Hz), 3.70 (1 H, m), 3.40 (1 H, dd, J=3.9, 9.8 Hz), 3.33 (1 H, dd, J=4.7, 9.8 Hz), 3.31–3.22 (2H, m), 2.58 (3H, s), 1.49–1.45 (1H, m), 1.43 (9H, s), 1.42–1.38 (1H, m), 1.23–1.18 (1H, m), 1.01 (3H, t, J=7.0 Hz), 0.93 (3H, d, J=6.5 Hz) and 0.69 (3H, d, J=6.4 Hz).

$^{13}$C-NMR; δ (CDCl$_{3}$), 169.0, 153.3, 142.1, 140.8, 140.2, 139.8, 139.5, 128.9, 126.4, 104.7, 81.5, 71.5, 66.4, 55.2, 46.9, 45.8, 38.4, 27.9, 24.2, 22.5, 22.4, 14.9 and 14.0.

(b) N-(2-[4-(8-Chloro-5,6-dihydro-11H-benzo[5,6]cyclohepta[1,2-b]pyridin-11-ylidene)-piperidin-1-yl]-2-oxo-ethyl}-N-(S)-(1-ethoxymethyl-3-methylbutyl)-4-(1H-2-methylimidazo[4,5-c]pyridin-1-ylmethyl)-phenylsulphonamide.

{(S)-(1-Ethoxymethyl-3-methylbutyl)-[4-(1H-2-methylimidazo [4,5-c]pyridin-1-ylmethyl)-phenylsulphonyl]-amino}-acetic acid tert butyl ester (500 mg, 0.92 mmol) was taken up in DCM (8 ml), cooled to OC and treated with trifluoroacetic acid (2 ml). The reaction was stored at 0° C. for 18 hours. The reaction mixture was concentrated under reduced pressure and the residue azeotroped with DCM. The resulting carboxylic acid was taken up in a mixture of DCM/DMF (20 ml/2 ml), cooled to 0° C. and treated with N-(3-dimethylaminopropyl)-N-ethylcarbodiimide hydrochloride (230 mg, 1.20 mmol), N-methylmorpholine (303 µl, 2.76 mmol) and pentafluorophenol (221 mg, 1.20 mmol). The resulting solution was allowed to stir at room temperature for 4 hours before the addition of 4-(8-chloro-5,6-dihydro-11H-benzo[5,6]-cyclohepta[1,2-b]pyridin-11-ylidene)piperidine (286 mg, 0.92 mmol). The reaction was stirred at room temperature for 150 hours. Solvent was removed under reduced pressure. The residue was taken up in DCM and washed with saturated aqueous sodium bicarbonate and brine. The organic layer was dried over sodium sulphate, filtered and evaporated. The product was purified by column chromatography on silica gel, eluting with 4–5% methanol/DCM. Product containing fractions were combined and solvent removed to yield N-{2-[4-(8-chloro-5,6-dihydro-11H-benzo[5,6]cyclohepta[1,2-b]pyridin-11-ylidene)-piperidin-1-yl]-2-oxo-ethyl}-N-(S)-(1-ethoxymethyl-3-methylbutyl)-4-(1H-2-methylimidazo[4,5-c]pyridin-1-ylmethyl)-phenylsulphonamide as a white foam (267 mg, 37%).

$^1$H-NMR; δ (CDCl$_3$), 9.04 (1H, s), 8.40 (1H, d, J=3.9 Hz), 8.37 (1H, d, J=5.6 Hz), 8.01 (2H, d, J=8.5 Hz), 7.45 (1H, d, J=7.7 Hz), 7.18–7.10 (7H, m), 5.38 (2H, s), 4.28 (2H, m), 4.08–3.86 (1 H, m), 3.69 (2H, m), 3.45–3.03 (8H, bm), 2.89–2.79 (2H, bm), 2.59 (3H, s), 2.50–2.30 (4H, bm), 1.51–1.38 (2H, m), 1.25 (1H, m), 1.03–0.96 (3H, m) and 0.72 (6H, m).

$^{13}$C-NMR; δ (CDCl$_3$),167.2, 167.1, 156.8, 156.6, 153.3, 146.7, 142.2, 142.1, 140.8, 140.6, 140.2, 139.8, 139.5, 139.4, 137.6, 137.5, 137.4, 136.4, 134.8, 133.4, 133.3, 133.1, 130.4, 129.3, 129.0, 126.3, 122.4, 104.7, 71.3, 71.1, 66.3, 55.5, 55.4, 46.9, 45.7, 45.6, 45.5, 43.3, 43.2, 38.4, 38.3, 31.6, 31.5, 31.0, 30.8, 30.7, 30.3, 30.1, 24.4 and 14.0.

EXAMPLE 21

N-(2-{[4-(R,S)-(4-Chlorophenyl)-phenyl-methyl]piperazin-1-yl)ethyl)-N-(S)-(1-ethoxymethyl-3-methylbutyl)-4-(1H-2-methylimidazo[4,5-c]pyridin-1 ylmethyl)-phenylsulphonamide.

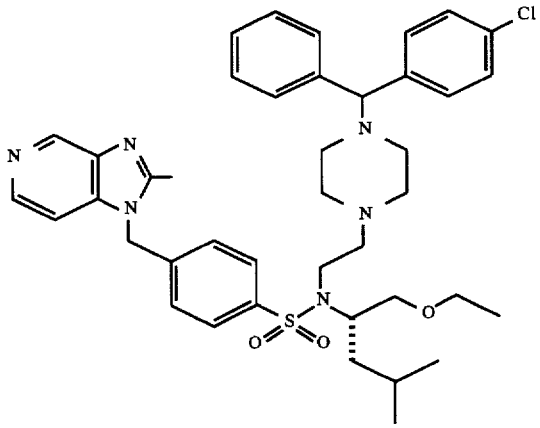

(a) N-(S)-(1-Ethoxymethyl-3-methylbutyl)-N-(2-hydroxyethyl)-4-(1H-2-methylimidazo[4,5-c]pyridin-1-ylmethyl)-phenylsulphonamide.

Lithium aluminium hydride (418 mg, 11.01 mmol) was taken up in anhydrous THF (10 ml) and stirred at –78° C. under an inert atmosphere. A solution of {(S)-(1-ethoxymethyl-3-methylbutyl)-ethoxymethyl-3-methylbutyl)-[4-(1H-2-methylimidazo[4,5-c]pyridin-1-ylmethyl)-phenylsulphonyl]-amino}-acetic acid tert butyl ester (2.00 g, 3.67 mmol in THF (40 ml) was added dropwise to the cooled solution. The mixture was stirred at –78° C. for 15 minutes and allowed to warm to ambient temperature. After a total reaction time of 30 minutes the reaction was cooled to –78° C. before quenching with a 15% aqueous solution of sodium hydroxide (5 ml). After warming to room temperature more sodium hydroxide solution was added (15 ml) and a gelatinous precipitate formed. The suspension was filtered through keiselguhr and concentrated under vacuum to yield N-(S)-(1-ethoxymethyl-3-methylbutyl)-N-(2-hydroxyethyl)-4-(1H-2-methylimidazo[4,5-c]pyridin-1-ylmethyl)-phenylsulphonamide as a yellow foam (1.53 g, 88%).

$^1$H-NMR; δ (CDCl$_3$), 9.06 (1 H, d, J=0.7 Hz), 8.39 (1 H, d, J=5.6 Hz), 7.86 (2H, d, J=8.3 Hz), 7.16–7.14 (3H, m), 5.41 (2H, s), 4.00–3.97 (1H, m), 3.78–3.74 (1H, m),3.66–3.61 (1H, m), 3.51–3.26 (6H, m), 2.61 (3H, s), 1.51–1.47 (1H, m), 1.38–1.29 (2H, m), 1.00 (3H, t, J=7.0 Hz) and 0.85 (6H, t, J=6.1 Hz).

(b) N-(S)-(1-Ethoxymethyl-3-methylbutyl)-N-(2-ethyl-O-methanesulphonate)-4-(1H-2-methylimidazo[4,5-c]pyridin-1-ylmethyl)-phenylsulphonamide.

A solution of N-(S)-(1-ethoxymethyl-3-methylbutyl)-N-(2-hydroxyethyl)-4-(1H-2-methylimidazo[4,5-c]pyridin-1-ylmethyl)-phenylsulphonamide (1.52 g, 3.20 mmol) and triethylamine (893 μl, 6.40 mmol) in dry DCM was stirred under an inert atmosphere at 0° C. Methanesulphonyl chloride (372 μl, 4.80 mmol) was added dropwise and the reaction allowed to warm to ambient temperature. After a total reaction time of 4 hours the reaction was partitioned between DCM and water. The organic layer was separated, washed with water, dried over sodium sulphate, filtered and concentrated under reduced pressure to a yellow foam (1.77 g, 100%).

$^1$H-NMR; s (CDCl$_3$), 9.04 (1H, s), 8.38 (1H, d, J=5.5 Hz), 7.83 (2H, d, J=8.3 Hz), 7.16–7.13 (3H, m), 5.40 (2H, s), 4.41–4.30 (2H, m), 3.98–3.92 (1H, m), 3.50–3.36 (2H, m), 3.32–3.20 (4H, m), 3.02 (3H, s), 2.60 (3H, s), 1.51–1.45 (1 H, m), 1.36–1.31 (1H, m), 1.22–1.16 (1H, m), 0.93 (3H, t, J=7.0 Hz) and 0.83 (6H, t, J=6.4 Hz).

(c) N-(2-{[4-(R,S)-(4-Chlorophenyl)-phenyl-methyl ]piperazin-1-yl ]ethyl)-N-(S)-(1-ethoxymethyl-3-ethoxymethyl-3-methylbutyl)-4-(1H-2-methylimidazo[4,5-c]pyridin-1ylmethy)-phenylsulphonamide.

A solution of N-(S)-(1-ethoxymethyl-3-methylbutyl)-N-(2-ethyl-0-methane-sulphonate)-4-(1H-2-methylimidazo[4,5-c]pyridin-1-ylmethyl)-phenylsulphonamide (94 mg, 0.17 mmol), 4-chlorobenzhydrylpiperazine (98 mg, 0.34 mmol), triethylamine (29 μl, 0.20 mmol) and sodium iodide (catalytic) in THF (15 ml) was heated under reflux for 180 hours. THF was removed under reduced pressure. The residue was resuspended in DCM, washed with water (x3), dried over sodium sulphate, filtered and concentrated under reduced pressure. The product was purified by column chromatography on silica gel eluting with 3% methanol/DCM. Product containing fractions were combined and solvent removed to yield N-(2-{[4-(R,S)-(4-chlorophenyl)-phenyl-methyl]piperazin-1-yl}ethyl)-N-(S)-(1-ethoxymethyl-3-methylbutyl)-4-(1H-2-methylimidazo[4,5-c]pyridin-1 ylmethyl)-phenylsulphonamide as a white solid (80 mg, 65%).

$^1$H-NMR; (CDCl$_3$), 9.04 (1H, s), 8.38 (1H, d, J=5.5 Hz), 7.83 (2H, d, J=8.2 Hz), 7.34 (4H, m), 7.27–7.10 (8H, bm), 5.38 (2H, s), 4.19 (1H, s), 3.93 (1H, m), 3.28–3.15 (6, m), 2.65 (2H, bs), 2.59 (3H, s), 2.51 (6H, bs), 2.38 (2H, bs), 1.50 (1 H, m), 1.28 (2H, m), 0.89 (3H, t, J=6.9 Hz) and 0.82 (6H, m).

$^{13}$C-NMR; δ (CDCl$_3$), 142.1, 142.0, 141.1, 139.8, 139.2, 132.5, 129.1, 128.6, 128.5, 127.8, 127.2, 126.4, 104.6, 75.3, 71.3, 66.3, 58.7, 56.1, 53.7, 51.5, 46.8, 41.2, 39.6, 24.4, 22.8, 22.3, 14.9 and 14.0.

EXAMPLE 22

N-(2-{[3-(R,S)-(4-Chlorophenyl)-3-pyridin-2-yl-propyl]-methylaminoiethyl)-N-(S)-(1-ethoxymethyl-3-methylbutyl)-4-(1H-2-methylimidazo[4,5-c]pyridin-1-ylmethyl)-phenylsulphonamide.

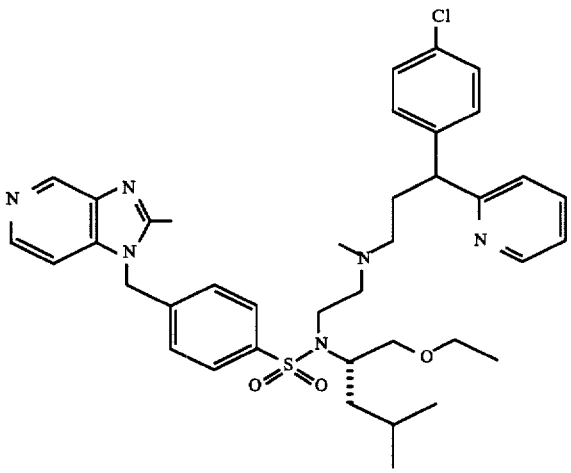

Using reaction conditions described for example 21(c) N-(S)-(1-ethoxymethyl-3-methylbutyl)-N-(2-ethyl-O-methane-sulphonate)-4-(1H-2-methylimidazo[4,5-c]pyridin-1-ylmethyl)-phenylsulphonamide (400 mg, 0.72 mmol) was reacted with N-methyl-(R,S)-3-(4-chlorophenyl)-3-(pyridin-2-yl)propylamine (378 mg, 1.45 mmol) to yield N-(2-{[3-(R,S)-(4-chlorophenyl)-3-pyridin-2-yl-propyl]-methylamino ethyl)-N-(S)-(1-ethoxymethyl-3-methylbutyl)-4-(1H-2-methylimidazo[4,5-c]pyridin-1-ylmethyl)-phenylsulphonamide (143 mg, 28%).

$^1$H-NMR; δ (CDCl$_3$), 9.03 (1H, s), 8.51 (1H, dd, J=5.1, 1.3 Hz), 8.36 (1H, d, J=5.6 Hz), 7.76 (2H, d, J=7.9 Hz), 7.53 (1H, td, J=7.7, 1.7 Hz), 7.27–7.25 (2H, m), 7.21 (2H, d, J=8.4 Hz), 7.12–7.05 (5H, m), 5.36 (2H, s), 4.09 (1H, t, J=7.6 Hz), 3.90–3.87 (1H, m), 3.24–3.05 (6H, m), 2.61–2.56 (1H, m), 2.58 (3H, s), 2.47–2.42 (1H, m), 2.4–2.35 (1H, m), 2.29–2.27 (2H, m), 2.21 (3H, s), 2.18–2.12 (1H, m), 1.49–1.45 (1H, m), 1.28–1.28 (1H, m), 1.20–1.14 (1H, m), 0.88 (3H, td, J=6.9, 4.9 Hz), 0.80–0.79 (3H, m) and 0.79–0.78 (3H, m).

$^{13}$C-NMR; δ (CDCl$_3$), 162.9, 153.3, 149.3, 142.2, 142.1, 142.0, 141.2, 140.1, 139.8, 139.2, 136.5, 132.1, 129.4, 128.6, 128.5, 126.4, 122.7, 121.5, 104.6, 71.3, 66.2, 58.0, 56.0, 55.6, 50.2, 46.8, 42.5, 41.9 and 14.0.

EXAMPLE 23

N-(3-{[3-(R,S)-(4-Chlorophenyl)-3-pyridin-2-yl-propyl$_1$-methylamino$_1$propyl)-N-(S)-(1-ethoxymethyl-3-methylbutyl)-4-(1H-2-methylimidazo[4,5-c]pyridin-1-ylmethyl)-phenylsulphonamide.

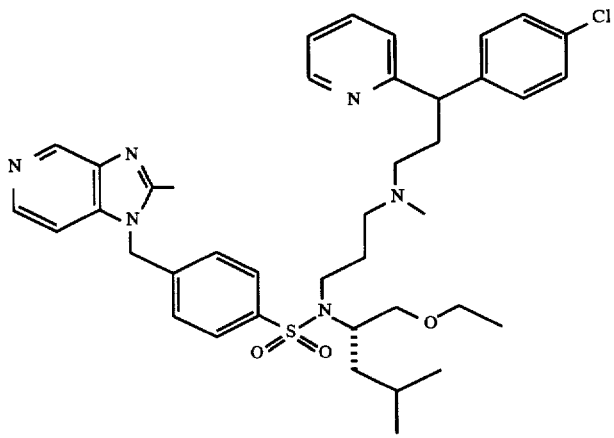

(a) N-Allyl-N-(S)-(1-ethoxymethyl-3-methylbutyl)-4-(1H-2-methylimidazo[4,5-c]pyridin-1-ylmethyl)-phenylsulphonamide.

A solution of (S)-(1-ethoxymethyl-3-methylbutyl)-4-(1H-2-methylimidazo[4,5-c]pyridin-1-ylmethyl)-phenylsulphonamide (5.00 g, 11.61 mmol) in dry DMF (75 ml), under an inert atmosphere was treated with sodium hydride (560 mg, 13.94 mmol).

The reaction was stirred at room temperature for 30 minutes before the addition of allyl bromide (1 ml, 11.61 mmol). After stirring for 18 hours solvent was removed under reduced pressure and the residue was partitioned between DCM and brine. The aqueous layer was back extracted with DCM. The organic layers were combined, dried over magnesium sulphate, filtered and concentrated to a dark red oil. The product was purified by column chromatography on silica gel eluting with 5–10% methanol/DCM. Product containing fractions were combined and solvent removed to yield N-allyl-N-(S)-(1-ethoxymethyl-3-methylbutyl)-4-(1H-2-methylimidazo-[4, 5-c]pyridin-1-ylmethyl)-phenylsulphonamide as a red oil (5.9 g, 100%).
1H-NMR; δ (CDCl$_3$), 9.05 (1H, s), 8.38 (1H, d, J=6 Hz), 7.85 (2H, d, J=10 Hz), 7.13 (1H, d, J=7 Hz), 7.11 (2H, d, J=10 Hz), 5.79–5.70 (1H, m), 5.39 (2H, s), 5.15 (1H, d, J=16 Hz), 5.03 (1H, d, J=12 Hz), 4.08–4.02 (1H, m), 3.80 (2H, d, J=7 Hz), 3.33–3.18 (4H, m), 2.60 (3H, s), 1.59–1.51 (1 H, m), 1.43–1.38 (1 H, m), 1.28–1.23 (1H, m), 0.92 (3H, t, J=7 Hz), 0.86 (6H, d, J=6 Hz).

(b) N-(S)-(1-Ethoxymethyl-3-methylbutyl)-N-(3-hydroxypropyl)-4-(1H-2-methylimidazo[4,5-c]pyridin-1-ylmethyl)-phenylsulphonamide.

N-Allyl-N-(S)-(1-ethoxymethyl-3-methylbutyl)-4-(1H-2-methylimidazo[4,5-c]pyridin-1-ylmethyl)-phenylsulphonamide (4.00 g, 8.50 mmol) was taken up in dry THF (75 ml) under an inert atmosphere. A solution of 9-borabicyclo[3.3.1]nonane (25 ml, 0.5M in THF, 12.5 mmol) was added and the reaction heated at 80° C. for 18 hours. The reaction was quenched by the sequential addition of ethanol (6 ml), sodium hydroxide solution (6M, 2 ml) and hydrogen peroxide solution (4 ml, 30%). THF was removed in a stream of argon and the residue partitioned between DCM and brine. The organic layer was separated, washed with brine, dried over magnesium sulphate, filtered and concentrated under reduced pressure to yield N-(S)-(1-ethoxymethyl-3-methylbutyl)-N-(3-hydroxypropyl)-4-(1H-2-methylimidazo[4,5-c]pyridin-1-ylmethyl)-phenylsulphonamide as a yellow oil (1.8 g, 43%).

1H-NMR; δ (CDCl$_3$), 9.03 (1H, s), 8.38 (1H, d, J=6 Hz), 7.82 (2H, d, J=9 Hz), 7.12–7.10 (3H, m), 5.39 (2H, s), 3.96–3.90 (1H, m), 3.74–3.65 (2H, m), 3.35–3.19 (6H, m), 2.60 (3H, s), 1.90–1.43 (3H, m), 1.37–1.26 (2H, m), 0.92 (3H, t, J=7 Hz), 0.82 (6H, t, J=8 Hz).

(c) N-(S)-(1-Ethoxymethyl-3-methylbutyl)-N-(3-propyl-O-methane-sulphonate)-[4-(1H-2-methylimidazo[4,5-c]pyridin-1-ylmethyl)-phenylsulphonamide.

A solution of N-(S)-(1-ethoxymethyl-3-methylbutyl)-N-(3-hydroxypropyl)-4-(1H-2-methylimidazo[4,5-c]pyridin-1-ylmethyl)-phenylsulphonamide (1.8 g, 3.68 mmol) in dry DCM (50 ml) was cooled in an ice-water bath and treated with triethylamine (1.0 ml, 7.37 mmol) and methanesulphonyl chloride (0.43 ml, 5.53 mmol) under an inert atmosphere. The reaction was stirred at room temperature for 18 hours before partitioning with brine. The organic layer was separated, washed with brine, dried over magnesium sulphate, filtered and concentrated under reduced pressure to a yellow oil. The product was purified by column chromatography on silica gel eluting with 5–15% methanol/DCM. Product containing fractions were combined and solvent removed to yield N-(S)-(1-ethoxymethyl-3-methylbutyl)-N-(3-propyl-O-methane-sulphonate)-4-(1H-2-methylimidazo[4,5-c]pyridin-1-ylmethyl)-phenylsulphonamide as a pale yellow oil (0.80 g, 38%).

1H-NMR; δ (CDCl$_3$), 8.96 (1H, s), 8.30 (1H, d, J=5.5 Hz), 7.74 (2H, d, J=9 Hz), 7.11 (1H, d, J=6 Hz), 7.09 (2H, d, J=9 Hz), 5.35 (2H, s), 4.19 (2H, t, J=6 Hz), 3.90–3.86 (1H, m), 3.25–3.12 (6H, m), 2.96 (3H, s), 2.54 (3H, s), 2.06–1.40 (3H, m), 1.31–1.26 (1H, m), 1.19–1.13 (1H, m), 0.87 (3H, t, J=6 Hz), 0.77 (3H, t, J=7 Hz), 0.76 (3H, d, J=7 Hz).

(d) N-(3-{[3-(R,S)-(4-Chlorophenyl)-3-pyridin-2-yl-propyl]-methylamino propyl)-N-(S)-(1-ethoxymethyl-3-methylbutyl)-4-(1 H-2-methylimidazo[4,5-c]pyridin-1-ylmethyl)-phenylsulphonamid N-(S)-(1-Ethoxymethyl-3-methylbutyl)-N-(3-propyl-0-methane-sulphonate)-4-(1H-2-methylimidazo[4,5-c]pyridin-1-ylmethyl)-phenylsulphonamide (400 mg, 0.71 mmol) was coupled to N-methyl-(R,S)-3-(4-chlorophenyl)-3-(pyridin-2-yl)propylamine (370 mg, 1.41 mmol) using conditions described for example 21 (c). N-(3-{[3-(R,S)-(4-Chlorophenyl)-2-yl-propyl]-methylamino lpropyl)-N-(S)-(1-ethoxymethyl-3-methylbutyl)-4-(1H-2-methylimidazo[4, 5-c]pyridin-1-ylmethyl)-phenylsulphonamide was isolated following chromatography as a yellow oil (173 mg, 34%).

1H-NMR; δ (CDCl$_3$), 9.04 (1H, s), 8.54 (1H, d, J=4.0Hz), 8.36 (1H, d, J=5.7 Hz), 7.82 (2H, d, J=8.3 Hz), 7.54 (1H, td, J=7.6, 1.9 Hz), 7.27–7.21 (4H, m), 7.12–7.07 (5H, m), 5.37 (2H, s), 4.08 (1 H, t, J=7.5 Hz), 3.94 (1 H, quintet, J=6.7 Hz), 3.28–3.22 (3H, m), 3.22–3.15 (1H, m), 3.15–3.05 (2H, m), 2.58 (3H, s), 2.47–2.10 (9H, bm), 1.84–1.64 (2H, bm), 1.51 (1H, septet, J=6.6 Hz), 1.33–1.22 (2H, m), 0.91 (3H, td, J=7.0, 1.0 Hz), 0.82 (3H, d, J=6.7 Hz) and 0.81 (3H, d, J=6.2 Hz).

$^{13}$C-NMR; δ (MeOD), 162.6, 155.3, 148.6, 141.8, 141.0, 140.8, 140.6, 140.3, 139.7, 139.1, 137.3, 132.0, 129.2, 128.3, 128.0, 127.0, 122.9, 121.8, 106.0, 70.9, 65.8, 56.0, 55.1, 54.3, 50.3, 46.3, 41.9, 40.8, 39.3, 31.1, 27.9, 24.2, 21.9, 21.2, 13.9 and 12.4.

EXAMPLE 24

N-(3-{[4-(R,S)-(4-Chlorophenyl)-phenyl-methyl]piperazin-1-yl}propyl)-N-(S)-(1-ethoxymethyl-3-methylbutyl)-4-(1H-2-methylimidazo[4,5-c]pyridin-1-ylmethyl)-phenylsulphonamide.

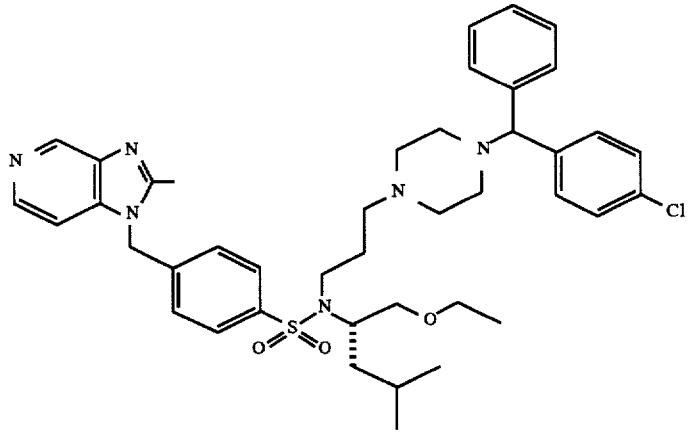

N-(S)-(1-Ethoxymethyl-3-methylbutyl)-N-(3-propyl-O-methane- sulphonate)-4-(1H-2-methylimidazo[4,5-c]pyridin-1-ylmethyl)-phenylsulphonamide (400 mg, 0.71 mmol) was coupled to 4-chlorobenzhydrylpiperazine (405 mg, 1.41 mmol) using conditions described for example 21(c). N-(3-([4-(R,S)-(4-Chlorophenyl)-phenyl-methyl]piperazin-1-yl}propyl)-N-(S)-(1-ethoxymethyl-3-methylbutyl)-[4-(1H-2-methylimidazo[4,5-c]pyridin-1ylmethyl)-phenylsulphonamide was isolated following chromatography as a colourless glass (221 mg, 41%).

$^{1}$H-NMR; δ (CDCl$_{3}$), 9.05 (1H, d, J=0.8 Hz), 8.38 (1H, d, J=5.4 Hz), 7.81 (2H, d, J=8.3 Hz), 7.36–7.34 (4H, m), 7.28–7.22 (4H, m), 7.18 (1H, t, J=7.3 Hz), 7.12–7.11 (1H, m), 7.09 (2H, m), 5.37 (2H, s), 4.18 (1H, s), 3.96–3.91 (1H, m), 3.29–3.16 (4H, m), 3.16–3.06 (2H, m), 2.59 (3H, s), 2.60–2.20 (9H, m), 1.95–1.86 (1H, bs), 1.85–1.76 (1H, m), 1.76–1.67 (1H, m), 1.53–1.46 (1H, m), 1.33–1.24 (2H, m), 0.92 (3H, t, J=6.8 Hz) and 0.83–0.80 (6H, m).

$^{13}$C-NMR; δ (CDCl$_{3}$), 153.3, 142.2, 142.1, 142.0, 141.4, 141.3, 140.1, 139.8, 139.1, 132.5, 129.2, 128.6, 128.5, 128.4, 127.8, 127.1, 126.3, 104.7, 75.4, 71.4, 66.2, 56.1, 55.7, 53.3, 51.8, 46.8, 42.5, 39.8, 28.2, 24.5, 22.8, 22.3, 14.9 and 13.9.

EXAMPLE 25

N-(S)-(1-Ethoxymethy-3-methylbutyl)-N-{[E]-3-[6-[3-Pyrrolidino-1-{4-tolyl}-prop-1E- enyl]-pyridin-2-yl)-prop-2-en-1-yl}-4-(1H-2-methylimidazo[4,5-c]pyridin-1-ylmethyl)-phenylsulphonamide.

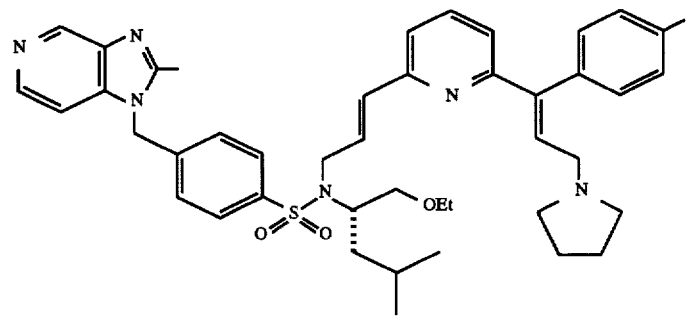

(a) (E)-3-(6-[3-Pyrrolidino-1-{4-tolyl}-prop-1E-enyl]-pyridin-2-yl)-prop-2-en-1-yl acetate.

Pyridine (110 μl, 1.36 mmol) was added to a solution of (E)-3-(6-[3-pyrrolidino-1-{4-tolyl}-prop-1E-enyl]-pyridin-2-yl)-prop-2-en-1y- o l (227 mg, e.68 mmoi, example 17(b)) in DCM (3 ml) under an inert atmosphere. Acetyl chloride (72 μl, 1.02 mmol) was added and the reaction stirred for 18 hours at room temperature. The reaction mixture was partitioned between DCM and brine. The organic layer was separated, dried over sodium sulphate, filtered and concentrated under vacuum to leave a brown oil. The product was purified by column chromatography on silica gel eluting with 5% methanol/DCM. Product containing fractions were combined and solvent removed to yield (E)-3-(6-[3-pyrrolidino-1-{4-tolyl}-prop-1E-enyl]-pyridin-2-yl)-prop-2-en-1-yl acetate as a brown gum (184 mg, 73%).

EXAMPLE 26

N-Cyclohexyl-N-{(E)-3-(6-[3-pyrrolidino-1-{4-tolyl}-prop-1E-enyl]-pyridin-2-yl)-prop-2-en-1-yl}-4-(1H-2-methylimidazo[4,5-c]pyridin-1-ylmethyl)-phenylsulphonamide.

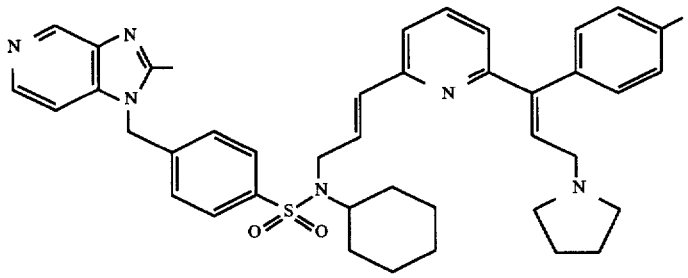

$^1$H-NMR; (CDCl$_3$), 7.49 (1H, t, J=7.8 Hz), 7.24 (2H, d, J=7.9 Hz), 7.18–7.11 (2H, m), 7.06 (2H, d, J=7.9 Hz), 6.91–6.66 (3H, m), 4.79 (2H, dd, J=5.4, 0.7 Hz), 3.72 (2H, m), 3.20 (4H, bm), 2.40 (3H, s), 2.12 (3H, s), 2.11–2.02 (4H, m).

(b) N-(S)-(1-Ethoxymethyl-3-methylbutyl)-N-((E)-3-(6-[3-pyrrolidino-1-{4-tolyl}-prop-1E-enyl]-pyridin-2-yl)-prop-2-en-1-yl}-4-(1H-2-methylimidazo[4,5-c]pyridin-1-ylmethyl)-phenylsulphonamide.

Sodium hydride (17 mg, 60% oil, 0.42 mmol) was added to a solution of (S)-(1-ethoxymethyl-3-methylbutyl)-4-(1H-2-methylimidazo[4,5-c]pyridin-1-ylmethyl)-phenylsulphonamide (173 mg, 0.4 mmol) in a mixture of THF/DMF (3/1, 4 ml) under an inert atmosphere. (E)-3-(6-[3-Pyrrolidino-1-{4-tolyl}-prop-1E-enyl )-pyridin-2-yl)-prop-2-en-1-yl acetate (100 mg, 0.27 mmol) was taken up in THF (2 ml), treated with tetrakis(triphenylphosphine)palladium(O) (16 mg, 0.014 mmol) and stirred at room temperature for 1 hour. The solution was transferred by cannula to the reaction mixture which was then heated at 60° C. for 48 hours. The reaction mixture was concentrated under reduced pressure to a brown oil. The residue was taken up in DCM, washed with saturated sodium bicarbonate solution, dried over sodium sulphate, filtered and concentrated. The product was purified by column chromatography on silica gel, eluting with a gradient of 2–50% methanol/DCM. Product containing fractions were combined and solvent removed to yield N-(S)-(1-ethoxymethyl-3-methylbutyl)-N-{(E)-3-(6-[3-pyrrolidino-1-{4-tolyl}-prop-1E-enyl]-pyridin-2-yl)-prop-2-en-1-yl}-4-(1H-2-methylimidazo[4,5-c]pyridin-1-ylmethyl)-phenylsulphonamide as a brown gum (94 mg, 47%).

$^1$H-NMR; δ (MeOD), 8.83 (1H, s), 8.27 (1H, d, J=5.7 Hz), 7.85 (2H, d, J=8.4Hz), 7.51 (2H, m), 7.27 (4H, m), 7.14 (1H, d, J=7.7 Hz), 7.08 (2H, d, J=8.0Hz), 6.99 (1H, t, J=7.1 Hz), 6.67 (1H, m), 6.62 (2H, d, J=15.9 Hz), 5.60 (2H, s), 4.10 (1H, m), 4.02 (2H, d, J=6.1 Hz), 3.53 (2H, d, J=7.1 Hz), 3.22 (4H, m), 2.91 (4H, bm), 2.60 (3H, s), 2.39 (3H, s), 1.89 (4H, br m), 1.62 (1H, m), 1.48 (1 H, m), 1.25 (1 H, m), 0.86 (6H, m) and 0.79 (3H, d, J=6.7 Hz).

13C-NMR; δ (MeOD), 156.7, 155.3, 154.4, 145.1, 141.1, 141.0, 140.7, 140.2, 139.7, 139.1, 137.7, 136.9, 134.2, 132.4, 131.7, 129.3, 129.1, 129.0, 129.0, 128.2, 126.9, 124.1, 121.0, 119.8, 106.0, 70.9, 65.8, 56.2, 53.5, 53.4, 46.4, 45.2, 24.0, 22.7, 22.0, 21.0, 19.9, 14.0 and 12.5.

(a) N-Cyclohexyl-4-(1H-2-methylimidazo[4,5-c]pyridin-1-ylmethyl)-phenyl sulphonamide.

N-Cyclohexyl-4-(1H-2-methylimidazo[4,5-c]pyridin-1-ylmethyl)-phenyl sulphonamide was prepared using a procedure analogous to that described for the regioselective synthesis of S-(1-ethoxymethyl-3-methylbutyl)-4-(1H-2-methylimidazo[4,5-c]pyridin-1-ylmethyl)-phenylsulphonamide in the international patent application WO 92/03422.

$^1$H-NMR; δ (CDCl$_3$), 9.05 (1H, d, J=0.7 Hz), 8.39 (1H, d, J=5.5 Hz), 7.84 (2, d,H J=8.5 Hz), 7.17–7.13 (3H, m), 5.30 (2H, s), 4.75 (1H, bd, J=6.9 Hz), 3.17–3.14 (1H, m), 2.60 (3H, s), 1.88–1.50 (6H, m), 1.26–1.06 (4H, m).

(b) N-Cyclohexyl-N-{(E)-3-(6-[3-pyrrolidino-1-{4-tolyl}-prop-1E-enyl]-pyridin-2-yl)-prop-2-en-1-yl}-4-(1H-2-methylimidazo[4,5-c]pyridin- 1-ylmethyl)-phenylsulphonamide N-Cyclohexyl-4-(1H-2-methylimidazo[4,5-c]pyridin-1-ylmethyl)-phenyl sulphonamide (494 mg, 1.29 mmol) was coupled to (E)-3-(6-[3-pyrrolidino-1-{4-tolyl}-prop-1E-enyl]-pyridin-2-yl)-prop-2-en-1-yl acetate (400 mg, 1.07 mmol) using the procedure described for example 25(b) to yield N-cyclohexyl-N-{(E)-3-(6-[3-pyrrolidino-1-{4-tolyl}-prop-1E-enyl]-pyridin-2-yl)-prop-2-en-1-yl}-4-(1H-2-methylimidazo[4,5-c]pyridin-1-ylmethyl)-phenylsulphonamide as a white foam (215 mg, 29%).

$^1$H-NMR; δ (CDCl$_3$), 9.02 (1H, s), 8.34 (1H, d, J=5.5 Hz), 7.80 (2H, d, J=8.3 Hz), 7.43 (1H, t, J=7.8 Hz), 7.24–7.04 (9H, m), 6.74–6.57 (3H, m), 5.39 (2H, s), 4.01 (2H, d, J=5.1 Hz), 3.74–3.66 (1H, m), 3.48 (2H, d, J=7.1 Hz), 2.94–2.87 (4H, m), 2.55 (3H, s), 2.40 (3H, s), 1.91 (4H, bs), and 1.75–0.98 (10H, m).

$^{13}$C-NMR; δ (CDCl$_3$), 156.5, 154.2, 153.4, 142.2, 142.1, 141.8, 140.3, 139.9, 139.5, 137.7, 136.8, 134.4, 132.2, 132.0, 129.5, 128.0, 126.9, 121.2, 120.2, 104.8, 58.4, 54.0, 53.6, 46.9, 45.3, 31.9, 26.1, 25.2 and 14.1.

EXAMPLE 27

N-Methyl-N-{(E)-3-(6-[3-pyrrolidino-1-{4-tolyl}-prop-1E-enyl]-pyridin-2-yl)-prop-2-1-yl}-4-(1H-2-methylimidazo[4,5-c]pyridin-1-ylmethyl)-phenylsulphonamide.

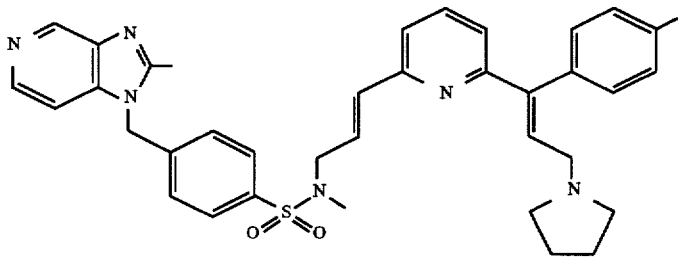

(a) N-Methyl-4-(1H-2-methylimidazo[4,5-c]pyridin-1-ylmethyl)-phenyl sulphonamide.

N-Methyl-4-(1H-2-methylimidazo[4,5-c]pyridin-1-ylmethyl)-phenylsulphonamide was prepared using a procedure analogous to that described for the regioselective synthesis of S-(1-ethoxymethyl-3-methylbutyl)-[4-(1H-2-methylimidazo[4,5-c]pyridin-1-ylmethyl)-phenylsulphonamide in the international patent application WO 92/03422.

¹H-NMR; δ (CDCl₃), 9.07 (1H, s), 8.40 (1H, d, J=6.8 Hz), 7.85 (2 H, d, J=8.9 Hz), 7.16 (3H, m), 5.42 (2H, s), 4.95 (1H, m), 2.70 (3H, d, J=5.5 Hz), 2.61 (3H, s).

(b) N-Methyl-N-{(E)-3-(6-[3-pyrrolidino-1-{4-tolyl}-prop-1E-enyl]-pyridin-2-yl)-prop-2-en-1-yl}-4-(1H-2-methylimidazo[4,5-c]pyridin-1-ylmethyl)-phenylsulphonamide.

N-Methyl-4-(1H-2-methylimidazo[4,5-c]pyridin-1-ylmethyl)-phenylsulphonamide (381 mg, 1.21 mmol) was coupled to (E)-3-(6-[3-pyrrolidino-1-{4-tolyl}-prop-1E-enyl]-pyridin-2-yl)-prop-2-en-1-yl acetate (300 mg, 0.80 mmol) using the procedure described for example 25(b) to yield N-methyl-N-{(E)-3-(6-[3-pyrrolidino-1-{4-tolyl}-prop-1E-enyl]-pyridin-2-yl)-prop-2-en-1-yl}-4-(1H-2-methylimidazo[4,5-c]pyridin-1-ylmethyl)-phenylsulphonamide as a pale brown solid (226 mg, 44%).

¹H-NMR; δ (MeOD), 8.75 (1H, s), 8.19 (1H, d, J=5.8 Hz), 7.72 (2H, d, J=8.3 Hz), 7.48 (1H, t, J=7.8 Hz), 7.41 (1H, d, J=6.0 OHz), 7.20 (5H, m), 6.98 (2H, d, J=8.1 Hz) 6.90 (1H, t, J=7.2 Hz), 6.73 (1H, d, J=7.2 Hz), 6.56 (2H, m), 5.55 (2H, s), 3.74 (2H, m), 3.68 (2H, d, J=7.2 Hz), 3.10 (4H, m), 2.63 (3H, s), 2.51 (3H, s), 2.29 (3H, s) and 1.89 (4H, m).

¹³C-NMR; δ (MeOD), 157.7, 156.9, 155.6, 148.3, 142.5, 142.2, 142.2, 141.1, 140.5, 139.5, 138.7, 138.6, 135.1, 134.3, 130.6, 129.5, 128.6, 122.9, 122.6, 122.0, 107.3, 54.5, 54.3, 53.1, 49.8, 49.5, 47.7, 35.3, 24.0, 21.3 and 13.8.

EXAMPLE 28

(S)-4-Methyl-2-([4-1H-2-methylimidazo[4,5-c]pyridin-1-ylmethyl)-phenylsulphonyl]-(E)-{3-[6-(3-pyrrolidin-1-yl-{4-tolyl}-prop-1E-enyl]-prop-2-enyl}-amino)-pentanoic acid ethyl ester.

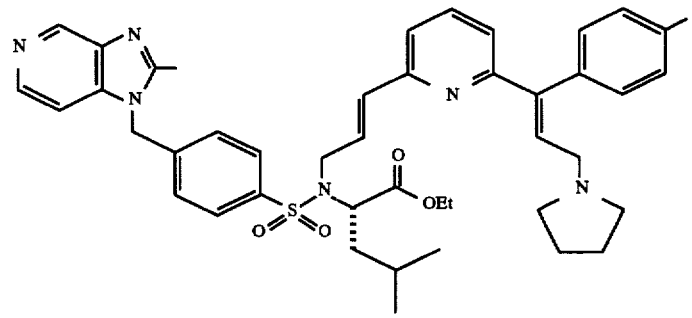

Sodium hydride (35 mg, 60% oil, 0.88 mmol) was added to a solution of (S)-4-Methyl-2-([4-1H-2-methylimidazo[4,5-c]pyridin-1-ylmethyl)-phenylsulphonyl]-amino)-pentanoic acid ethyl ester (381 mg, 0.86 mmol) in a mixture of THF/DMF (3/1, 15 ml) under an inert atmosphere. (E)-3-(6-[3-Pyrrolidino-1-{4-tolyl}-prop-1E-enyl]-pyridin-2-yl)-prop-2-en-1-yl acetate (213 mg, 0.57 mmol) was taken up in a mixture of THF/DMF (3/1, 5 ml), treated with tetrakis(triphenylphosphine)palladium(0) (35 mg, 0.03 mmol) and stirred at room temperature for 1 hour. The solution was transferred by cannula to the reaction mixture which was then heated at 60° C. for 48 hours. The reaction mixture was concentrated under reduced pressure to a brown oil. The residue was taken up in DCM, washed with saturated sodium bicarbonate solution, dried over sodium sulphate, filtered and concentrated. The product was purified by column chromatography on silica gel, eluting with a gradient of 2–20% methano/VDCM. Product containing fractions were combined and solvent removed to yield (S)-4-methyl-2-([4-1H-2-methylimidazo[4,5-c]pyridin-1-ylmethyl)-phenylsulphonyl]-(E)-{3-[6-(3-pyrrolidin-1-yl]-{4-tolyl}-prop-1E-enyl]-prop-2-enyl}-amino)-pentanoic acid ethyl ester as a yellow/brown solid (188 mg, 44%).

$^1$H-NMR; δ (CDCl$_3$), 8.57 (1H, s), 8.39 (1H, d, J=5.6 Hz), 7.77 (2H, d, J=8.33 Hz), 7.60 (1H, dd, J=5.5, 0.8 Hz), 7.40 (1H, 1H, t, J=7.8 Hz), 7.17 (4H, m), 7.06 (4H, m), 6.65 (3H, m), 5.43 (2H, s), 4.57 (1H, ), 4.10 (1H, ), 3.95 (1H, ), 3.82 (2H, m), 3.28 (2H, d), 2.66 (4H, m), 2.56 (3H, s), 2.36 (3H, s), 1.79 (4H, m), 1.68 (3H, m), 0.98 (3H, t, J=7.0 Hz), 0.92 (3H, d, J=6.0 Hz) and 0.81 (3H, d, J=6.1 Hz).

$^{13}$C-NMR; δ (CDCl$_3$), 171.0, 157.1, 155.0, 153.9, 147.7, 142.9, 142.2, 139.9, 139.7, 137.1, 136.5, 134.8, 132.7, 132.1, 130.8, 129.5, 129.1, 128.3, 127.6, 126.6, 120.9, 119.4, 113.9, 61.0, 58.1, 54.1, 53.6, 47.2, 46.9, 38.9, 24.2, 23.4, 22.5, 21.1 and 13.7.

PHARMACOLOGY EXAMPLE 1

Histamine Induced Bronchoconstriction in the Anaesthetised Guinea Pig

Following oral administration of test compound or vehicle by oral gavage, male Dunkin-Hartley guinea pigs (350–400 g) were anaesthetised by intraperitoneal injection of 60 mgkg$^{-1}$ sodium pentobarbitone (Sagatal, May & Baker UK). Through a midline incision of the neck, the trachea was cannulated and connected to a small animal respirator (Harvard, UK). Animals were artificially ventilated at a rate of 30 breaths per minute with a tidal volume of 8–10 ml to give a resting tracheal inflation pressure of 15 mmHg as measured by a physiological pressure transducer (type P23XL, Spectramed USA) connected to a side arm of the respiratory circuit.

A jugular vein was cannulated for the administration of propranolol and for the infusion of histamine. A carotid artery was cannulated for the measurement of arterial blood pressure via a physiological pressure transducer (type P23XL, Spectramed USA). Blood pressure and tracheal inflation pressure were recorded on a thermal array chart recorder (type TA4000, Gould Electronics UK).

Following a suitable equilibration period, propranolol (1 mgkg$^{-1}$ i.v. & 3 mgkg$^{-1}$ s.c. Sigma Chemical Co. UK) was administered to inhibit any resulting catecholamine release following histamine administration.

Histamine infusion (10 μgkg$^{-1}$min$^{-1}$ at a rate of 10 mlhr$^{-1}$ using a perfusion pump type Perfuser securer FT, B. Braun Germany) was started at the one hour time point following oral administration of the test compound or vehicle. Changes in tracheal inflation pressure and blood pressure of drug treated animals were compared with changes from vehicle treated animals and ED$_{50}$ values determined. One dose of test compound was investigated per animal.

| Example | ED$_{50}$ mgkg$^{-1}$, p.o. |
|---|---|
| 6 | 6.5 |
| 8 | 0.16 |
| 25 | 0.50 |

PHARMACOLOGY EXAMPLE 2

PAF Induced Bronchoconstriction in the Anaesthetised Guinea Pig

Following oral administration of test compound or vehicle, male Dunkin-Hartley guinea pigs (350–400 g) were anaesthetised by intraperitoneal injection of 60 mgkg$^{-1}$ sodium pentobarbitone (Sagatal, May & Baker UK). Through a midline incision of the neck, the trachea was cannulated and connected to a small animal respirator (Harvard, UK). Animals were artificially ventilated at a rate of 30 breaths per minute with a tidal volume of 8–10 ml to give a resting tracheal inflation pressure of 15mmHg as measured by a physiological pressure transducer (type P23XL, Spectramed USA) connected to a side arm of the respiratory circuit.

A jugular vein was cannulated for the administration of a bolus dose of propranolol and for the later administration of bolus PAF. A carotid artery cannulated for the measurement of arterial blood pressure via a physiological pressure transducer (type P23XL, Spectramed USA). Blood pressure and tracheal inflation pressure were recorded on a thermal array chart recorder (type TA4000, Gould Electronics UK).

Propranolol (1 mgkg$^{-1}$ i.v. & 3 mgkg$^{-1}$ s.c. Sigma Chemical Co. UK) was administered 10 minutes before PAF in order to prevent the bronchodilatory activity of catecholamines which may be released in response to PAF administration. PAF (100 ngkg$^{-1}$ i.v. bolus) was administered at the one hour time point following oral administration of the test compound or vehicle.

Changes in tracheal inflation pressure and blood pressure of drug treated animals were compared with changes from vehicle treated animals and percentage inhibition determined. One dose of test compound was investigated per animal.

Results

| Example | % Inhibition at 10 mgkg$^{-1}$, p.o. |
|---|---|
| 6 | 40 |
| 8 | 46 |
| 25 | 50 |

PHARMACOLOGY EXAMPLE 3

Inhibition of [$^3$H]-Pyrilamine Binding to Histamine-1 Receptors on Hela-S3 Cells The inhibition of [$^3$H]-pyrilamine binding to histamine-1 receptors on Hela-S3 cells (American Type Culture Collection) was determined by isotopic labelling and filtration techniques. A suspension of the cells in buffer (25 ml, 0.5% Bovine Serum Albumin, 0.1% sodium azide, phosphate buffered saline (PBS)) was centrifuged at 1000 rpm for 5 minutes in a JOUAN CR 422 centrifuge, collected, resuspended in buffer (25 ml) and spun again. The cells were counted using a haemocytometer and resuspended in buffer to provide a final concentration of 4.5×10$^6$ cells ml$^{-1}$. A portion of the Hela S3 cell suspension (1 ml) was added to each assay tube containing 25 μl of vehicle (50% DMSO/buffer) or 25 μl of solution containing test compound (dissolved in DMSO and diluted with sufficient PBS to give a final test concentration of 1 μM) and 25 μl 0f [$^3$H]-pyrilamine (supplied by Amersham International and diluted with PBS to 3 nM). The tubes were mixed and incubated at 37° C. for 30 minutes. The tubes were then spun at 4° C. at 2000 rpm for 2 minutes. The supernatant was removed and the cells resuspended in buffer (repeated x2). The cells were suspended in 300 μl of a 2:1 solution of 1M sodium hydroxide and 1% sodium dodecyl sulphate. The tubes were left overnight before the contents were tranferred to a scintillation vial, treated with 10 ml, OPTIPHASE MP scintillation fluid (OPTIPHASE MP is a trade mark) and the radioactivity counted in a scintillation counter. Non-displcable binding (NDB) was determined using Astemizole ($5 \times 10^{-5}$ M) in place of test compounds. Defining the counts for total binding from the vehicle control sample as "TB" and the counts for total binding with antagonist as "TBA", the percentage specific binding (%SB) can be determined from the following equation.

$$\% SB = \frac{(TBA - NDB)}{(TB - NDB)} \times 100\%$$

Results

| Example | % Specific Binding at 1 μM |
|---------|----------------------------|
| 2       | 57                         |
| 4       | 34                         |
| 6       | 79                         |
| 17      | 47                         |
| 23      | 33                         |
| 25      | 55                         |

PHARMACOLOGY EXAMPLE 4

Inhibition of PAF-Induced Platelet Aggregation

Male New Zealand White rabbits (3.0–3.5 kg) were anaesthetised by intravenous administration of sodium pentobarbitone, 18 mg.ml$^{-1}$, via a marginal ear vein. The trachea was exposed and connected to a respiratory pump (Havard UK) to provide artificial ventilation. A carotid artery was exposed and cannulated and the animal was exsanguinated. Whole blood was collected in a syringe containing tri-sodium citrate (3.8% w/v) to a ratio of 1 part citrate:9 parts blood.

Collected blood was centrifuged at 180×g for 15 minutes at room temperature (21° C.) to prepare platelet-rich plasma (PRP). The remaining blood was then centrifuged at 1800×g for 10 minutes at room temperature to obtain platelet poor plasma (PPP).

Platelet count of the PRP was measured using a Technicon H1 blood cell differential analyser (Bayer Diagnostics UK) and adjusted with PPP to obtain a final platelet count of 500.000 platelets per μl of plasma, this being the normal physiological platelet count for rabbits. Corrected PRP was left to equilibrate at room temperature for 30 minutes before use.

Aggregation studies were carried out using 4-channel aggregometer (PAP-4C, BioData USA) as follows: 400 μl aliquots of PRP were placed in siliconised cuvettes and incubated to 37° C. for 1 to 2 minutes in the heating block of the aggregometer. Baseline (100% aggregation) was set up using PPP (500 μl in a siliconised cuvette). The PRP was placed into a measuring well of the aggregometer, and a stir bar was added. The sample was stirred at 1000 rpm. The machine was activated to set the 0% aggregation level. Test compound or vehicle (50 μl) was added to the PRP, where any effects on the baseline was noted. PAF (100 ng.ml$^{-1}$ as 50 μl aliqout) was added to the PRP 3 minutes after test compound or vehicle. Aggregation was measured for a further 4 minutes after PAF addition and the maximum aggregation over the 4 minutes was recorded.

The investigation of different concentrations of test compound was performed in triplicate. Data were expressed as 0% aggregation of the sample and test compound data were compared to vehicle data to obtain % inhibition of the PAF-induced aggregation from which IC$_{50}$ values could be determined.

PAF was made up in sterile saline (NaCl 0.9% w/v) containing BSA (0.25% w/v) from an initial stock solution (10 mg.ml$^{-1}$ in EtOH). Test compounds were made up as $1 \times 10^{-3}$M stock solutions in sterile saline containing molar equivalents of 1N HCl (v/v) or in DMSO.

Results

| Example | PAF-Induced Platelet Aggregation IC$_{50}$ (nM) |
|---------|------------------------------------------------|
| 2       | 2100                                           |
| 4       | 190                                            |
| 6       | 252                                            |
| 17      | 115                                            |
| 23      | 300                                            |
| 25      | 420                                            |

We claim:

1. A compound of formula (II)

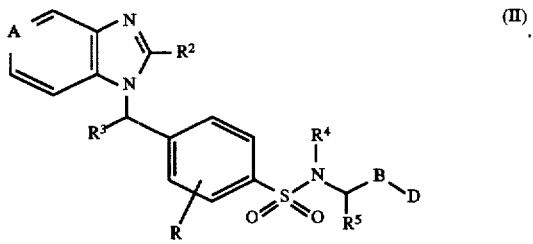

wherein

A represents =N—, =CH— or =CR$^1$—, wherein R$^1$ represents hydrogen, C$_1$–C$_6$ alkyl, C$_2$–C$_6$ alkenyl, halogen, —CN, —CO$_2$H, —CO$_2$(C$_1$–C$_6$ alkyl), —CONH$_2$, —CHO, —CH$_2$OH, —CF$_3$, C$_1$–C$_6$ alkoxy, C$_1$–C$_6$ alkylsulphanyl, C$_1$–C$_6$ alkylsulphinyl, C$_1$–C$_6$ alkylsulphonyl, —NH$_2$, —NHCOCH$_3$, or —NO$_2$; provided that when A represents =N— the resulting imidazo[4,5-c]pyridinyl bicyclic ring system is optionally substituted in the 4- and/or 6-positions by methyl;

R represents hydrogen, C$_1$–C$_6$ alkyl, C$_2$–C$_6$ alkenyl, halogen or C$_1$–C$_6$ alkoxy;

R$^2$ represents hydrogen, C$_1$–C$_6$ alkyl, C$_2$–C$_6$ alkenyl, C$_1$–C$_6$ alkoxy, C$_{1-C6}$ alkylsulphanyl, cyclopropyl, C$_1$–C$_6$ hydroxyalkyl, (C$_1$–C$_6$ alkyl)$_2$N—, (C$_1$–C$_6$ alkyl)$_2$ N(C$_1$–C$_6$ alkyl)— or —CF$_3$;

R$^3$ represents hydrogen, C$_1$–C$_6$ alkl, C$_2$–C$_6$ alkenyl, C$_2$–C$_6$ alkynyl, —CO$_2$(C$_1$–C$_6$ alkyl), C$_1$–C$_6$ alkoxy, C$_1$–C$_6$ alkylsulphanyl, (C$_1$–C$_6$ alkoxy)(C$_1$–C$_6$ alkyl)—, (C$_1$–C$_6$ alkylsulphanyl)(C$_1$–C$_6$ alkyl)—, (phenyl)(C$_1$–C$_6$ alkyl)—, or phenylsulphanyl;

R$^4$ represents hydrogen, C$_1$–C$_6$ alkyl, C$_2$–C$_6$ alkenyl, C$_2$–C$_6$ alkynyl, C$_1$–C$_6$ alkylcarbonyl, —CO$_2$(C$_1$–C$_6$ alkyl), (phenyl)C$_1$–C$_6$ alkylcarbonyl—, —C(=O)O—(C$_1$–C$_6$ alkyl)-(phenyl), (C$_1$–C$_6$ alkoxy)(C$_1$–C$_6$ alkyl)—, (C$_1$–C$_6$ alkylsulphanyl)(C$_1$–C$_6$ alkyl)—, —(C$_1$–C$_6$ alkyl)—C(=O)O—(C$_1$–C$_6$ alkyl), (C$_3$–C$_8$)cycloalkyl, (C$_4$–C$_8$)cycloalkenyl, or a group of formula (III)

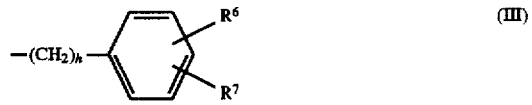

wherein h is 0 or an integer from 1 to 3, and each of R$^6$ and R$^7$ is independently hydrogen, C$_1$–C$_6$ alkyl, C$_2$–C$_6$ alkenyl, C$_2$–C$_6$ alkynyl, halogen, —CN, —CO$_2$H, —CO$_2$(C$_1$–C$_6$ alkyl), —CONH$_2$, —CONH(C$_1$–C$_6$ alkyl), —CON($C_1$–$C_6$ alkyl)$_2$, —CHO, —CH$_2$OH, —CF$_3$, $C_1$–$C_6$ alkoxy, $C_1$–$C_6$ alkylsulphanyl, $C_1$–$C_6$ alkylsulphinyl, $C_1$–$C_6$ alkylsulphonyl, —NH$_2$, or —NHCOCH$_3$;

$R^5$ represents hydrogen, halogen, $C_1$–$C_6$ alkyl optionally substituted with one or more halogen atoms, $C_2$–$C_6$ alkenyl, $C_2$–$C_6$ alkynyl, ($C_1$–$C_6$ alkyl)—C(=O)O—($C_1$–$C_6$ alkyl), ($C_1$–$C_6$ alkoxy)$C_1$–$C_6$ alkyl, ($C_1$–$C_6$ alkylsulphanyl)$C_1$–$C_6$ alkyl, -($C_1$–$C_6$ alkyl)N($C_1$–$C_6$alkyl)$_2$, ($C_3$–$C_8$)cycloalkyl, ($C_4$–$C_8$) cycloalkenyl, (($C_3$–$C_8$)cycloalkyl)$C_1$–$C_6$ alkyl, (($C_4$–$C_8$)cycloalkenyl)$C_1$–$C_6$ alkyl, (($C_3$–$C_8$) cycloalkyl)—O—($C_1$–$C_6$ alkyl), (($C_4$–$C_8$) cycloalkenyl)—O—($C_1$–$C_6$ alkyl), (($C_3$–$C_8$) cycloalkyl)—S—($C_1$–$C_6$ alkyl), (($C_4$–$C_8$) cycloalkenyl)—S—($C_1$–$C_6$ alkyl), a side chain of a naturally occurring amino acid, or a group of formula (III) as defined above;

B represents a bond, or a straight saturated or unsaturated hydrocarbon chain of from 1 to 6 carbon atoms which may additionally include from 1 to 3 non-adjacent hetero atoms of the groups selected from —O—, —S—, —N($R^4$)— wherein $R^4$ is as defined above, —S(O)—, —S(O$_2$)—, and —S(O$_2$)N($R^4$)— wherein $R^4$ is as defined above, and in which one or more carbon atoms of the chain are optionally substituted by oxo, hydroxy, $C_1$–$C_4$ alkyl, phenyl, or -phenyl($C_1$–$C_4$ alkyl);

D represents a group of formula (IV), (V), (VI), (VII) or (VIIA)

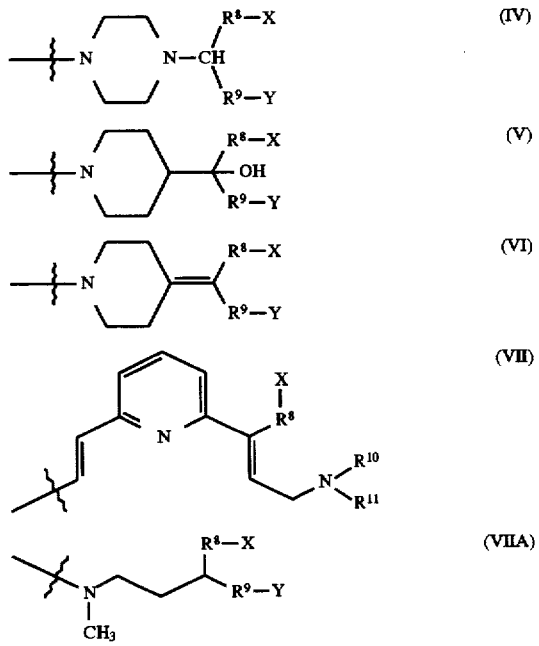

wherein $R^8$ and $R^9$ are the same or different and each represents an optionally substituted divalent phenylene group or an optionally substituted 5–6 membered monocyclic divalent heteroarylene group containing at least one nitrogen, oxygen or sulphur atom, wherein any optional substituents are selected from $C_1$–$C_6$ alkyl, $C_2$–$C_6$ alkenyl, HOOC—($C_2$–$C_6$ alkenyl), halogen and $C_1$–$C_6$ alkoxy groups, and X and Y are independently hydrogen or when taken together in groups (IV), (V), (VI) or (VIIA) represent a divalent group selected from —CH$_2$CH$_2$—, —CH=CH—, —CH$_2$O— and —COCH$_2$—; and $R^{10}$ and $R^{11}$ are independently $C_1$–$C_6$ alkyl or together with the nitrogen atom to which they are attached form a non-aromatic 5–7 membered heterocyclic ring;

provided that when D is a group IV, V, VI or VIIA in which $R^8$ and $R^9$ are both phenylene groups and substituents X and Y are both hydrogen, then the group B does not include a carbonyl group bonded directly to D;

or a pharmaceutically or veterinarily acceptable acid addition salt or hydrate thereof.

2. A compound as claimed in claim 1 wherein the group B has the formula —(CH$_2$)$_i$—, —CO—, —COX$^1$(CH$_2$)$_i$—, —COX$^1$(CH$_2$)$_i$Y$^1$CO—, —COX$^1$(CH$_2$)$_i$Y$^1$(CH$_2$)$_j$—, —(CH$_2$)$_i$X$^1$CO—, —COX$^1$(CH$_2$)$_i$Y$^1$(CH$_2$)$_j$ZCO—, —CO(CH$_2$)$_i$—, —(CH$_2$)$_i$X$^1$(CH$_2$)$_j$—, —(CH$_2$)$_i$X$^1$(CH$_2$)$_j$Y$^1$(CH$_2$)$_j$—, —(CH$_2$)$_i$X(CH$_2$)$_j$Y$^1$CO—, —(CH$_2$)$_i$X$^1$CO (CH$_2$)$_j$—, —X$^1$(CH$_2$)$_i$—, —S(CH$_2$)$_i$—, —SO(CH$_2$)$_i$—, —SO$_2$(CH$_2$)$_i$—, or —SO$_2$X$^1$(CH$_2$)$_i$—, wherein X$^1$, Y$^1$ and Z independently represent —O— or —NR$^4$— where R$^4$ is as defined above in formula (II), and i and j are independently 0 or an integer from 1 to 6, provided that no more than 6 carbon atoms are present in the linear chain represented by the foregoing formulae, and provided that where both X$^1$ and Y$^1$ are present in the linker group B then i is an integer from 1 to 6.

3. A compound as claimed in claim 1 or claim 2 wherein A is =N—.

4. A compound as claimed in any of the preceding claims wherein $R^2$ represents methyl.

5. A compound as claimed in claim 1 or claim 2 wherein $R^3$ represents hydrogen.

6. A compound as claimed in claim 1 or claim 2 wherein $R^4$ represents hydrogen, a —$C_1$–$C_6$ alkyl group, a —$C_2$–$C_6$ alkenyl group, a $C_3$–$C_8$ cycloalkyl group, a ($C_1$–$C_6$ alkoxy) ($C_1$–$C_6$ alkyl)— group, a —($C_1$–$C_6$ alkyl)—C(=O)O—($C_1$–$C_6$ alkyl) group, or a group of formula (III).

7. A compound as claimed in claim 6 wherein $R^4$ represents methyl, ethyl, iso-propyl, allyl, cyclohexyl, cyclopentyl, cyclopropyl, 1-ethoxymethyl-3-methylbut-1-yl, or 1-ethoxycarbonyl-3-methylbut-1-yl.

8. A compound as claimed in claim 1 or claim 2 wherein $R^5$ represents hydrogen, a $C_1$–$C_6$ alkyl group, a $C_2$–$C_6$ alkenyl group, a ($C_1$–$C_6$ alkyl)$C_3$–$C_8$ cycloalkyl group, a side chain of a naturally occurring amino acid or a group of formula (III).

9. A compound as claimed in claim 8 wherein $R^5$ represents methyl, ethyl, n-butyl, i-butyl, sec-butyl, t-butyl, allyl, cyclopropylmethyl, cyclopentylmethyl, cyclohexylmethyl or the side chain of leucine, isoleucine, phenylalanine, valine, tryptophan, methionine or tyrosine.

10. A compound as claimed in claim 1 or claim 2 wherein a group of formula (III) is present and $R^6$ represents a hydrogen atom, a $C_1$–$C_6$ alkyl group, a halogen atom, a CF$_3$ group or a $C_1$–$C_6$ alkoxy group; and $R^7$ represents a hydrogen atom or a $C_1$–$C_6$ alkoxy group.

11. A compound as claimed in claim 10 wherein $R^6$ represents a hydrogen atom, methyl, fluorine, chlorine, bromine, CF$_3$, or methoxy, and $R^7$ represents a hydrogen atom or methoxy.

12. A compound as claimed in claim 1 wherein the group B is a bond, or —CO—, —CH$_2$—, —CH$_2$CH$_2$, —CH$_2$OCO—, —CH$_2$OCOCH$_2$—, —COO(CH$_2$)$_2$OCH$_2$CH$_2$—, —CONH(CH$_2$)$_2$—, —COOCH$_2$—, —COO(CH$_2$)$_2$—, —COO(CH$_2$)$_3$—, —CH$_2$OCH$_2$CO—, —COOCH(4-tert-butylphenyl)(CH$_2$)$_3$—, —CH$_2$OCH$_2$CH$_2$—, —COOCH(CH$_3$)(CH$_2$)$_3$—, —CH$_2$NHCOCH$_2$—, or —CH$_2$NHCO—.

13. A compound as claimed in claim 1 wherein in the group D, the groupings —R⁸—X and —R⁹—Y independently represent a phenyl, 4-chlorophenyl, 4-fluorophenyl, 4-bromophenyl, 4-methylphenyl, 2-pyridyl, or 6-[2-carboxyethenyl]pyrid-2-yl group.

14. A compound as claimed in claim 1 wherein the group D has formula (VIII), (IX) or (X):

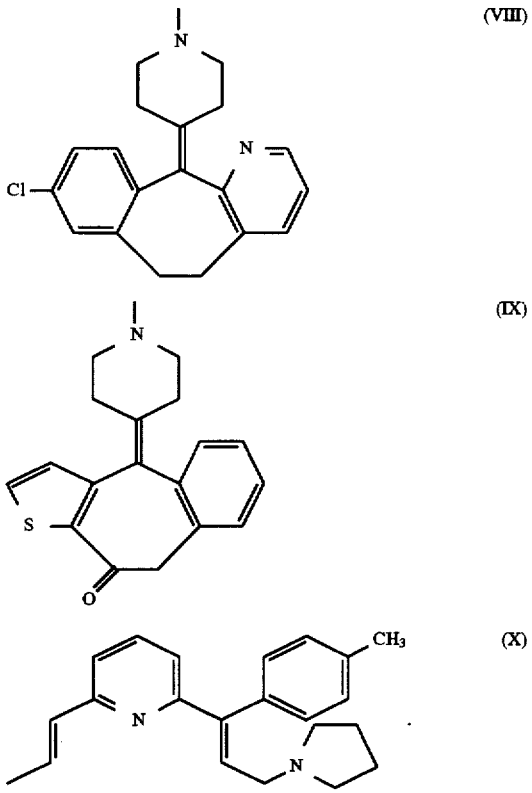

15. A compound as claimed in claim 1 selected from the group consisting of

N-Methyl-N-4-(1H-2-methylimidazo[4,5-c]pyridinylmethyl)-phenylsulphonyl-L-leucine-2-(4-benzhydryl-piperazin-1-yl)-ethyl ester, N-Methyl-N-4-(1H-2-methylimidazo[4,5-c]pyridinylmethyl)-phenylsulphonyl-L-leucine-3-(4-benzhydryl-piperazin-1-yl)-propyl ester, 4-(8-Chloro-5,6-dihydro-11H-benzo[5,6]cyclohepta[1,2-b]-pyridin-11-ylidene)-1-(N-methyl-N-4-{1H-2-methylimidazo[4,5-c]pyridinylmethyl}-phenylsulphonyl-L-leucyl)-piperidine amide, (E)-3-(6-[Pyrrolidino-1-{4-tolyl}prop-1E-enyl]-2-pyridyl)acrylic acid, N-methyl-N-4-(1H-2-methylimidazo[4,5-c]pyridinylmethyl)-phenylsulphonyl-L-leucyl ester, N-(S)-(1-Ethoxymethyl-3-methylbutyl)-N-{(E)-3-(6-[3-pyrrolidino-1-{4-tolyl}-prop-1E-enyl]-pyridin-2-yl)-prop-2-en-1-yl}-4-(1H-2-methylimidazo[4,5-c]pyridin-1-ylmethyl)-phenylsulphonamide, and (S)-4-Methyl-2-([4-1H-2-methylimidazo[4,5-c]pyridin-1-ylmethyl)-phenylsulphonyl]-(E)-{3-[6-(3-pyrrolidin-1-yl-{4-tolyl}-prop-1E-enyl]-prop-2-en-1-yl}-amino)-pentanoic acid ethyl ester, on a pharmaceutically or veterinarily acceptable acid addition salt or hydrate thereof.

16. A compound as claimed in claim 1 selected from the group consisting of

N-Methyl-N-4-(1H-2-methylimidazo[4,5-c]pyridinylmethyl)-phenylsulphonyl-L-leucine-2-(2-{4-[4-(chlorophenyl)-phenyl-methyl]-piperazin-1-yl}-ethoxy)-ethyl ester, N-Methyl-N-4-(1H-2-methylimidazo[4,5-c]pyridinylmethyl)phenylsulphonyl-L-leucine-2-(4-[1,1-dimethylethyl]phenyl)-4-(hydroxydiphenylmethyl)-1-piperidinebutyl ester, N-Methyl-N-4-(1H-2-methylimidazo[4,5-c]pyridinylmethyl)-phenylsulphonyl-L-leucine-2-(4-benzhydryl-piperazin-1-yl)-ethylamide, 4-(8-Chloro-5,6-dihydro-11H-benzo[5,6]cyclohepta[1,2-b]-pyridin-11-ylidene)-1-(N-methyl-N-4-{1H-2-methylimidazo[4,5-c]pyridinylmethyl}-phenylsulphonyl-L-leucinol)-piperidine carbamate, (4-Benzhydrylpiperazin-1-yl)-acetic acid, N-methyl-N-4-(1H-2-methylimidazo[4,5-c]-pyridinylmethyl)-phenylsulphonyl-L-leucyl ester, N-Methyl-N-(S)-(1-[4-benzhydrylpiperazin-1-yl]-methyl-3-methyl-butyl)-N-4-(1H-2-methylimidazo[4,5-c]pyridinylmethyl)-phenylsulphonamide, N-Methyl-N-(S)-(1-aminomethyl-[{4-benzhydrylpiperazin-1-yl}-acetamide]-3-methyl-butyl)-N-4-(1H-2-methylimidazo[4,5c]-pyridinylmethyl)-phenylsulphonamide, N-(S)-(4-Methyl-2-{methyl-[4-(1H-2-methyl-imidazo[4,5-c]pyridin-1-ylmethyl)-phenylsulphonyl]-amino}-pentyl)-3-[6-(3-pyrrolidin-1-yl-p-tolyl-prop-1E-enyl)-pyridin-2-yl] acrylamide, 2-[4-(8-Chloro-5,6-dihydro-11H-benzo[5,6]cyclohepta[1,2-b]pyridin-11-ylidene)-piperidin-1-yl]-N-(4-methyl-2-{methyl-[4-(1H-2-methylimidazo[4,5-c]pyridin-ylmethyl)-phenylsulphonyl]-amino}-pentyl)-acetamide, N-[1-{(4-Chlorobenzhydryl)-piperazin-1-ylmethyl}-3-methyl-butyl]-N-methyl-4-(1H-2-methylimidazo[4,5-c]pyridin-1-ylmethyl)-phenylsulphonamide, N-Methyl-N-4-(1H-2-methylimidazo[4,5-c]pyridinylmethyl)phenylsulphonyl-L-leucine-2-(4-(8-chloro-5,6-dihydro-11H-benzo[5,6]cyclohepta[1,2-b]pyridin- 11-ylidene}piperidin-1-yl)-ethyl ester, N-Methyl-N-4-(1H-2-methylimidazo[4,5-c]pyridinylmethyl)phenylsulphonyl-L-leucine-(R,S)-5-(4-benzhydrylpiperazin-1yl)-2-pentyl ester, 4-Methyl-2-{methyl-[4-(2-methyl-imidazo[4,5-c]pyridin-1-ylmethyl)-phenylsulphonyl]-amino}-pentanoic acid-(E)-3-(6-[3-pyrrolidino-1-{4-tolyl}-prop-1E-enyl]-pyridin-2-yl)-prop-2-en-1-yl ester, N-(1-{2-[4-(8-Chloro-5,6-dihydro-benzo[5,6]cyclohepta[1,2-b]pyridin-11-ylidene)-piperidin-1-yl]-2-oxo-ethoxymethyl}-3-methyl-butyl)-N-methyl-4-(1H-2-methylimidazo[4,5-c]pyridin-1-ylmethyl)-phenylsulphonamide, N-{2-[4-(8-Chloro-5,6-dihydro-11H-benzo[5,6]cyclohepta[1,2-b]pyridin-11-ylidene)-piperidin-1-yl]-2-oxo-ethyl)-N-(S)-(1-ethoxymethyl-3-methylbutyl)-4-(1H-2-methylimidazo[4,5-c]pyridin-1-ylmethyl)-phenylsulphonamide, N-(2-{[4-(R,S)-(4-Chlorophenyl)-phenyl-methyl]piperazin-1-yl}ethyl)-N-(S)-(1-ethoxymethyl-3-methylbutyl)-4-(1H-2-methylimidazo[4,5-c]pyridin-1ylmethyl)-phenylsulphonamide, N-(2-{[3-(R,S)-(4-Chlorophenyl)-3-pyridin-2-yl-propyl]-methylamino}ethyl)-N-(S)-(1-ethoxymethyl-3- methylbutyl)-4-(1H-2-methylimidazo[4,5-c]pyridin-1-ylmethyl)-phenylsulphonamide, N-(3-{[3-(R,S)-(4-Chlorophenyl)-3-pyridin-2-yl-propyl]-methylamino}propyl)-N-(S)-(1-ethoxymethyl-3-methylbutyl)-4-(1H-2-methylimidazo[4,5-c]pyridin-1-ylmethyl)-phenylsulphonamide.

N-(3-{[4-(R,S)-(4-Chlorophenyl)-phenyl-methyl]piperazin-1-yl}propyl)-N-(S)-(1-ethoxymethyl-3-methylbutyl)-4-(1H-2-methylimidazo[4,5-c]pyridin-1ylmethyl)-phenylsulphonamide, N-Cyclohexyl-N-{(E)-3-(6-[3-pyrrolidino-1-{4-tolyl}-prop-1E-enyl]-pyridin-2-yl)-prop-2en-1-yl}-4-(1H-2-methylimidazo[4,5-c]pyridin-1-ylmethyl)-phenylsulphonamide.

N-Methyl-N-{(E)-3-(6-[3-pyrrolidino-1-{4-tolyl}-prop-1E-enyl]-pyridin-2-yl)-prop-2-en-1-yl}-4-(1H-2-methylimidazo[4,5-c]pyridin-1-ylmethyl)-phenylsulphonamide, or a pharmaceutically or veterinarily acceptable acid addition salt or hydrate thereof.

17. A method of management of diseases or conditions mediated by histamine and/or PAF in mammals, which method comprises administering to the mammal an effective amount of a compound as claimed in claim 1, or a pharmaceutically or veterinarily acceptable salt thereof.

18. A method as claimed in claim 17, wherein the disease or condition is hypotension, thrombocytopenia, bronchoconstriction, circulatory shock, increased vascular permeability, allergic rhinitis, sinusitis, asthma, dermatitis, psoriasis, urticaria, anaphylactic shock, conjunctivitis, pruritis, inflammatory bowel disease and colitis.

19. A pharmaceutical or veterinary formulation comprising a compound as claimed claim 1 and a pharmaceutically and/or veterinarily acceptable carrier.

* * * * *